(12) United States Patent
Song et al.

(10) Patent No.: US 11,292,785 B2
(45) Date of Patent: Apr. 5, 2022

(54) NITROGEN-CONTAINING BENZOHETEROCYCLE COMPOUND COMPRISING CARBOXYLIC ACID GROUP, PREPARATION METHOD AND USE THEREOF

(71) Applicant: Sichuan Kelun-Biotech Biopharmaceutical Co., Ltd., Sichuan (CN)

(72) Inventors: Shuai Song, Sichuan (CN); Qiang Tian, Sichuan (CN); Yongyong Wu, Sichuan (CN); Mingliang Zhao, Sichuan (CN); Chaolei Wang, Sichuan (CN); Jiaqiang Cai, Sichuan (CN); Lichun Wang, Sichuan (CN); Jingyi Wang, Sichuan (CN)

(73) Assignee: Sichuan Kelun-Biotech Biopharmaceutical Co., Ltd., Sichuan (CN)

( * ) Notice: Subject to any disclaimer, the term of this patent is extended or adjusted under 35 U.S.C. 154(b) by 0 days.

(21) Appl. No.: 16/959,691

(22) PCT Filed: Jan. 18, 2019

(86) PCT No.: PCT/CN2019/072278
§ 371 (c)(1),
(2) Date: Jul. 2, 2020

(87) PCT Pub. No.: WO2019/149089
PCT Pub. Date: Aug. 8, 2019

(65) Prior Publication Data
US 2020/0361911 A1 Nov. 19, 2020

(30) Foreign Application Priority Data
Feb. 2, 2018 (CN) .......................... 201810104806.3

(51) Int. Cl.
*C07D 403/12* (2006.01)
*A61P 1/16* (2006.01)
(52) U.S. Cl.
CPC .............. *C07D 403/12* (2013.01); *A61P 1/16* (2018.01)
(58) Field of Classification Search
CPC .................................................. C07D 403/12
See application file for complete search history.

(56) References Cited

U.S. PATENT DOCUMENTS

2013/0023496 A1   1/2013   Tressler et al.

FOREIGN PATENT DOCUMENTS

| CN | 1649847 A | 8/2005 |
| CN | 106488769 A | 3/2017 |
| CN | 107207538 A | 9/2017 |
| EP | 1593681 A1 | 11/2005 |
| WO | 03014105 A1 | 2/2003 |
| WO | 03076411 A1 | 9/2003 |
| WO | 2015143367 A2 | 9/2015 |
| WO | 2016105527 A1 | 6/2016 |
| WO | 2017210526 A1 | 12/2017 |

OTHER PUBLICATIONS

PCT/CN2019/072278 International Search Report dated Apr. 16, 2019.
PCT/CN2019/072278 Written Opinion of the International Searching Authority dated Apr. 11, 2019.
Ikemoto, Tomomi, et al., Unusual Asymmetric Oxidation of Sulfide; the Diasteroselective Oxidation of Prochiral Sulfied-Chiral Acid Salt with Hydrogen Peroxide Without Metal, Tetrahedron 61, Apr. 2, 2005, pp. 5043-5048, Elsevier.
EP 19747600.5 Extended Supplementary European Search Report and Written Opinion.

*Primary Examiner* — Brian E McDowell
(74) *Attorney, Agent, or Firm* — Honigman LLP; Thomas A. Wootton, Esq.; Jonathan P. O'Brien

(57) ABSTRACT

Related is a nitrogen-containing benzoheterocycle compound containing a carboxylic acid group as shown in general formula (I), or a stereoisomer or pharmaceutically acceptable salt thereof. The compound has excellent pharmacokinetic properties and extremely remarkable liver targeting properties, and a pharmaceutical composition comprising the same may be used as a CCR antagonist, in particular a CCR2 and/or CCR5 antagonist and can be used in mediated disease, including, but not limited to, nonalcoholic fatty liver disease (NAFLD) or the like.

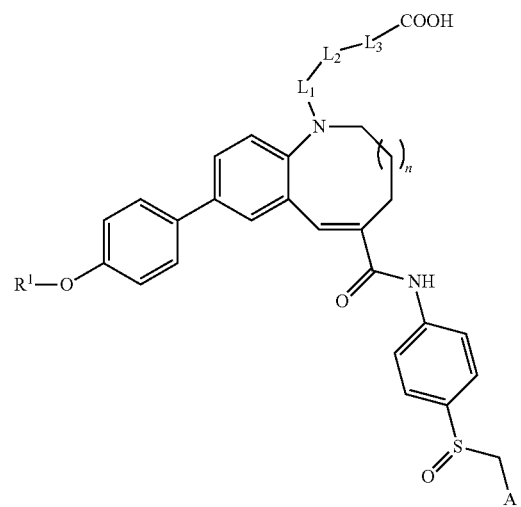

Formula I

13 Claims, No Drawings

NITROGEN-CONTAINING BENZOHETEROCYCLE COMPOUND COMPRISING CARBOXYLIC ACID GROUP, PREPARATION METHOD AND USE THEREOF

CROSS-REFERENCE TO RELATED APPLICATIONS

This application is a National Stage Application and claims priority under 35 U.S.C. § 371 to Patent Cooperation Treaty application PCT/CN2019/072278, filed Jan. 18, 2019, which claims the benefit of Chinese Patent Application No. 201810104806.3, filed Feb. 2, 2018, priority is claimed to both of these applications and the disclosures of these prior applications are considered part of the disclosure of this application and to the extent allowed the entire contents of the aforementioned applications are incorporated herein.

TECHNICAL FIELD

The present application relates to a nitrogen-containing benzoheterocycle compound containing a carboxylic acid group as shown in general formula (I), or a stereoisomer or pharmaceutically acceptable salt thereof, and a pharmaceutical composition comprising the same. The compound has excellent pharmacokinetic properties and extremely remarkable liver targeting properties, and can be used as a CCR antagonist, in particular a CCR2 and/or CCR5 antagonist. Therefore, the present application further relates to use of the compound in prevention and/or treatment of a disease mediated by CCR (in particular CCR2 and/or CCR5), including, but not limited to, nonalcoholic fatty liver disease (NAFLD).

BACKGROUND ART

The nonalcoholic fatty liver disease (NAFLD) refers to accumulation of excess fat in the form of triglycerides (steatosis) in the liver. It is defined to include, first of all, the presence of hepatic steatosis verified by liver imaging or histology, and secondly the absence of other factors that lead to secondary hepatic steatosis, such as alcohol consumption, drugs, genetic abnormalities and the like. The disease spectrum includes nonalcoholic simple fatty liver (NAFL), nonalcoholic steatohepatitis (NASH) and related cirrhosis and liver cancer.

The exact pathogenesis of NASH has not been elucidated and it is almost different in each patient. Although the disease is closely interrelated with insulin resistance, obesity, and metabolic syndrome, not all patients in these states will suffer from NAFLD and(or) NASH, and not all patients suffering from NAFLD and(or) NASH will experience these states. If NAFLD develops into NASH, risks of occurrences of cirrhosis, liver failure and liver cancer will increase greatly.

As researches on the pathogenesis of the nonalcoholic steatohepatitis (NASH) continue, looking for some new therapeutic targets or drugs becomes hotspots at now. The mechanisms of new drug against NASH are mainly classified into four categories: diabetes/lipid, bile acid/bile acid receptor pathway, apoptosis, and anti-inflammation/fibrosis. The main targets for NASH include peroxisome proliferator-activated receptor-α (PPARA) and β (PPARD) agonists, farnesyl ester-X receptor (FXR) agonists, monoclonal antibodies of inhibiting lysyl oxidase-like 2 (LOXL2) proteins, apoptosis signal-regulating protein kinase (ASK1) inhibitors, acetyl-CoA carboxylase (ACC) protein allosteric inhibitors, and chemokine receptor (CCR2/CCR5) antagonists.

Currently, drugs for NASH are not yet commercially available, and all compounds are still in clinical research stage. Obeticholic acid from Intercept Co. is the fastest-moving drug, and which is in phase III clinical studies. For Ceniciviroc from Takeda Pharmaceutical Co. of Japan phase-II clinical studies have been completed. International pharmaceutical companies such as Gilead, Bristol-Myers Squibb, and Astra Zeneca all have compounds in phase-II clinical studies. Medical therapy for NASH has become a research hotspot in the global medical field. WO03014105 describes a bicyclic compound and its use in anti-HIV, wherein $R^1$ is $C_{1-6}$ alkoxy-$C_{1-6}$ alkoxy; $R^2$ is tetrahydropyran-amino, alkyl-substituted imidazolyl, and alkyl-substituted triazolyl; $R^3$ is halogen, substituted alkyl, substituted alkoxy; $Y^a$ is oxygen, sulfinyl, sulfuryl, alkyl-substituted amino, and $Z^{2a}$ is sulfur, sulfinyl, sulfuryl. The specific description in this patent are not considered as part of the invention, and the compound therein has the following formula:

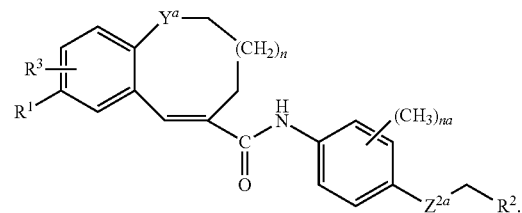

EP1593681 describes a tricyclic compound and use thereof in anti-HIV, wherein $R^{1a}$ is $C_{1-6}$ alkoxy-$C_{1-6}$ alkoxy; $R^{2a}$ is tetrahydropyran-amino, alkyl-substituted imidazolyl, and alkyl-substituted triazolyl; and $Z^{2a}$ may be sulfur, sulfinyl, sulfuryl; W is a group of formula (a) or (b); $R^3$ is halogen, substituted alkyl, substituted alkoxy. The specific description in this patent are not considered as part of the invention, and the compound therein has the following formula:

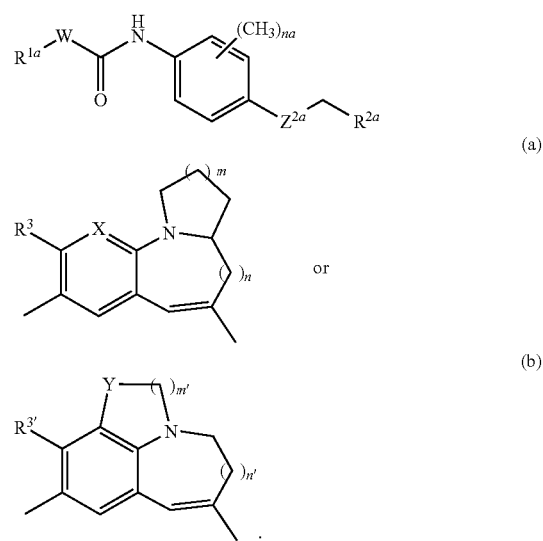

WO03076411 describes methods for synthesis of optical isomers having formula (c) and medical uses thereof for the treatment of HIV. The specific description in this patent is not considered as part of the invention, and the compound therein has the following formula:

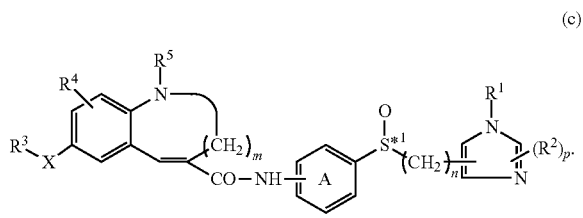

(c)

WO2015143367 describes uses of Cenicriviroc for the treatment of HIV and fibrosis, and WO2016105527 describes methods for the synthesis of Cenicriviroc. The specific description in these patents are not considered as part of the invention.

SUMMARY OF THE INVENTION

Through deep researches, the inventor surprisingly found that the compound obtained by introducing a carboxylic acid group into a nitrogen-containing benzoheterocyclic compound has very potent inhibitory effect against CCR2/CCR5, but has no obvious inhibitory effect against CYP and hERG, and good safety, as well as extremely remarkable liver targeting properties and excellent pharmacokinetic properties. The compound of the present application may be used for the treatment of a CCR2- and/or CCR5-mediated disease, including, but not limited to, nonalcoholic fatty liver disease (NAFLD) or the like. The present application is accomplished based on the above.

Particularly, the present application relates to the following:

In a first aspect, the present application provides a compound of general formula I or a pharmaceutically acceptable salt, ester, solvate (e.g., hydrate), stereoisomer, tautomer, prodrug thereof, or crystalline form, metabolite thereof, or a mixture of the aforementioned:

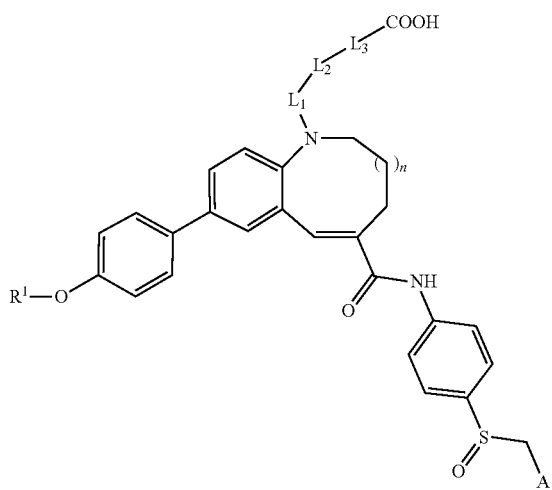

Formula I wherein $R^1$ is selected from hydrogen, deuterium, and $C_{1-6}$ alkyl, said $C_{1-6}$ alkyl is optionally substituted with $R^2$;

$L_1$ is selected from $C_{1-6}$ alkylene, $C_{3-10}$ cycloalkylene, $C_{6-10}$ arylene, $C_{5-12}$ heteroarylene, and 3- to 10-membered heterocyclylene;

$L_2$ is absent or selected from —NH—, $C_{2-6}$ alkylene, $C_{2-6}$ alkenylene, —$(C_{1-6}$ alkyleneoxy$)_{y1}$-$(C_{1-6}$ alkyleneoxy$)_{y2}$-, $C_{3-10}$ cycloalkylene, $C_{6-10}$ arylene, $C_{5-12}$ heteroarylene and 3- to 10-membered heterocyclylene; said —NH—, $C_{2-6}$ alkylene, $C_{2-6}$ alkenylene, $C_{3-10}$ cycloalkylene, $C_{6-10}$ arylene, $C_{5-12}$ heteroarylene, and 3- to 10-membered heterocyclylene are optionally substituted with one or more substituents independently selected from hydrogen, deuterium, halogen, hydroxyl, cyano, $C_{1-6}$ alkyl, $C_{1-6}$ haloalkyl, $C_{1-6}$ alkoxy, $C_{1-6}$ haloalkoxy, —C(O)$C_{1-4}$ alkyl, —COOR$^3$, —N(R$^3$)$_2$, $C_{3-10}$ cycloalkyl, 3- to 10-membered heterocyclic group, $C_{6-10}$ aryl, —CON(R$^3$)$_2$ and —NR$^3$CO$_2$R$^3$; said 3- to 10-membered heterocyclylene contains one or more ring members selected from N, NR$^3$, O, P, and S(O)$_z$; wherein $y_1$ and $y_2$ are each independently selected from 0, 1, 2, 3 or 4; z is selected from 0, 1 or 2;

$L^3$ is absent or selected from $C_{1-6}$ alkylene, $C_{2-6}$ alkenylene, $C_{2-6}$ alkynylene, $C_{3-10}$ cycloalkylene, $C_{6-10}$ arylene, $C_{5-12}$ heteroarylene, and 3- to 10-membered heterocyclylene;

$R^2$ is selected from hydrogen, deuterium, hydroxyl, amino, carboxyl, $C_{1-6}$ alkoxy, —$(C_{1-6}$ alkyleneoxy$)_{m1}$-$(C_{1-6}$ alkyleneoxy$)_{m2}$-$C_{1-6}$ alkyl, $(C_{1-6}$ alkyl$)_2$ amino, and 5- to 6-membered heterocyclyl containing one or more N, O or S; wherein $m_1$, $m_2$ are each independently selected from 0, 1, 2, 3 or 4;

$R^3$ is selected from hydrogen, deuterium, $C_{1-4}$ alkyl and $C_{3-6}$ cycloalkyl;

A is selected from 4- to 7-membered heterocyclyl or 5- to 10-membered heteroaryl, both of which are optionally substituted with a substituent selected from deuterium, $C_{1-6}$ alkyl and $C_{3-6}$ cycloalkyl that are optionally substituted with $R^6$, halogen, —CN, halogenated $C_{1-6}$ alkyl, $C_{3-6}$ heterocycloalkyl, $C_{6-10}$ aryl and $C_{5-12}$ heteroaryl; $R^6$ is selected from deuterium, hydroxyl, —CN, $C_{1-6}$ alkoxy and $C_{3-6}$ cycloalkoxy;

n is selected from 0, 1 or 2.

In some preferred embodiments, $R^1$ is selected from hydrogen and $C_{1-4}$ alkyl, said $C_{1-4}$ alkyl is optionally substituted with $R^2$; $R^2$ is selected from hydroxyl, carboxyl, $C_{1-6}$ alkoxy, —$(C_{1-6}$ alkyleneoxy$)_{m1}$-$(C_{1-6}$ alkyleneoxy$)_{m2}$-$C_{1-6}$ alkyl and 5- to 6-membered heterocyclyl containing one or more N, O or S; wherein $m_1$ and $m_2$ are independently selected from 0, 1, 2, 3 or 4.

In some preferred embodiments, $R^1$ is selected from $C_{1-4}$ alkyl, said $C_{1-4}$ alkyl is optionally substituted with $R^2$; $R^2$ is selected from hydroxyl, $C_{1-6}$ alkoxy, —$(C_{1-6}$ alkyleneoxy$)_{m1}$-$(C_{1-6}$ alkyleneoxy$)_{m2}$-$C_{1-6}$ alkyl and 5- to 6-membered heterocyclyl containing one or more N, O or S; wherein $m_1$ and $m_2$ are each independently selected from 0, 1 or 2.

In some preferred embodiments, $R^1$ is selected from $C_{1-4}$ alkyl, said $C_{1-4}$ alkyl is optionally substituted with $R^2$; $R^2$ is selected from $C_{1-4}$ alkoxy, —$(C_{1-4}$ alkyleneoxy$)_{m1}$-$(C_{1-4}$ alkyleneoxy$)_{m2}$-$C_{1-4}$ alkyl and 5- to 6-membered heterocyclyl containing one or more N, O or S; wherein $m_1$ and $m_2$ are each independently selected from 0, 1 or 2.

In some preferred embodiments, $R^1$ is selected from $C_{1-4}$ alkyl, said $C_{1-4}$ alkyl is optionally substituted with $R^2$; $R^2$ is selected from $C_{1-4}$ alkoxy.

In some preferred embodiments, $R^1$ is

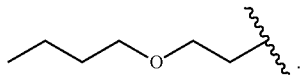 [SMILES: *CCOCCCC]

In some preferred embodiments, $L_1$ is selected from $C_{1-6}$ alkylene, $C_{3-10}$ cycloalkylene, $C_{6-10}$ arylene, and $C_{5-12}$ heteroarylene.

In some preferred embodiments, $L_1$ is selected from $C_{1-6}$ alkylene, $C_{3-7}$ cycloalkylene, $C_{6-8}$ arylene, and $C_{5-8}$ heteroarylene.

In some preferred embodiments, $L_1$ is selected from $C_{1-3}$ alkylene and $C_{3-5}$ cycloalkylene.

In some preferred embodiments, $L_1$ is selected from $C_{1-3}$ alkylene.

In some preferred embodiments, $L_1$ is selected from methylene and ethylene.

In some preferred embodiments, $L_2$ is absent or selected from —NH—, $C_{2-6}$ alkenylene, —($C_{1-6}$ alkyleneoxy)$_{y1}$-($C_{1-6}$ alkyleneoxy)$_{y2}$-, $C_{3-10}$ cycloalkylene, $C_{6-10}$ arylene, $C_{5-12}$ heteroarylene, and 3- to 10-membered heterocyclylene; said —NH—, $C_{2-6}$ alkenylene, —($C_{1-6}$ alkyleneoxy)$_{y1}$-($C_{1-6}$ alkyleneoxy)$_{y2}$-, $C_{3-10}$ cycloalkylene, $C_{6-10}$ arylene, $C_{5-12}$ heteroarylene, and 3- to 10-membered heterocyclylene are optionally substituted with one or more substituents independently selected from hydrogen, deuterium, halogen, hydroxyl, cyano, $C_{1-6}$ alkyl, $C_{1-6}$ haloalkyl, $C_{1-6}$ alkoxy, $C_{1-6}$ haloalkoxy, —C(O)$C_{1-4}$ alkyl, —COOR$^3$, —N(R$^3$)$_2$, $C_{3-10}$ cycloalkyl, 3- to 10-membered heterocyclyl, $C_{6-10}$ aryl, —CON(R$^3$)$_2$ and —NR$^3$CO$_2$R$^3$; said 3- to 10-membered heterocyclylene contains one or more ring members selected from N, NR$^3$, O, P, and S(O)$_z$; wherein $y_1$ and $y_2$ are each independently selected from 0, 1, 2, 3 or 4; z is selected from 0, 1 or 2.

In some preferred embodiments, $L_2$ is absent or selected from —NH—, $C_{2-6}$ alkylene, $C_{2-6}$ alkenylene, —($C_{1-6}$ alkyleneoxy)$_{y1}$-($C_{1-6}$ alkyleneoxy)$_{y2}$-, $C_{3-10}$ cycloalkylene, $C_{6-10}$ arylene, $C_{5-12}$ heteroarylene, and 3- to 10-membered heterocyclylene; said —NH—, $C_{2-6}$ alkylene, $C_{2-6}$ alkenylene, —($C_{1-6}$ alkyleneoxy)$_{y1}$-($C_{1-6}$ alkyleneoxy)$_{y2}$-, $C_{3-10}$ cycloalkylene, $C_{6-10}$ arylene, $C_{5-12}$ heteroarylene, and 3- to 10-membered heterocyclylene are optionally substituted with one or more substituents independently selected from hydrogen, deuterium, halogen, hydroxyl, cyano, $C_{1-3}$ alkyl, $C_{1-3}$ haloalkyl, $C_{1-3}$ haloalkoxy, —C(O)$C_{1-4}$ alkyl, —COOR$^3$ and —NR$^3$CO$_2$R$^3$; said 3- to 10-membered heterocyclylene contains one or more ring members selected from N, NR$^3$, O, P, and S(O)$_z$; wherein $y_1$ and $y_2$ are each independently selected from 0, 1, 2, 3 or 4; z is selected from 0, 1 or 2; R$^3$ is selected from hydrogen, deuterium, $C_{1-4}$ alkyl and $C_{3-6}$ cycloalkyl.

In some preferred embodiments, $L_2$ is absent or selected from —NH—, $C_{2-6}$ alkylene, $C_{2-6}$ alkenylene, —($C_{1-6}$ alkyleneoxy)$_{y1}$-($C_{1-6}$ alkyleneoxy)$_{y2}$-, $C_{3-10}$ cycloalkylene, $C_{6-10}$ arylene, $C_{5-12}$ heteroarylene, and 3- to 10-membered heterocyclylene; said —NH—, $C_{2-6}$ alkylene, $C_{2-6}$ alkenylene, —($C_{1-6}$ alkyleneoxy)$_{y1}$-($C_{1-6}$ alkyleneoxy)$_{y2}$-, $C_{3-10}$ cycloalkylene, $C_{6-10}$ arylene, $C_{5-12}$ heteroarylene, and 3- to 10-membered heterocyclylene are optionally substituted with one or more substituents independently selected from hydrogen, deuterium, halogen, hydroxyl, cyano, methyl, halomethyl, halomethoxy, —C(O)CH$_3$, —COOR$^3$ and —NR$^3$CO$_2$R$^3$; said 3- to 10-membered heterocyclylene contains one or more ring members selected from N, NR$^3$, O, P, and S(O)$_z$; wherein $y_1$ and $y_2$ are each independently selected from 0, 1, 2, 3 or 4; z is selected from 0, 1 or 2; R$^3$ is selected from hydrogen, deuterium, methyl and cyclopropyl.

In some preferred embodiments, $L_2$ is absent or selected from —NH—, $C_{2-6}$ alkylene, $C_{2-6}$ alkenylene, —($C_{1-6}$ alkyleneoxy)$_{y1}$-($C_{1-6}$ alkyleneoxy)$_{y2}$-, $C_{3-10}$ cycloalkylene, $C_{6-10}$ arylene, $C_{5-12}$ heteroarylene, and 3- to 10-membered heterocyclylene; said —NH—, $C_{2-6}$ alkylene, —($C_{1-6}$ alkyleneoxy)$_{y1}$-($C_{1-6}$ alkyleneoxy)$_{y2}$-, $C_{3-10}$ cycloalkylene, $C_{6-10}$ arylene, $C_{5-12}$ heteroarylene, and 3- to 10-membered heterocyclylene are optionally substituted with one or more substituents independently selected from hydrogen, deuterium, halogen, hydroxyl, cyano, methyl, halomethyl, halomethoxy, —C(O)CH$_3$, —COOR$^3$ and —NR$^3$CO$_2$R$^3$; said 3- to 10-membered heterocyclylene contains one or more ring members selected from N, NR$^3$, O, P, and S(O)$_z$; wherein $y_1$, $y_2$ are each independently selected from 0, 1, 2, 3 or 4; z is selected from 0, 1 or 2; R$^3$ is selected from hydrogen, deuterium, methyl and cyclopropyl.

In some preferred embodiments, $L_2$ is absent or selected from —NH—, $C_{2-4}$ alkylene, $C_{2-3}$ alkenylene, —($C_{1-3}$ alkyleneoxy)$_{y1}$-($C_{1-3}$ alkyleneoxy)$_{y2}$-, $C_{3-6}$ cycloalkylene, $C_{6-8}$ arylene, $C_{5-8}$ heteroarylene, and 3- to 6-membered heterocyclylene; said —NH—, $C_{2-4}$ alkylene, $C_{2-3}$ alkenylene, —($C_{1-3}$ alkyleneoxy)$_{y1}$-($C_{1-3}$ alkyleneoxy)$_{y2}$-, $C_{3-6}$ cycloalkylene, $C_{6-8}$ arylene, $C_{5-8}$ heteroarylene, and 3- to 6-membered heterocyclylene are optionally substituted with one or more substituents independently selected from hydrogen, deuterium, halogen, hydroxyl, cyano, methyl, halomethyl, halomethoxy, —C(O)CH$_3$, —COOR$^3$ and —NR$^3$CO$_2$R$^3$; said 3- to 6-membered heterocyclylene contains one or more ring members selected from N, NR$^3$, O, P, and S(O)$_z$; wherein $y_1$, $y_2$ are each independently selected from 0, 1, 2, 3 or 4; z is selected from 0, 1 or 2; R$^3$ is selected from hydrogen, deuterium, methyl and cyclopropyl.

In some preferred embodiments, $L_2$ is absent or selected from —NH—, $C_{2-4}$ alkylene, $C_{2-3}$ alkenylene, —($C_{1-3}$ alkyleneoxy)$_{y1}$-($C_{1-3}$ alkyleneoxy)$_{y2}$-, $C_{3-6}$ cycloalkylene, $C_{6-8}$ arylene, $C_{5-8}$ heteroarylene, and 3- to 6-membered heterocyclylene; said —NH—, $C_{2-3}$ alkenylene, —($C_{1-3}$ alkyleneoxy)$_{y1}$-($C_{1-3}$ alkyleneoxy)$_{y2}$-, $C_{3-6}$ cycloalkylene, $C_{6-8}$ arylene, $C_{5-8}$ heteroarylene, and 3- to 6-membered heterocyclylene are optionally substituted with one or more substituents independently selected from hydrogen, deuterium, halogen, hydroxyl, cyano, methyl, halomethyl, halomethoxy, —C(O)CH$_3$, —COOR$^3$ and —NR$^3$CO$_2$R$^3$; said 3- to 6-membered heterocyclylene contains one or more ring members selected from N, NR$^3$, O, P, and S(O)$_z$; wherein $y_1$ and $y_2$ are each independently selected from 0, 1, 2, 3 or 4; z is selected from 0, 1 or 2; R$^3$ is selected from hydrogen, deuterium, methyl and cyclopropyl.

In some preferred embodiments, $L_2$ is absent or selected from —NH—, —N(CH$_3$)—, —C(CH$_3$)$_2$—, —CH=CH—, —($C_{1-3}$ alkyleneoxy)$_{y1}$-($C_{1-3}$ alkyleneoxy)$_{y2}$-, $C_{3-6}$ cycloalkylene, $C_{6-8}$ arylene, $C_{5-8}$ heteroarylene, and 3- to 6-membered heterocyclylene, wherein $y_1$ and $y_2$ are each independently selected from 0, 1, or 2.

In some preferred embodiments, $L_2$ is absent.

In some preferred embodiments, $L_2$ is selected from $C_{2-4}$ alkylene.

In some preferred embodiments, $L_2$ is selected from —NH—, —N(CH$_3$)— and —C(CH$_3$)$_2$—.

In some preferred embodiments, $L_2$ is —C(CH$_3$)$_2$—.

In some preferred embodiments, $L_3$ is absent or selected from $C_{1-3}$ alkylene, $C_{2-3}$ alkenylene, $C_{2-3}$ alkynylene, $C_{3-6}$ cycloalkylene, $C_{6-8}$ arylene, $C_{5-8}$ heteroarylene, and 3- to 7-membered heterocyclylene.

In some preferred embodiments, $L_3$ is absent or selected from $C_{1-6}$ alkylene and $C_{2-6}$ alkenylene.

In some preferred embodiments, $L_3$ is absent or selected from —C(CH$_3$)$_2$—, —CH$_2$—, and —CH=CH—.

In some preferred embodiments, $L_3$ is absent.

In some preferred embodiments, $L_3$ is —CH$_2$—.

In some preferred embodiments, A is selected from 4- to 7-membered heterocyclyl or 5- to 10-membered heteroaryl.

In some preferred embodiments, A is selected from 4- to 7-membered nitrogen-containing heterocyclyl or 5- to 10-membered nitrogen-containing heteroaryl.

In some preferred embodiments, A is selected from 4- to 7-membered nitrogen-containing heterocyclyl or 5- to 10-membered nitrogen-containing heteroaryl, both of which are optionally substituted with a substituent selected from hydrogen, deuterium, $C_{1-6}$ alkyl and $C_{3-6}$ cycloalkyl that are optionally substituted with $R^6$, halogen, —CN, halogenated $C_{1-6}$ alkyl, $C_{3-6}$ heterocycloalkyl, $C_{6-10}$ aryl and $C_{5-12}$ heteroaryl; $R^6$ is selected from deuterium, hydroxyl, —CN, $C_{1-6}$ alkoxy and $C_{3-6}$ cycloalkoxy.

In some preferred embodiments, A is selected from 5- or 6-membered nitrogen-containing heteroaryl.

In some preferred embodiments, A is selected from 5- or 6-membered nitrogen-containing heteroaryl optionally substituted with a substituent selected from deuterium, $C_{1-6}$ alkyl and $C_{3-6}$ cycloalkyl that are optionally substituted with $R^6$, halogen, —CN, halogenated $C_{1-6}$ alkyl, $C_{3-6}$ heterocycloalkyl, $C_{6-10}$ aryl and $C_5$-12 heteroaryl; $R^6$ is selected from deuterium, hydroxyl, —CN, $C_{1-6}$ alkoxy and $C_{3-6}$ cycloalkoxy.

In some preferred embodiments, A is a 5-membered nitrogen-containing heteroaryl.

In some preferred embodiments, A is a 5-membered nitrogen-containing heteroaryl optionally substituted with a substituent selected from deuterium, $C_{1-6}$ alkyl and $C_{3-6}$ cycloalkyl that are optionally substituted with $R^6$, halogen, —CN, halogenated $C_{1-6}$ alkyl, $C_{3-6}$ heterocycloalkyl, $C_{6-10}$ aryl, and $C_{5-12}$ heteroaryl; $R^6$ is selected from deuterium, hydroxyl, —CN, $C_{1-6}$ alkoxy and $C_{3-6}$ cycloalkoxy;

preferably, A is a 5-membered nitrogen-containing heteroaryl substituted with a substituent, and the substituent is $C_{1-6}$ alkyl (e.g., propyl).

In some preferred embodiments, A is

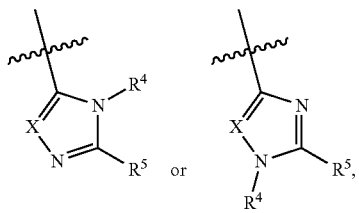

wherein $R^4$ is selected from hydrogen, deuterium, or $C_{1-6}$ alkyl and $C_{3-6}$ cycloalkyl that are optionally substituted with $R^6$, $R^6$ is selected from deuterium, hydroxyl, —CN, $C_{1-4}$ alkoxy and $C_{3-6}$ cycloalkoxy, $R^5$ is selected from hydrogen, deuterium, halogen, —CN, $C_{1-6}$ alkyl, halogenated $C_{1-6}$ alkyl, $C_{1-6}$ alkylene-CN, $C_{1-6}$ alkylene-OH, $C_{1-6}$ alkylene-$C_{1-6}$ alkoxy, $C_{3-6}$ cycloalkyl, $C_{3-6}$ heterocycloalkyl, $C_{6-10}$ aryl and $C_{5-12}$ heteroaryl, X is selected from N and C—$R^5$, each $R^5$ is identical or different.

In some preferred embodiments, A is selected from

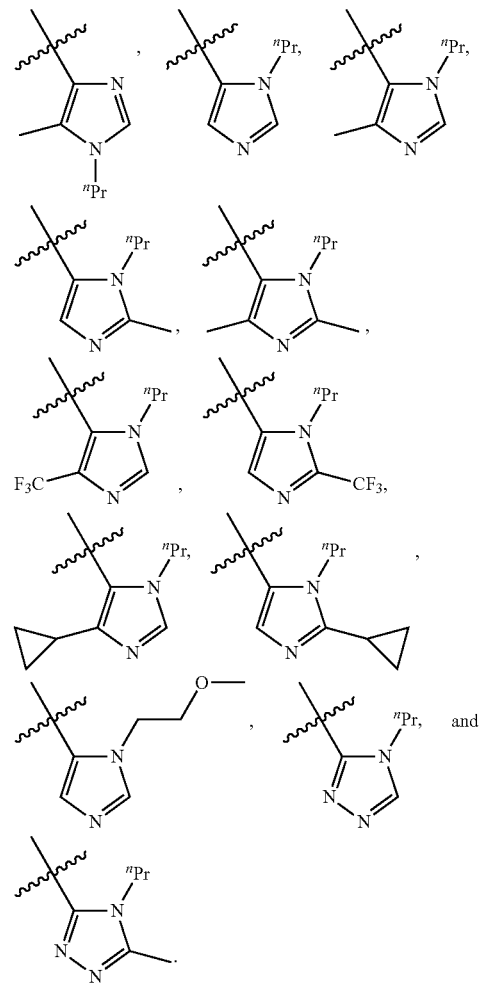

In some preferred embodiments, $R^4$ is $C_{1-6}$ alkyl optionally substituted with $R^6$, $R^6$ is selected from deuterium, hydroxyl, —CN, and $C_{1-4}$ alkoxy.

In some preferred embodiments, $R^4$ is $C_{1-6}$ alkyl optionally substituted with $R^6$, $R^6$ is selected from hydroxyl and $C_{1-4}$ alkoxy.

In some preferred embodiments, $R^4$ is $C_{1-4}$ alkyl optionally substituted with $R^6$, $R^6$ is selected from hydroxyl and $C_{1-4}$ alkoxy.

In some preferred embodiments, $R^4$ is $C_{1-4}$ alkyl optionally substituted with $R^6$, $R^6$ is selected from hydrogen, hydroxyl, methoxy, and ethoxy.

In some preferred embodiments, $R^4$ is $C_{1-4}$ alkyl optionally substituted with $R^6$, $R^6$ is selected from methoxy and ethoxy.

In some preferred embodiments, $R^4$ is selected from n-propyl and

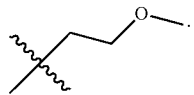 [SMILES: *CCOC]

In some preferred embodiments, $R^5$ is independently selected from hydrogen, deuterium, $C_{1-6}$ alkyl, halogenated $C_{1-6}$ alkyl, $C_{1-6}$ alkylene-OH, $C_{1-6}$ alkylene-$C_{1-6}$ alkoxy, $C_{3-6}$ cycloalkyl, and $C_{3-6}$ heterocycloalkyl.

In some preferred embodiments, $R^5$ is independently selected from hydrogen, deuterium, $C_{1-6}$ alkyl, halogenated $C_{1-6}$ alkyl, and $C_{3-6}$ cycloalkyl.

In some preferred embodiments, $R^5$ is independently selected from hydrogen, methyl, trifluoromethyl and cyclopropyl.

In some preferred embodiments, $R^5$ is hydrogen.

In some preferred embodiments, X is selected from N and C—$R^5$, $R^5$ is selected from hydrogen, deuterium, $C_{1-6}$ alkyl, halogenated $C_{1-6}$ alkyl, $C_{1-6}$ alkylene-OH, $C_{1-6}$ alkylene-$C_{1-6}$ alkoxy, $C_{3-6}$ heterocycloalkyl, and $C_{3-6}$ heterocycloalkyl.

In some preferred embodiments, X is selected from N and C—$R^5$, $R^5$ is selected from hydrogen, deuterium, $C_{1-6}$ alkyl, halogenated $C_{1-6}$ alkyl, and $C_{3-6}$ cycloalkyl.

In some preferred embodiments, X is selected from N and C—$R^5$, $R^5$ is selected from hydrogen, methyl, trifluoromethyl, and cyclopropyl.

In some preferred embodiments, $L_1$ is selected from $C_{1-6}$ alkylene, $C_{3-10}$ cycloalkylene, $C_{6-10}$ arylene and $C_{5-12}$ heteroarylene; preferably, $L_1$ is selected from $C_{1-3}$ alkylene and $C_{3-5}$ cycloalkylene; more preferably, $L_1$ is selected from methylene and ethylene;

$L_2$ is absent or selected from —NH—, $C_{2-4}$ alkylene, $C_{2-3}$ alkenylene, —($C_{1-3}$ alkyleneoxy)$_{y1}$-($C_{1-3}$ alkyleneoxy)$_{y2}$-, $C_{3-6}$ cycloalkylene, $C_{6-8}$ arylene, $C_{5-8}$ heteroarylene and 3- to 6-membered heterocyclylene; said —NH—, $C_{2-4}$ alkylene, $C_2$-3 alkenylene, —($C_{1-3}$ alkyleneoxy)$_{y1}$-($C_{1-3}$ alkyleneoxy)$_{y2}$-, $C_{3-6}$ cycloalkylene, $C_{6-8}$ arylene, $C_{5-8}$ heteroarylene, and 3- to 6-membered heterocyclylene are optionally substituted with one or more substituents that are independently selected from hydrogen, deuterium, halogen, hydroxyl, cyano, methyl, halomethyl, halomethoxy, —C(O)CH$_3$, —COOR$^3$ and —NR$^3$CO$_2$R$^3$; said 3- to 6-membered heterocyclylene contains one or more ring members selected from N, NR$^3$, O, P, and S(O)$_z$; wherein $y_1$ and $y_2$ are each independently selected from 0, 1, 2, 3 or 4; z is selected from 0, 1 or 2; $R^3$ is selected from hydrogen, deuterium, methyl and cyclopropyl; preferably, $L_2$ is absent or selected from —NH—, —N(CH$_3$)—, —C(CH$_3$)$_2$—, —CH=CH—, —(C$_{1-3}$ alkyleneoxy)$_{y1}$-(C$_{1-3}$ alkyleneoxy)$_{y2}$-, C$_{3-6}$ cycloalkylene, C$_{6-8}$ arylene, C$_{5-8}$ heteroarylene and 3- to 6-membered heterocyclylene, wherein $y_1$ and $y_2$ are each independently selected from 0, 1 or 2; more preferably, $L_2$ is absent or selected from —NH—, —N(CH$_3$)— and —C(CH$_3$)$_2$—;

$L_3$ is absent or selected from $C_{1-3}$ alkylene, $C_{2-3}$ alkenylene, $C_{2-3}$ alkynylene, $C_{3-6}$ cycloalkylene, $C_{6-8}$ arylene, $C_{5-8}$ heteroarylene, and 3- to 7-membered heterocyclylene; preferably, $L_3$ is absent or selected from $C_{1-6}$ alkylene and $C_{2-6}$ alkenylene; more preferably, $L_3$ is absent or selected from —C(CH$_3$)$_2$—, —CH$_2$—, and —CH=CH—; particularly preferably, $L_3$ is absent or —CH$_2$—.

In some preferred embodiments, n is selected from 1 or 2, preferably, n is 1.

In some preferred embodiments, the present application provides a compound of general formula I$_a$ or I$_b$ or a pharmaceutically acceptable salt, ester, solvate (e.g., hydrate), stereoisomer, tautomer, prodrug thereof, or crystalline form, metabolite thereof, or a mixture of the aforementioned:

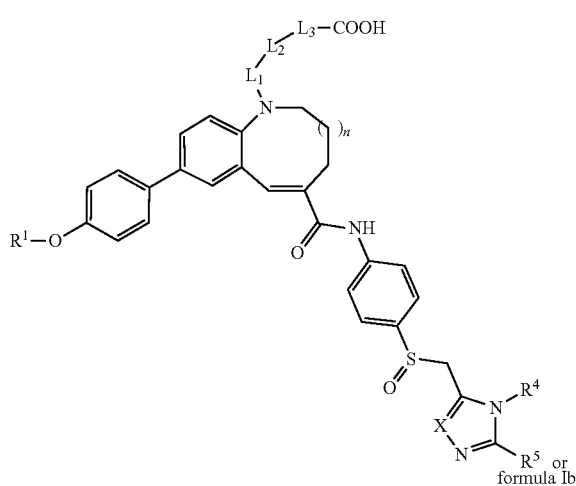

formula Ia

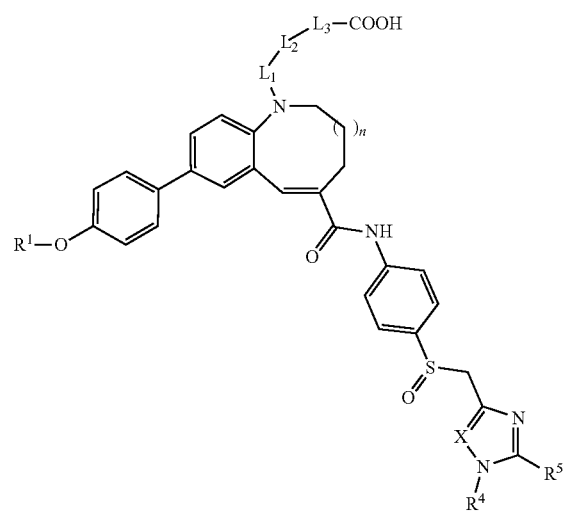

formula Ib wherein $R^1$, $R^4$, $R^5$, $L_1$, $L_2$, $L_3$, X and n are as defined above.

In some preferred embodiments, the present application provides compounds of formula II$_a$ and formula II$_{a'}$ or a pharmaceutically acceptable salt, ester, solvate (e.g., hydrate), stereoisomer, tautomer, prodrug thereof, or crystalline form, metabolite thereof, or a mixture of the aforementioned:

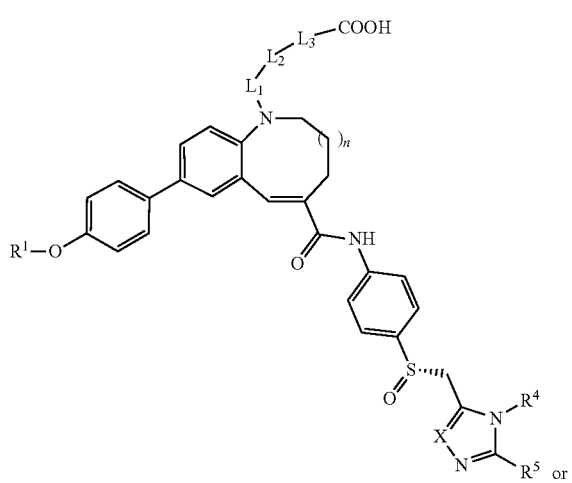

formula IIa

-continued formula IIa'

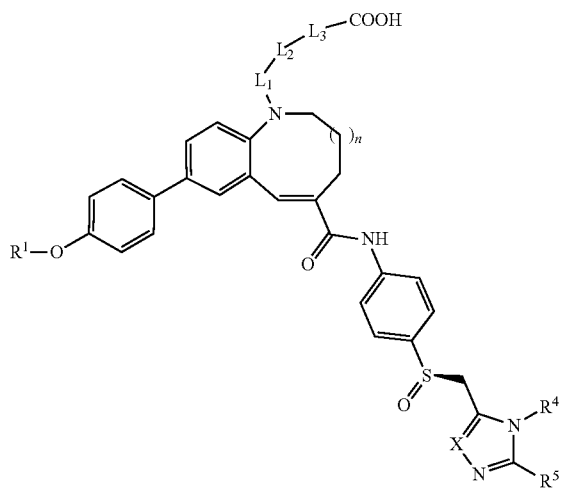

wherein $R^1$, $R^4$, $R^5$, X, $L_1$, $L_2$, $L_3$ or n are as defined above.

In some preferred embodiments, the present application provides compounds of general formula $II_a$ and formula $II_{a'}$, wherein $R^1$ is selected from hydrogen, deuterium, and $C_{1-6}$ alkyl, said $C_{1-6}$ alkyl is optionally substituted with $R^2$, $R^2$ is selected from hydrogen, deuterium, hydroxy, amino, carboxy, $C_{1-6}$ alkoxy, —$(C_{1-6}$ alkyleneoxy$)_{m1}$-$(C_{1-6}$ alkyleneoxy$)_{m2}$-$C_{1-6}$ alkyl, ($C_{1-6}$ alkyl)$_2$ amino, and 5- to 6-membered heterocyclyl containing one or more N, O or S atoms; wherein $m_1$ and $m_2$ are each independently selected from 0, 1, 2, 3 or 4;

preferably, $R^1$ is $C_{1-6}$ alkyl, said $C_{1-6}$ alkyl is optionally substituted by $C_{1-6}$ alkoxy;

preferably, $R^1$ is $C_{1-3}$ alkyl, said $C_{1-3}$ alkyl is optionally substituted by $C_{1-6}$ alkoxy;

preferably, $R^1$ is ethyl, said ethyl is substituted with n-butoxy.

In some preferred embodiments, the present application provides compounds of general formula $II_a$ and formula $II_{a'}$, wherein X is selected from N and C—$R^5$, $R^5$ is selected from hydrogen, deuterium, halogen, —CN, $C_{1-6}$ alkyl, halogenated $C_{1-6}$ alkyl, $C_{1-6}$ alkylene-CN, $C_{1-6}$ alkylene-OH, $C_{1-6}$ alkylene-$C_{1-6}$ alkoxy, $C_{3-6}$ cycloalkyl, $C_{3-6}$ heterocycloalkyl, $C_{6-10}$ aryl, and $C_{5-12}$ heteroaryl;

preferably, X is selected from N and C—$R^5$, $R^5$ is selected from hydrogen, deuterium, $C_{1-6}$ alkyl, halogenated $C_{1-6}$ alkyl and $C_{3-6}$ cycloalkyl;

preferably, X is selected from N and C—$R^5$, $R^5$ is selected from hydrogen, $C_{1-3}$ alkyl, halogenated $C_{1-3}$ alkyl and $C_{3-6}$ cycloalkyl;

preferably, X is selected from N and C—$R^5$, $R^5$ is selected from hydrogen, methyl, trifluoromethyl and cyclopropyl;

preferably, X is C—$R^5$, $R^5$ is selected from hydrogen and methyl.

In some preferred embodiments, the present application provides compounds of general formula $II_a$ and formula $II_{a'}$, wherein $R^4$ is selected from hydrogen, deuterium, or $C_{1-6}$ alkyl and $C_{3-6}$ cycloalkyl optionally substituted with $R^6$, $R^6$ is selected from hydrogen, deuterium, hydroxyl, —CN, $C_{1-4}$ alkoxy and $C_{3-6}$ cycloalkoxy;

preferably, $R^4$ is selected from $C_{1-6}$ alkyl and $C_{3-6}$ cycloalkyl, both of which are optionally substituted with $R^6$, $R^6$ is $C_{1-4}$ alkoxy;

preferably, $R^4$ is selected from $C_{1-3}$ alkyl optionally substituted with $R^6$, $R^6$ is $C_{1-3}$ alkoxy;

preferably, $R^4$ is selected from propyl and methoxy-substituted ethyl;

preferably, $R^4$ is n-propyl.

In some preferred embodiments, the present application provides compounds of general formulae $II_a$ and $II_{a'}$, wherein:

$L_1$ is selected from $C_{1-6}$ alkylene, $C_{3-10}$ cycloalkylene, $C_{6-10}$ arylene, $C_{5-12}$ heteroarylene, and 3- to 10-membered heterocyclylene;

preferably, $L_1$ is $C_{1-3}$ alkylene; preferably, $L_1$ is selected from methylene and ethylene.

In some preferred embodiments, the present application provides compounds of general formulae $II_a$ and $II_{a'}$, wherein:

$L_2$ is absent or selected from —NH—, $C_{2-6}$ alkylene, $C_{2-6}$ alkenylene, —($C_{1-6}$ alkyleneoxy$)_{y1}$-($C_{1-6}$ alkyleneoxy$)_{y2}$-, $C_{3-10}$ cycloalkylene, $C_{6-10}$ arylene, $C_{5-12}$ heteroarylene and 3- to 10-membered heterocyclylene; said —NH—, $C_{2-6}$ alkylene, $C_{2-6}$ alkenylene, —($C_{1-6}$ alkyleneoxy$)_{y1}$-($C_{1-6}$ alkyleneoxy$)_{y2}$-, $C_{3-10}$ cycloalkylene, $C_{6}$-10 arylene, $C_{5-12}$ heteroarylene, and 3- to 10-membered heterocyclylene are optionally substituted with one or more substituents that are independently selected from hydrogen, deuterium, halogen, hydroxyl, cyano, $C_{1-3}$ alkyl, $C_{1-3}$ haloalkyl, $C_{1-3}$ haloalkoxy, —C(O)$C_{1-4}$ alkyl, —COOR$^3$ and —NR$^3$CO$_2$R$^3$; said 3- to 10-membered heterocyclylene contains one or more ring members selected from N, NR$^3$, O, P, and S(O)$_z$; wherein $y_1$ and $y_2$ are each independently selected from 0, 1, 2, 3 or 4; z is selected from 0, 1 or 2; $R^3$ is selected from hydrogen, deuterium, $C_{1-4}$ alkyl and $C_{3-6}$ cycloalkyl;

preferably, $L_2$ is absent or selected from —NH—, —N(CH$_3$)—, —C(CH$_3$)$_2$—, —CH=CH—, —($C_{1-3}$ alkyleneoxy$)_{y1}$-($C_{1-3}$ alkyleneoxy$)_{y2}$-, $C_{3-6}$ cycloalkylene, $C_{6-8}$ arylene, $C_{5-8}$ heteroarylene and 3- to 6-membered heterocyclylene, wherein $y_1$ and $y_2$ are each independently selected from 0, 1 or 2;

preferably, $L_2$ is absent or selected from —NH—, —N(CH$_3$)— and —C(CH$_3$)$_2$—;

preferably, $L_2$ is selected from —NH—, —N(CH$_3$)— and —C(CH$_3$)$_2$—.

In some preferred embodiments, $L_2$ is absent.

In some preferred embodiments, the present application provides compounds of general formulae $II_a$ and $II_{a'}$, wherein, $L_3$ is absent or selected from $C_{1-6}$ alkylene, $C_{2-6}$ alkenylene, $C_{2-6}$ alkynylene, $C_{3-10}$ cycloalkylene, $C_{6-10}$ arylene, $C_{5-12}$ heteroarylene, and 3- to 10-membered heterocyclylene;

preferably, $L_3$ is absent or selected from $C_{1-3}$ alkylene, $C_{2-3}$ alkenylene, $C_{2-3}$ alkynylene, $C_{3-6}$ cycloalkylene, $C_{6-8}$ arylene, $C_{5-8}$ heteroarylene, and 3- to 7-membered heterocyclylene;

preferably, $L_3$ is absent or selected from $C_{1-6}$ alkylene and $C_{2-6}$ alkenylene;

preferably, $L_3$ is absent or selected from —C(CH$_3$)$_2$—, —CH$_2$—, and —CH=CH—;

preferably, $L_3$ is absent.

In some preferred embodiments, the present application provides compounds of general formulae $II_a$ and $II_{a'}$, wherein, n is selected from 0, 1 or 2; preferably, n is selected from 0 and 1;

preferably, n is 1.

In some preferred embodiments, the present application provides compounds of general formulae $II_a$ and $II_{a'}$, wherein:

$R^1$ is $C_{1-3}$ alkyl, said $C_{1-3}$ alkyl is optionally substituted with $C_{1-6}$ alkoxy;

X is selected from N and C—$R^5$, $R^5$ is selected from hydrogen, methyl, trifluoromethyl and cyclopropyl;

$R^4$ is selected from propyl and methoxy-substituted ethyl;

$L_1$ is $C_{1-3}$ alkylene; preferably, $L_1$ is selected from methylene and ethylene;

$L_2$ is absent or selected from —NH—, —N(CH$_3$)— and —C(CH$_3$)$_2$—;

$L_3$ is absent or selected from —C(CH$_3$)$_2$—, —CH$_2$—, and —CH═CH—;

n is selected from 0 and 1; preferably, n is 1.

In some preferred embodiments, the present application provides compounds of general formulae $II_b$ and formula $II_{b'}$, or a pharmaceutically acceptable salt, ester, solvate (e.g., hydrate), stereoisomer, tautomer, prodrug thereof, or crystalline form, metabolite thereof, or a mixture of the aforementioned:

formula IIb

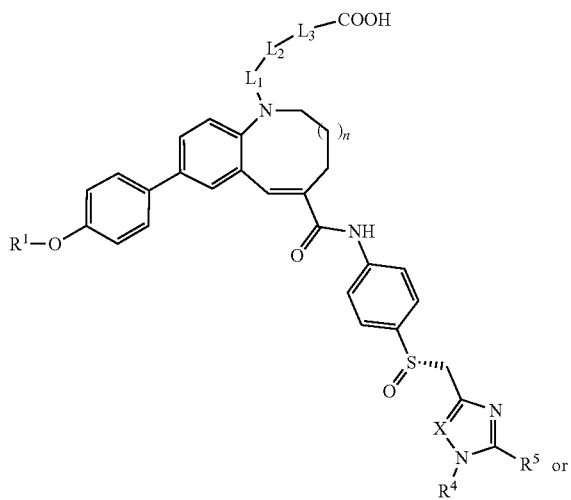

formula IIb'

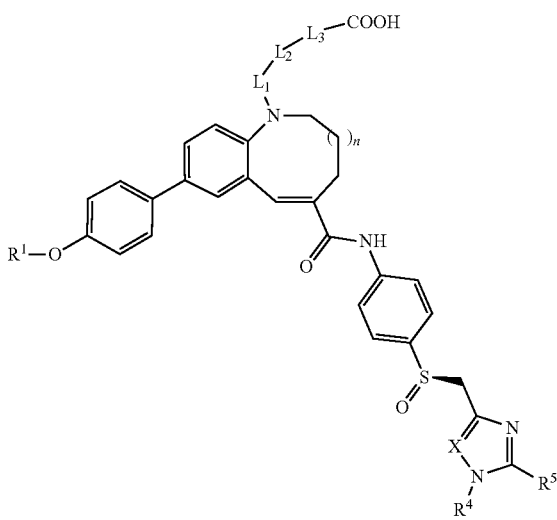

wherein $R^1$, $R^4$, $R^5$, X, $L_1$, $L_2$, $L_3$ or n are as defined above.

In some preferred embodiments, the present application provides a compound or a pharmaceutically acceptable salt, ester, solvate (e.g., hydrate), stereoisomer, tautomer, prodrug thereof, or crystalline form, metabolite thereof, or a mixture of the aforementioned, wherein the compound is selected from:

1

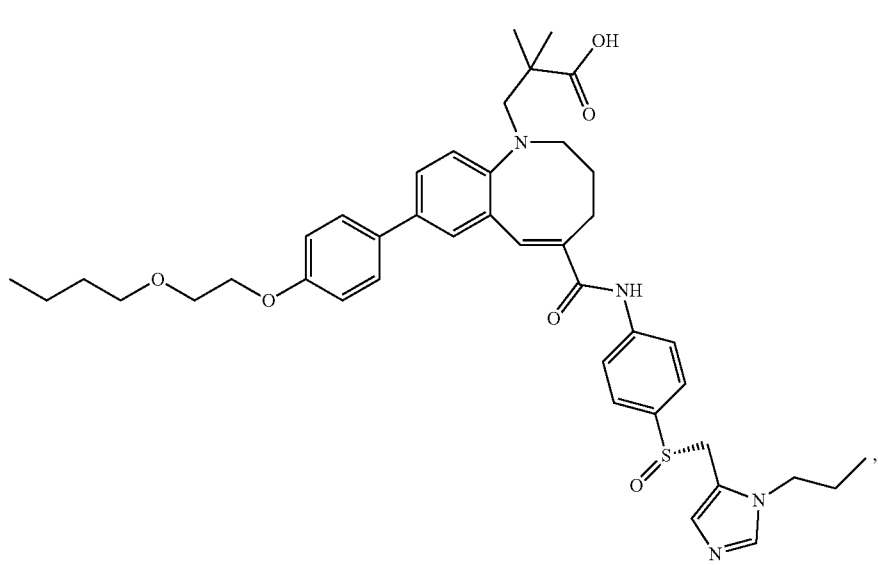

-continued
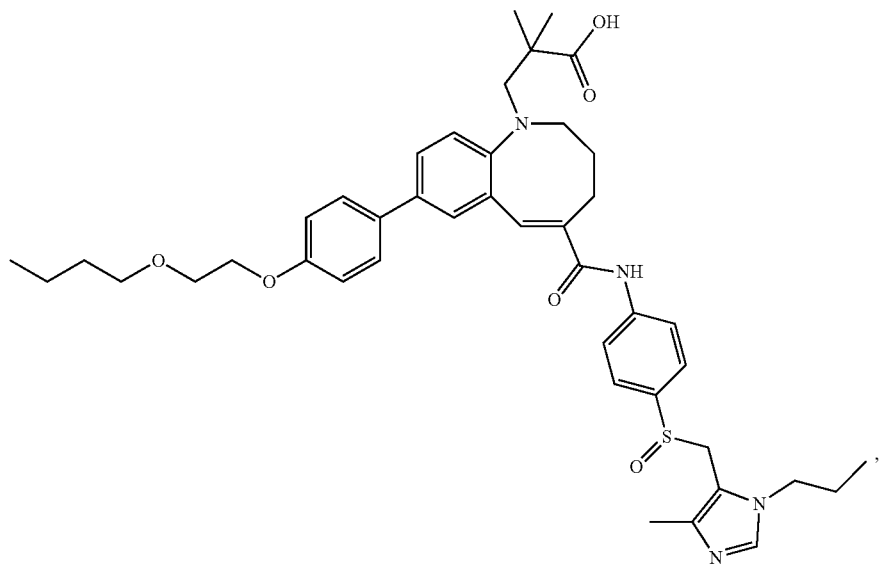
2
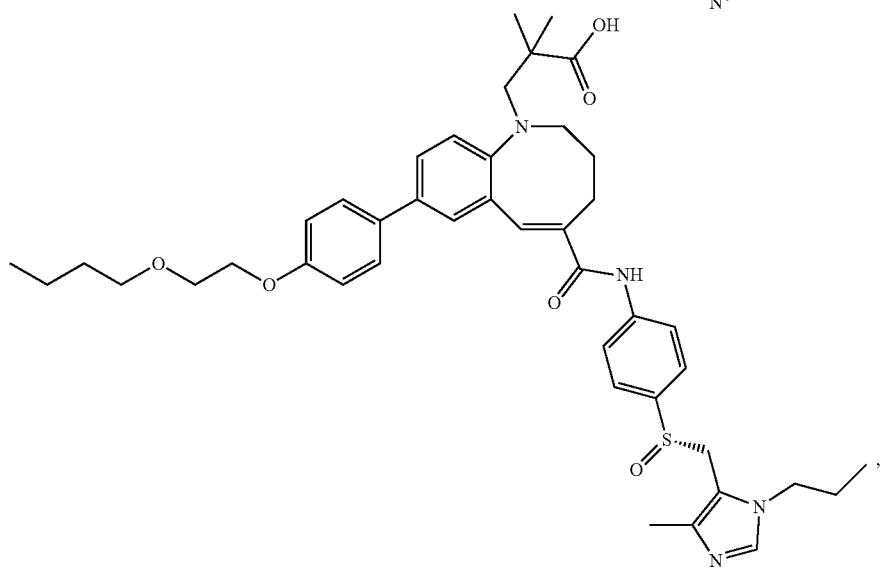
3
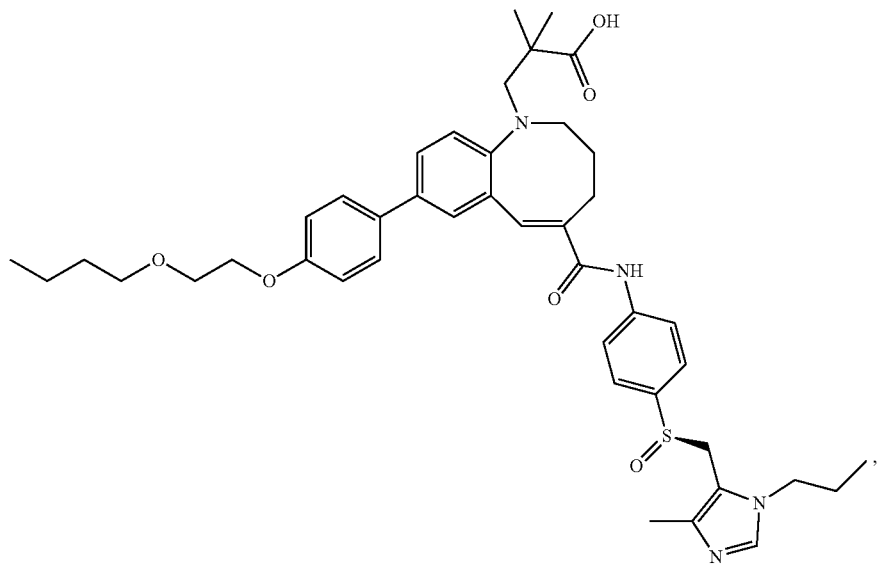
4

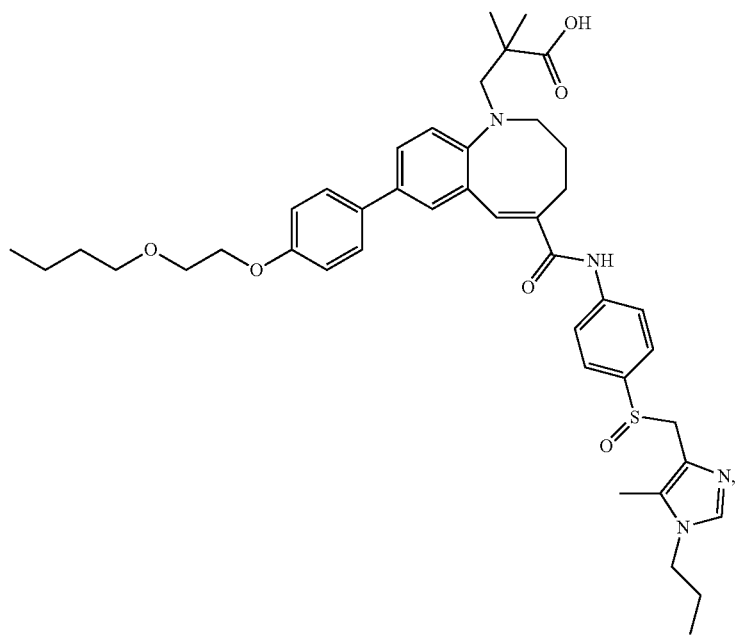
5
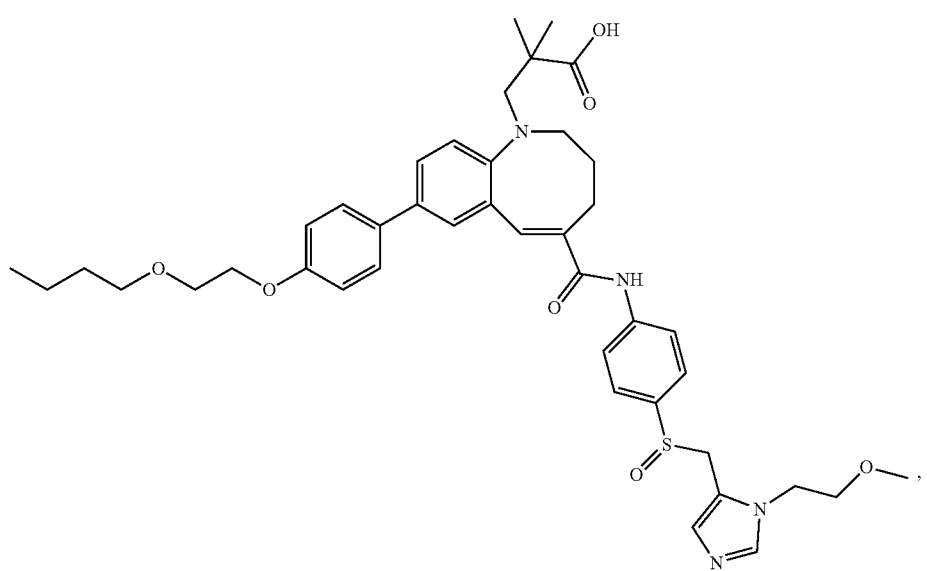
6

-continued
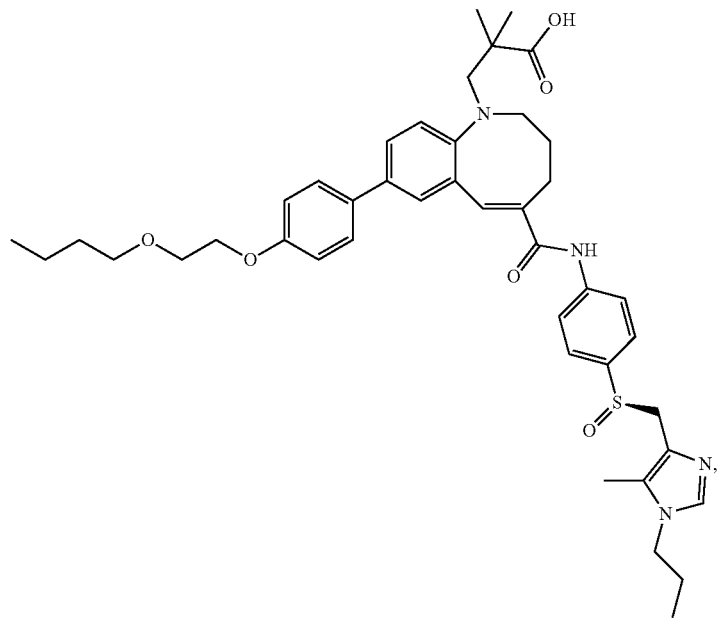
7
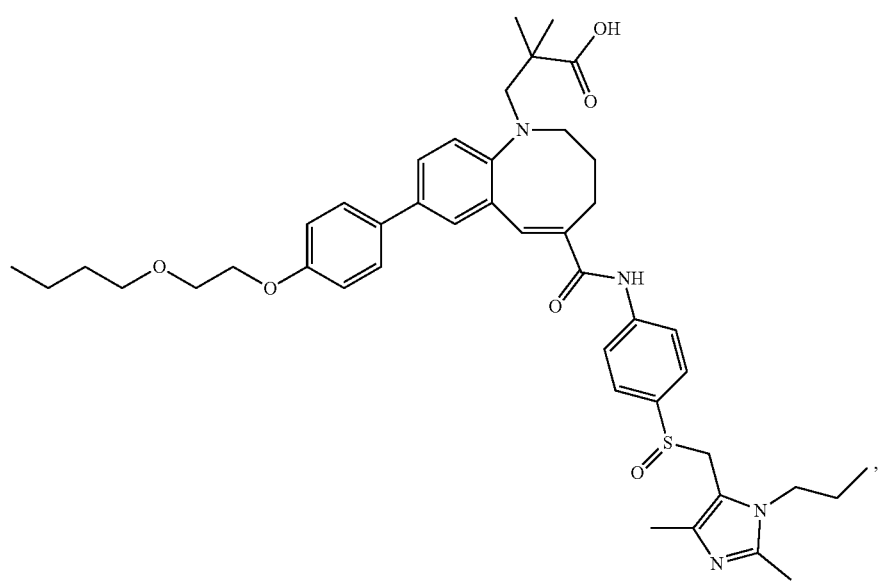
8

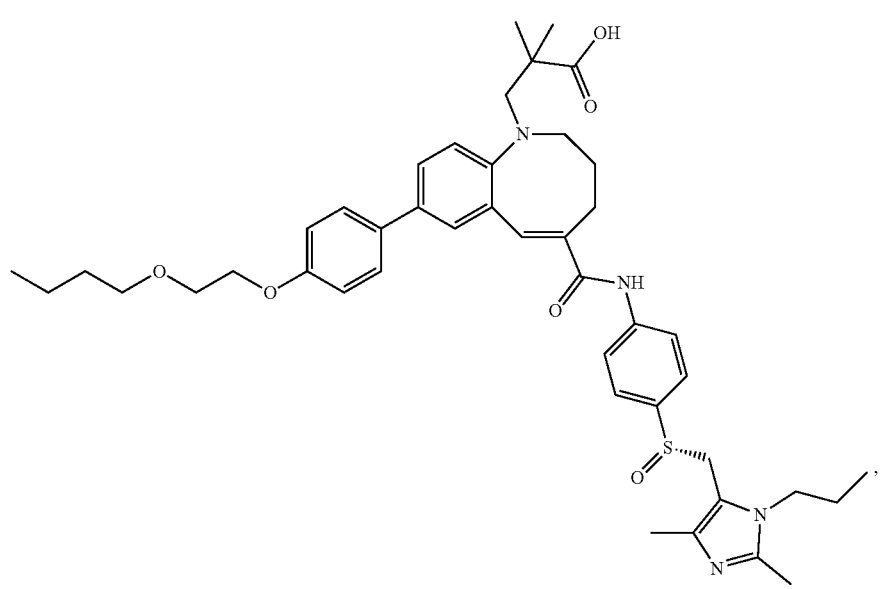
9
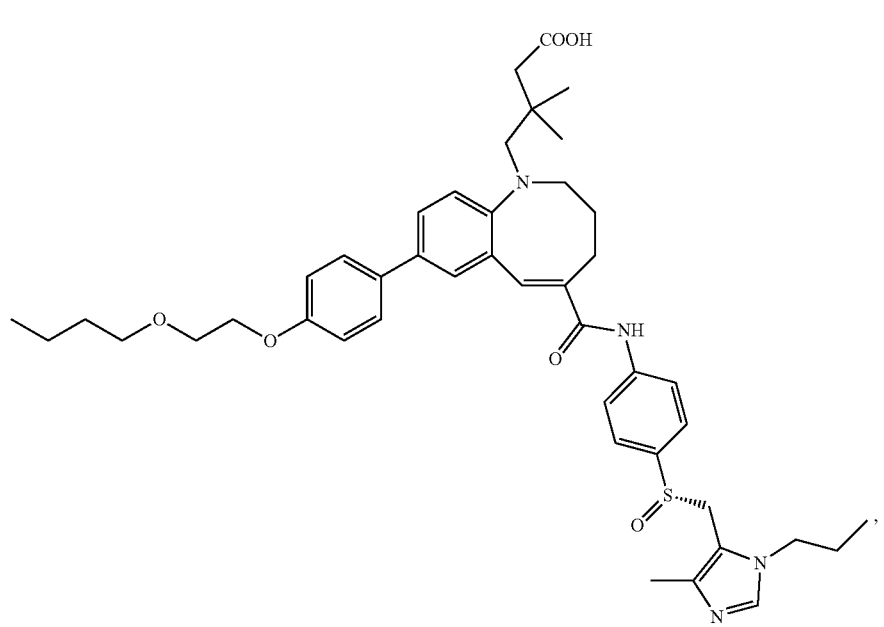
10

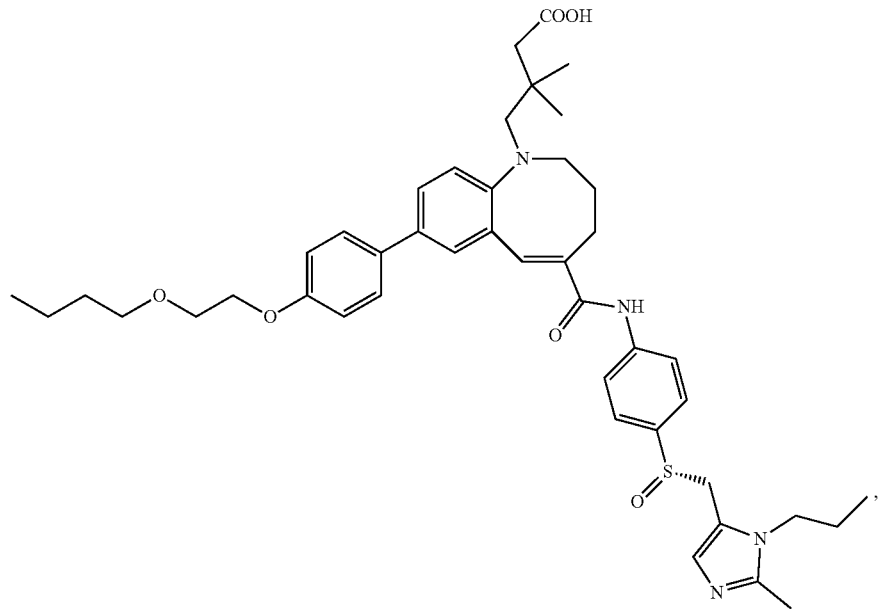
11
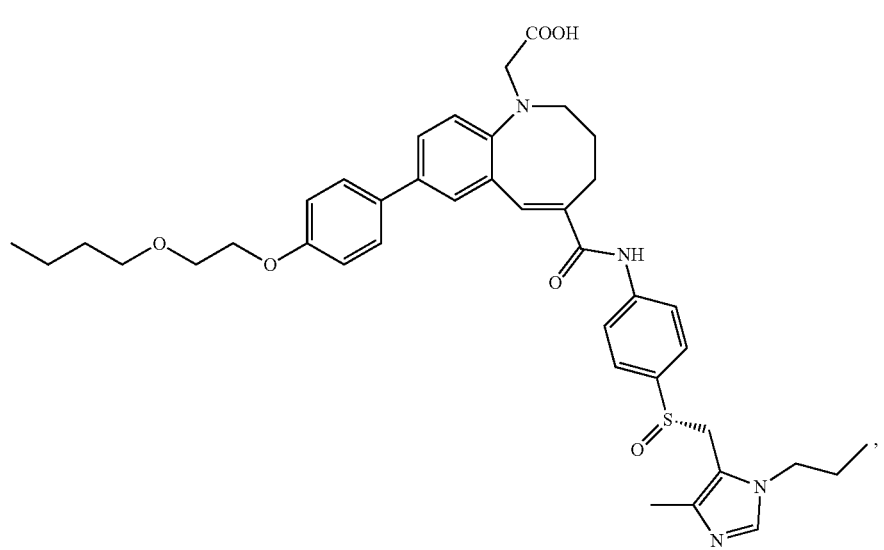
12

-continued
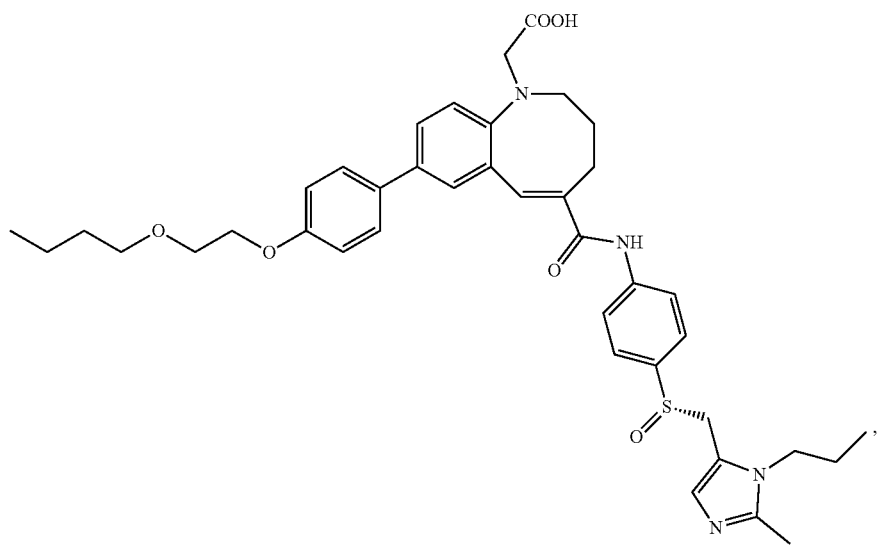
13
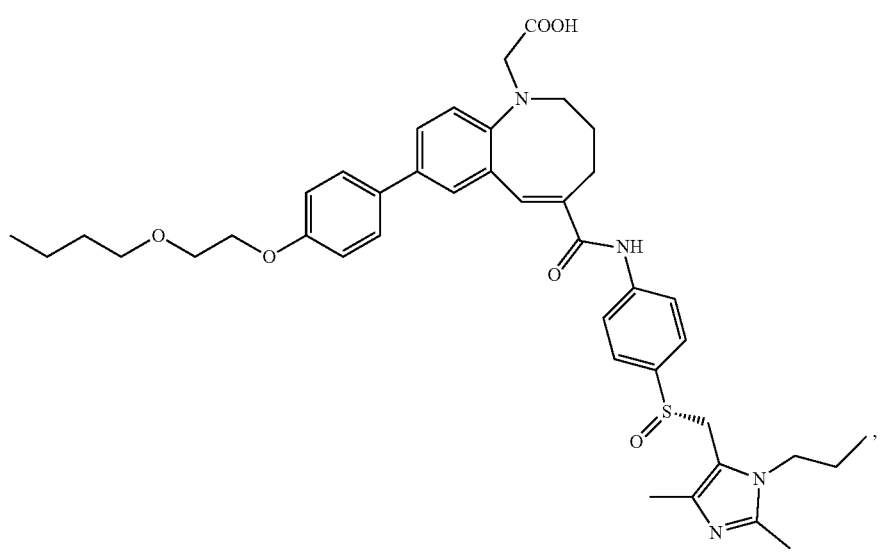
14
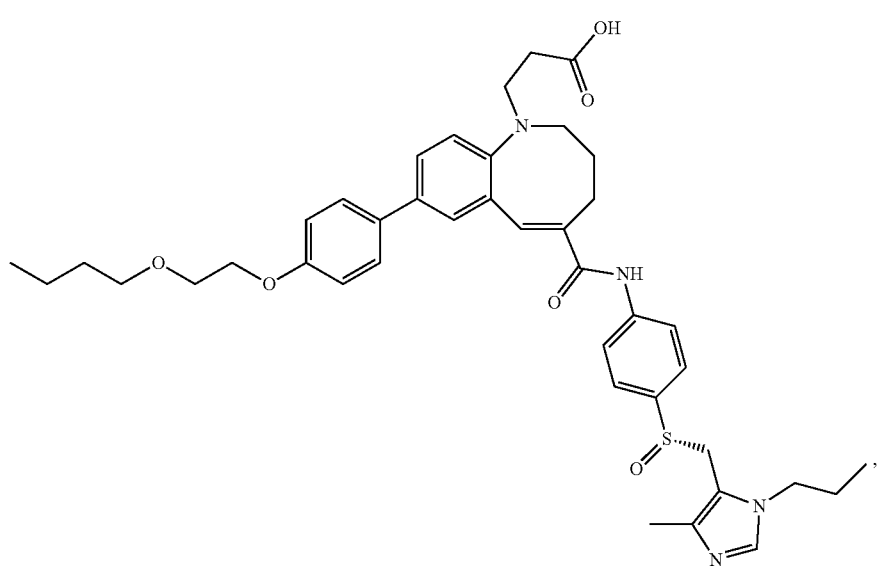
15

-continued
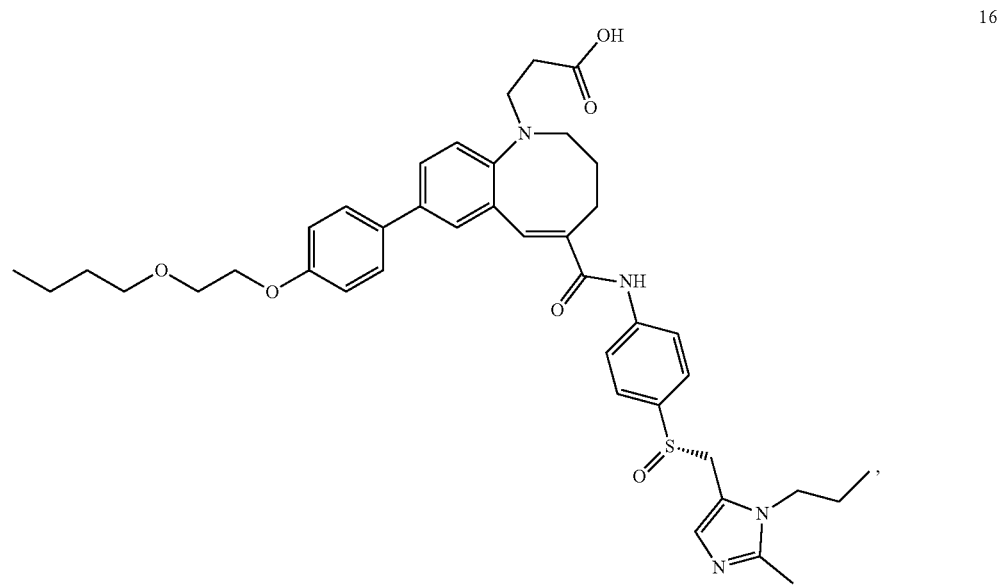
16
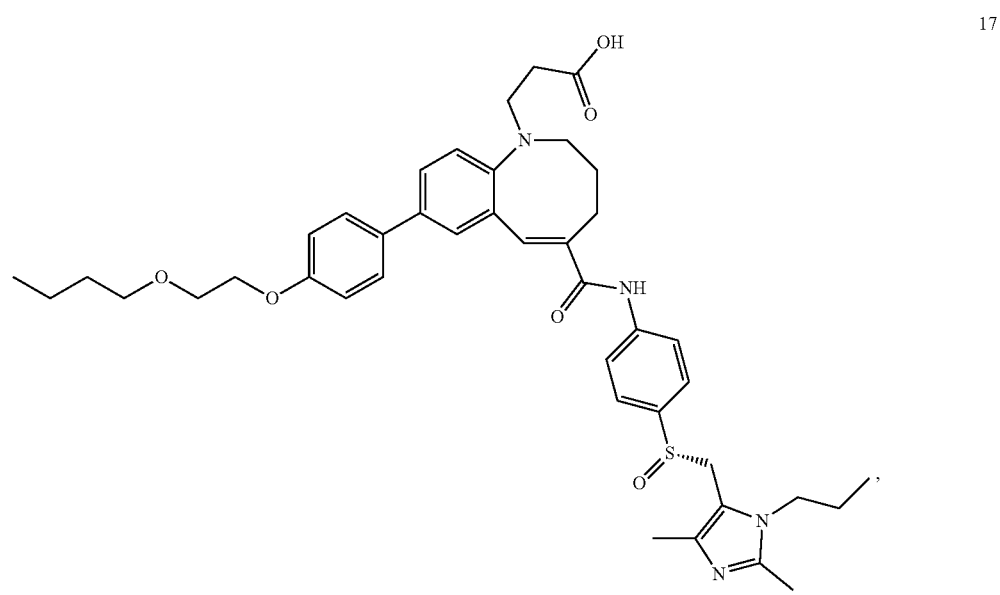
17

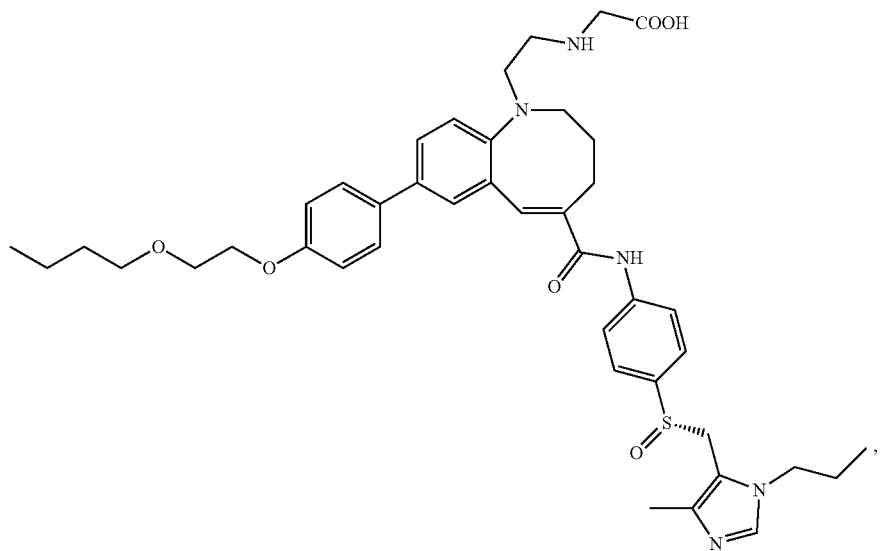
18
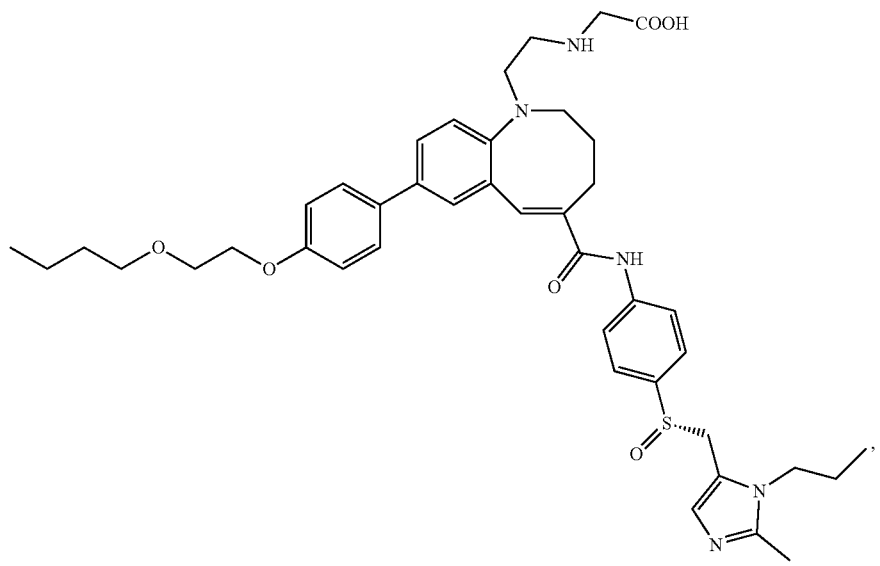
19
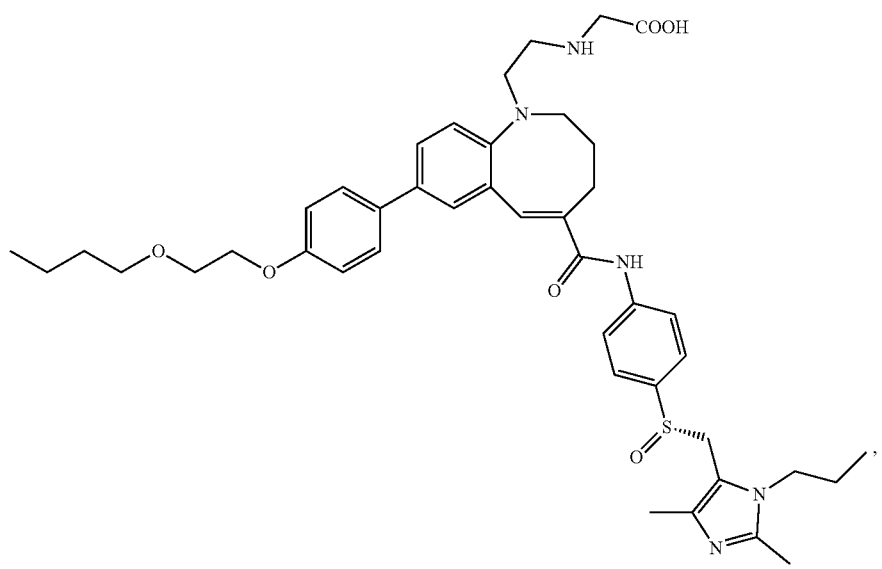
20

21
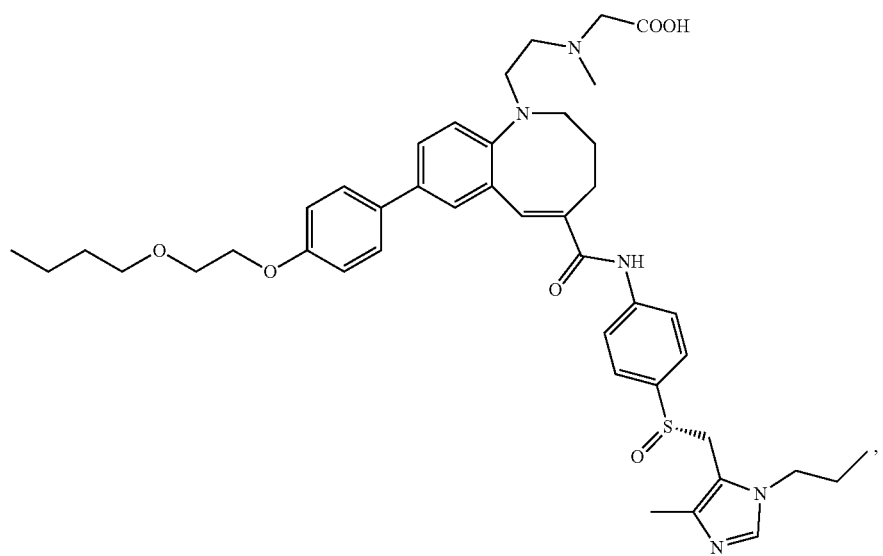
22
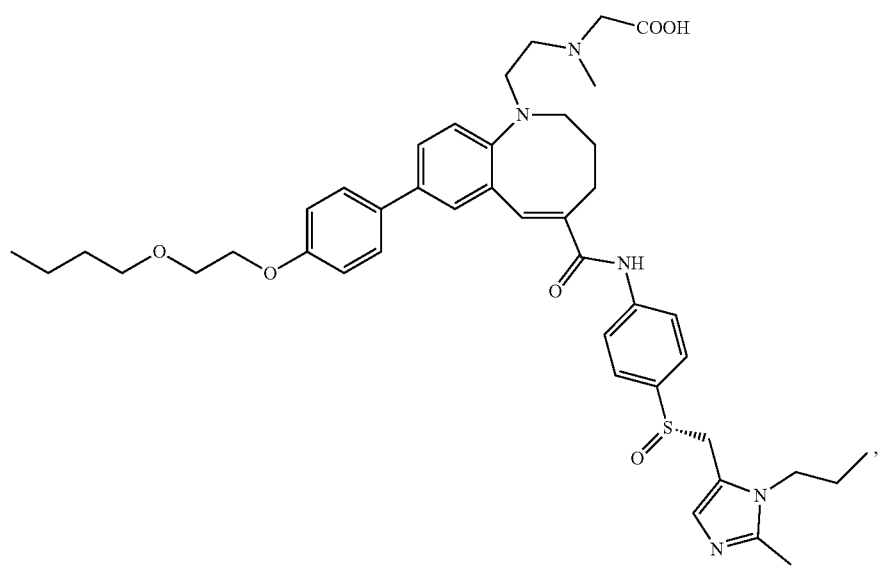
23
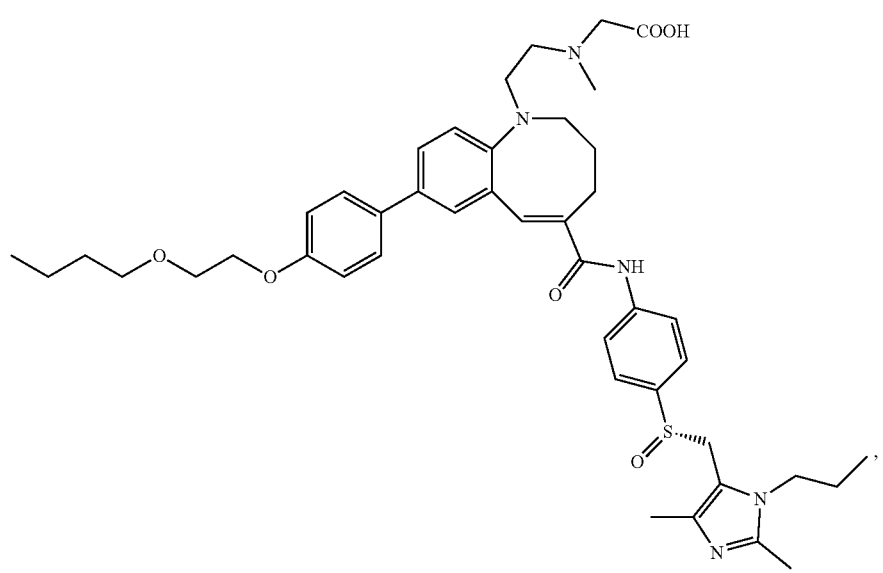

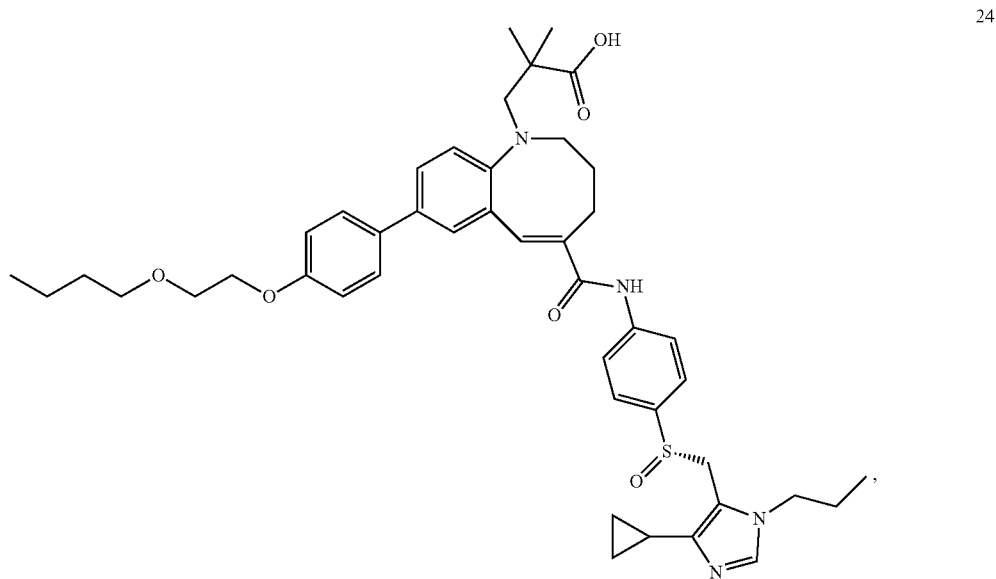
24
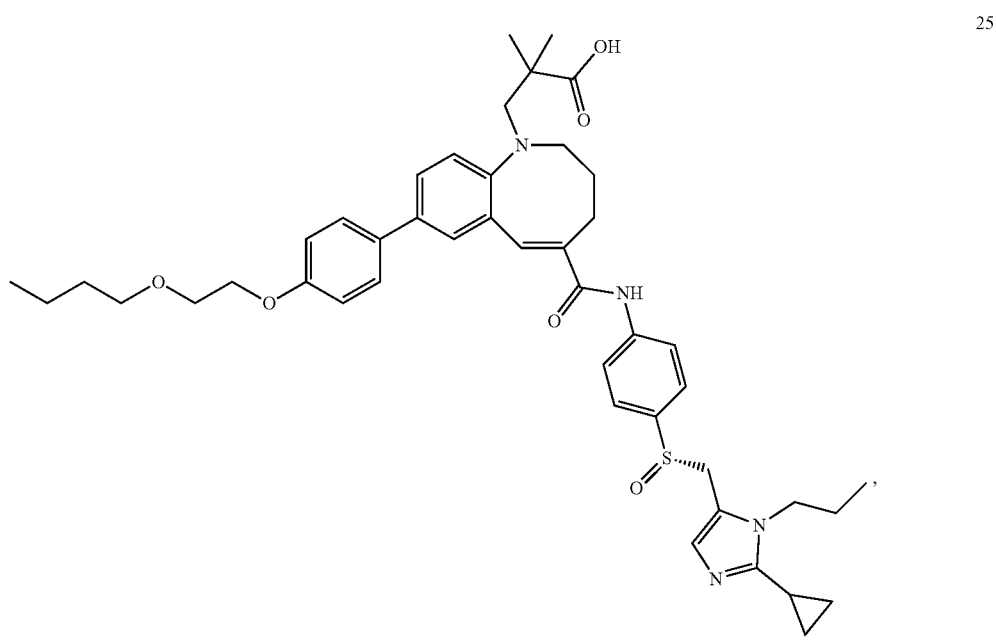
25

-continued
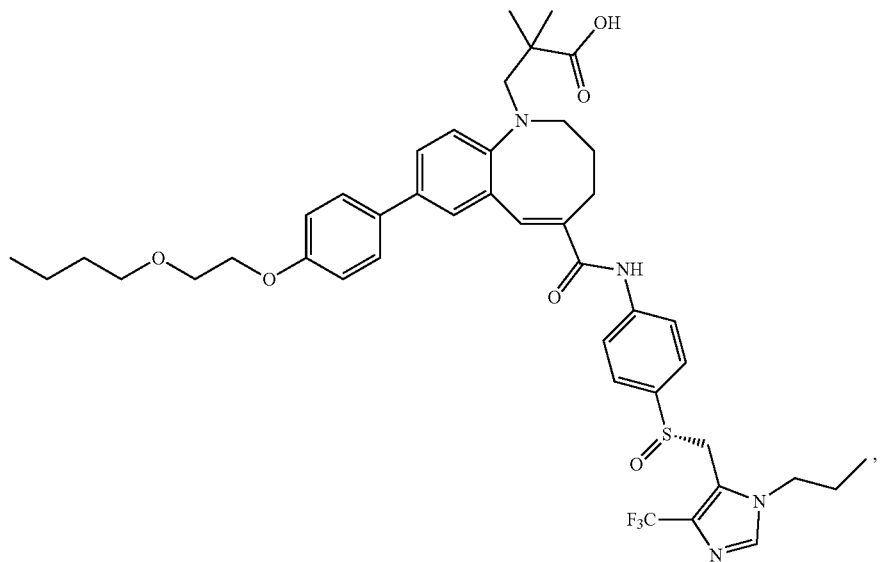
26
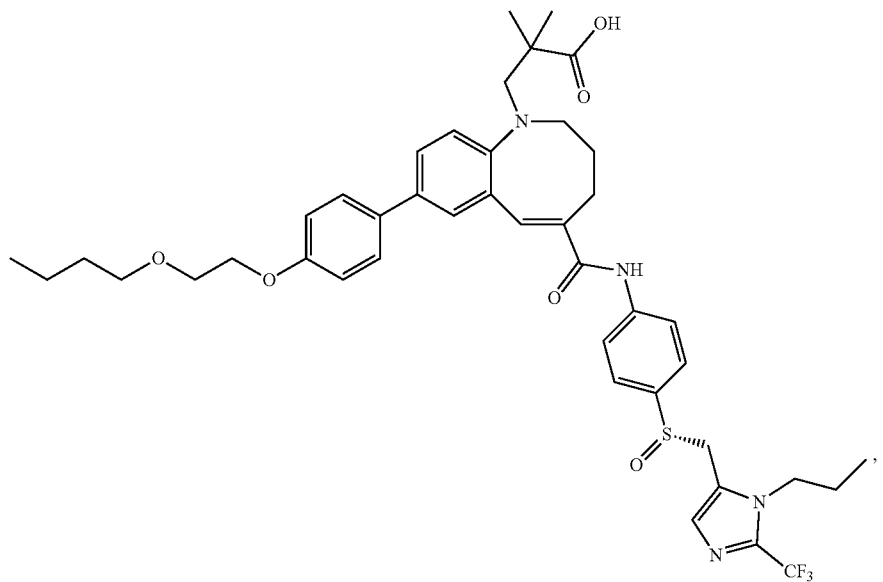
27

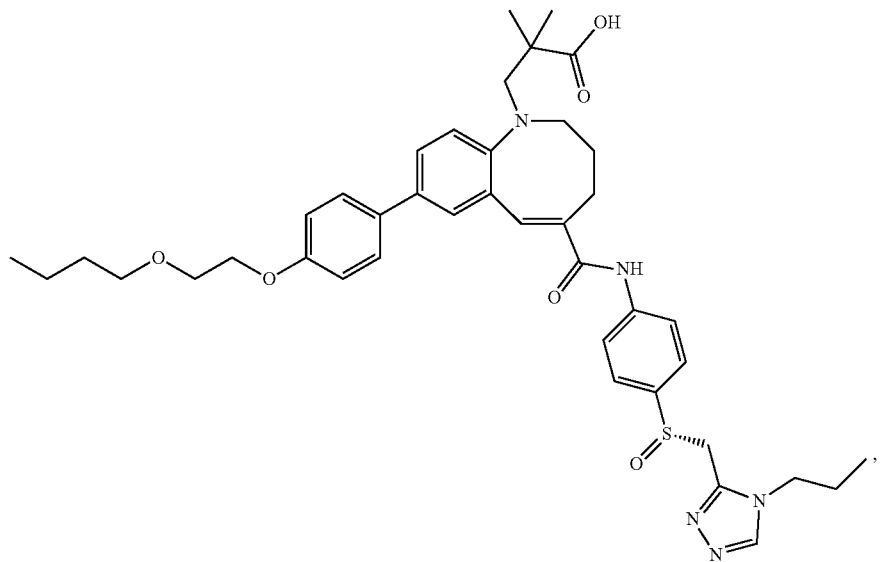
28
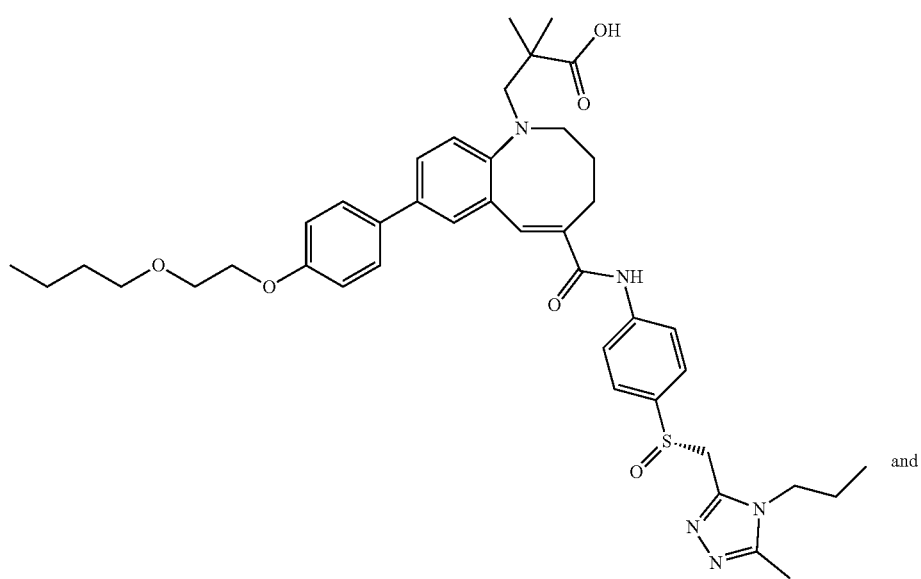
29
and

-continued

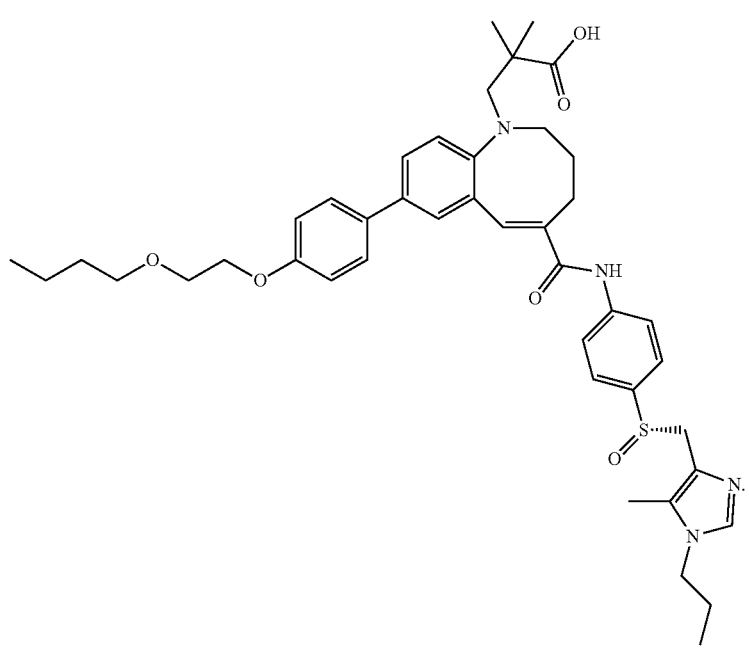

An atom in the compound of the invention may be replaced by its isotopes. For example, $^{12}C$ may be replaced by its isotope $^{13}C$ or $^{14}C$; $^{1}H$ may be replaced by $^{2}H$ (D, deuterium) or $^{3}H$ (T, tritium), and so on. The invention includes an isotope-labeled compound obtained by replacing any atom in the compound with its isotope.

The present application also relates to a process for the preparation of a compound of formula I, comprising the following synthetic route:

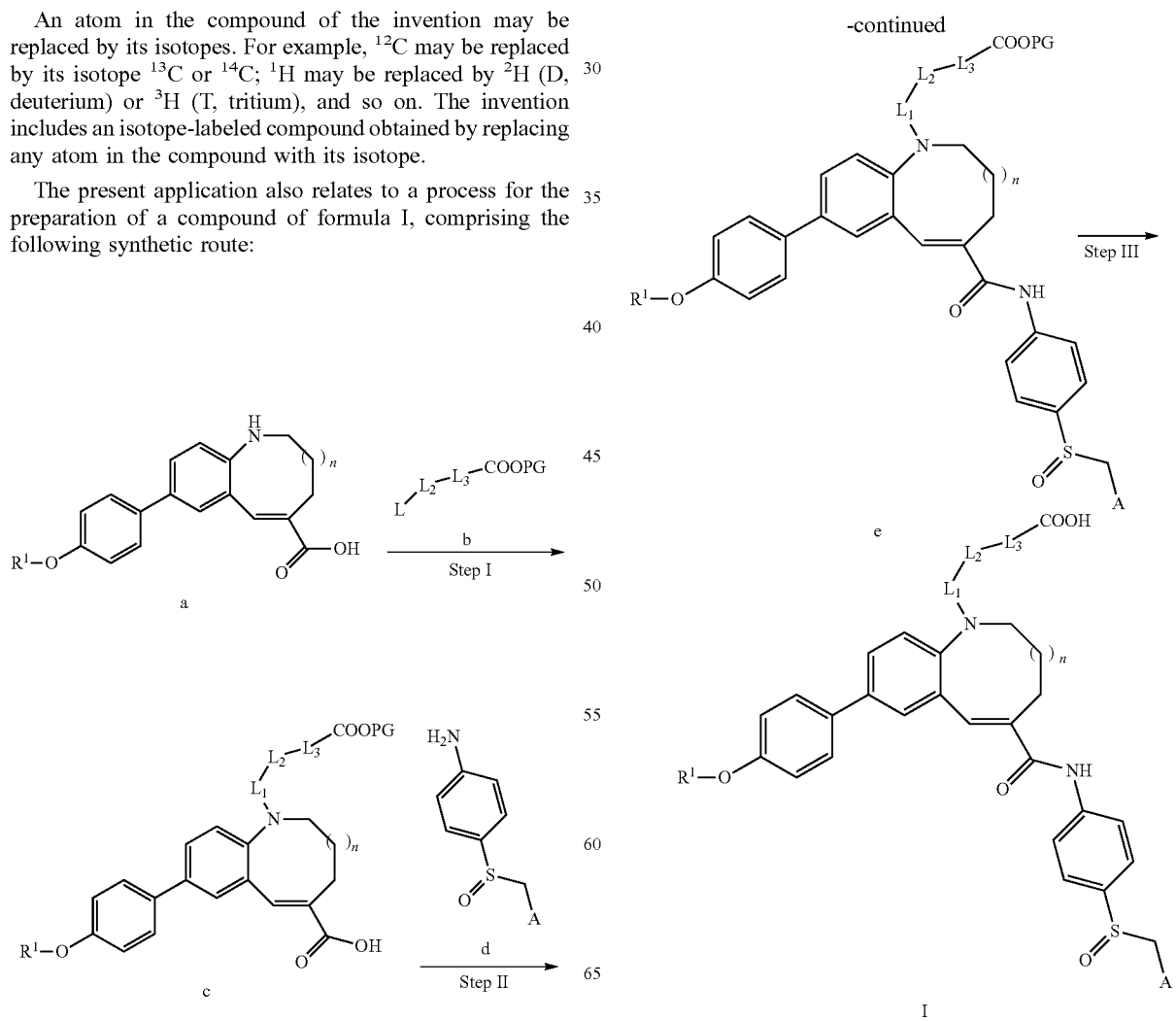

wherein $R^1$, n, $L_1$, $L_2$, $L_3$ or A is as defined above, Lisa group bearing an aldehyde group at the end, and L may be converted to $L_1$ (preferably, $L_1$ is $C_{1-3}$ alkylene, and more preferably, $L_1$ is selected from methylene and ethylene) after reactions, and the carboxyl protection group PG is selected from the following groups that are optionally substituted with one or more $R^7$: $C_{1-6}$ alkyl, $C_{2-6}$ alkenyl, $C_{2-6}$ alkynyl, $C_{3-10}$ cycloalkyl, $C_{3-10}$ heterocycloalkyl, $C_{6-10}$ aryl, $C_{1-6}$ alkylene-$C_{6-10}$ aryl, $C_{5-12}$ heteroaryl, $R^7$ is selected from hydrogen, deuterium, halogen, $C_{1-6}$ alkyl and $C_{1-6}$ alkoxy. In some preferred embodiments, the carboxyl protection group PG is preferably $C_{1-6}$ alkyl.

Particularly, the process comprises the following steps:

Step I: Reacting Compound a with Compound b to Provide Compound c:

the reaction is preferably carried out in a suitable organic solvent, and said organic solvent may be selected from a linear or cyclic ether (e.g. tetrahydrofuran or diethyl ether), a halogenated hydrocarbon (e.g. dichloromethane, chloroform, 1,2-dichloroethane or the like), a nitrile (e.g. acetonitrile or the like), N-methylpyrrolidone, dimethylformamide, dimethylacetamide, 1,4-dioxane, dimethylsulfoxide and any combination thereof, preferably dioxane or 1,2-dichloroethane. The reaction is preferably carried out in the presence of a suitable reducing agent, and said reducing agent is selected from sodium borohydride, potassium borohydride, sodium cyanoborohydride and sodium borohydride acetate, preferably the reducing agent is sodium cyanoborohydride. The reaction is preferably carried out under suitable acidic condition, and said acid may be selected from hydrochloric acid, acetic acid and trifluoroacetic acid, preferably the acid is trifluoroacetic acid. The reaction is preferably carried out at a suitable temperature, and said temperature is preferably from −50 to 100° C., more preferably from −20 to 70° C. The reaction is preferably carried out for a suitable time, for example 1 to 24 hours, and for example 1 to 6 hours.

Step II: Reacting Compound c with Compound d to Provide Compound e.

The reaction is preferably carried out in a suitable organic solvent, and said organic solvent may be selected from a halogenated hydrocarbon (e.g., dichloromethane, chloroform, 1,2-dichloroethane or the like), a nitrile (e.g., acetonitrile or the like), N-methylpyrrolidone, dimethylformamide, dimethylacetamide, 1,4-dioxane, dimethylsulfoxide, and any combination thereof, preferably dichloromethane. The reaction is preferably carried out in the presence of a suitable condensing agent, and the condensing agent may be selected from thionyl chloride, oxalyl chloride, phosphorus oxychloride, phosphorus trichloride, phosphorus pentachloride, ethyl chloroformate, isopropyl chloroformate, HATU, HBTU, EEDQ, DEPC, DCC, DIC, EDC, BOP, PyAOP or PyBOP, preferably the condensing agent is thionyl chloride, oxalyl chloride. The reaction is preferably carried out under suitable basic condition; the base is an organic or inorganic base; preferably, the organic base is selected from triethylamine, DIPEA, pyridine, NMM or DMAP, and preferably, the inorganic base is selected from NaH, NaOH, $Na_2CO_3$ or $K_2CO_3$; preferably, the base is selected from triethylamine, DIPEA and DMAP. The reaction is preferably carried out at a suitable temperature, and the reaction temperature is preferably from 0 to 100° C., more preferably from 15 to 50° C. The reaction is preferably carried out for a suitable time, for example 1 to 24 hours, and for example 2 to 7 hours.

Step III: Removing the Protection Group of Compound e to Provide a Compound of General Formula I.

The reaction is preferably carried out in suitable water and/or an organic solvent, and the organic solvent may be selected from a halogenated hydrocarbon (e.g. dichloromethane, chloroform, 1,2-dichloroethane or the like), a nitrile (e.g. acetonitrile or the like), an alcohol (e.g. methanol, ethanol), an ether (e.g. tetrahydrofuran, dioxane), N-methylpyrrolidone, dimethylformamide, dimethylacetamide, dimethylsulfoxide and any combination thereof, preferably water and ethanol. The reaction is preferably carried out under suitable acidic condition, and the acid is hydrochloric acid, sulfuric acid or trifluoroacetic acid. The reaction is preferably carried out under suitable basic condition, and the base is sodium hydroxide, potassium hydroxide, sodium carbonate, potassium carbonate or cesium carbonate, preferably the base is selected from sodium hydroxide. The reaction is preferably carried out at a suitable temperature, and the reaction temperature is preferably from −20 to 100° C., more preferably 0 to 60° C. The reaction is preferably carried out for a suitable time, for example 1 to 24 hours.

The application also relates to a process for the preparation of a compound of formula $I_a$:

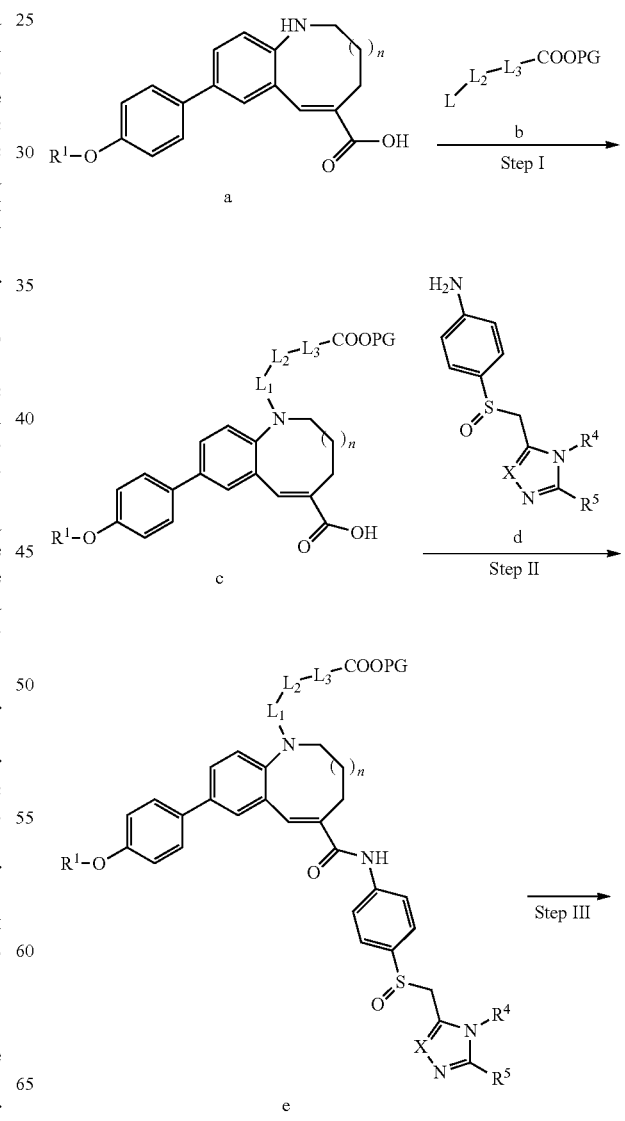

-continued

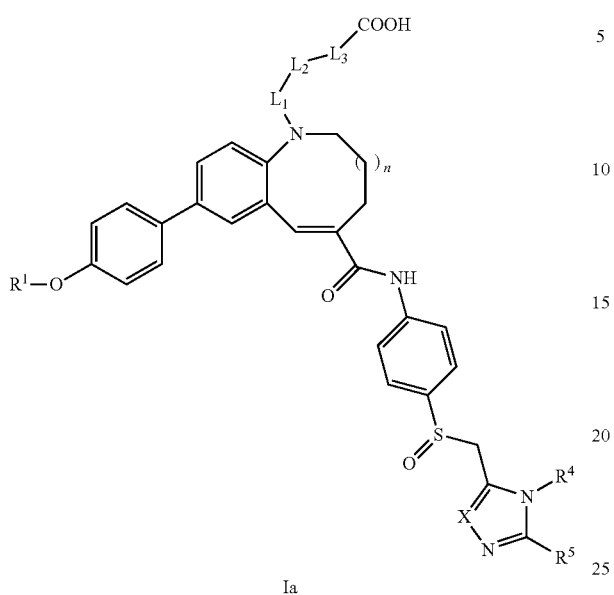

Ia wherein $R^1$, $R^4$, $R^5$, n, $L_1$, $L_2$, $L_3$, PG and X are as defined above, L is a group bearing an aldehyde group at the end, and L may be converted to $L_1$ (preferably, $L_1$ is $C_{1-3}$ alkylene, and more preferably, $L_1$ is selected from methylene and ethylene), the process for the preparation of the compound of formula $I_a$ refers to the process for the preparation of the compound of formula I.

The application also relates to a process for the preparation of a compound of formula $I_b$:

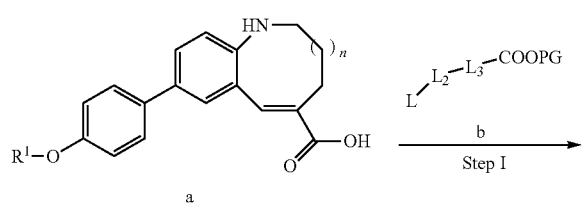

a

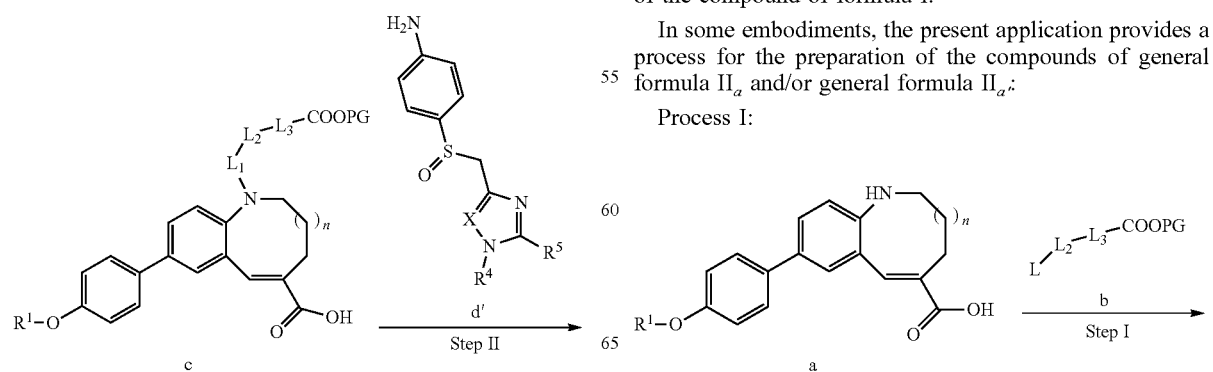

-continued

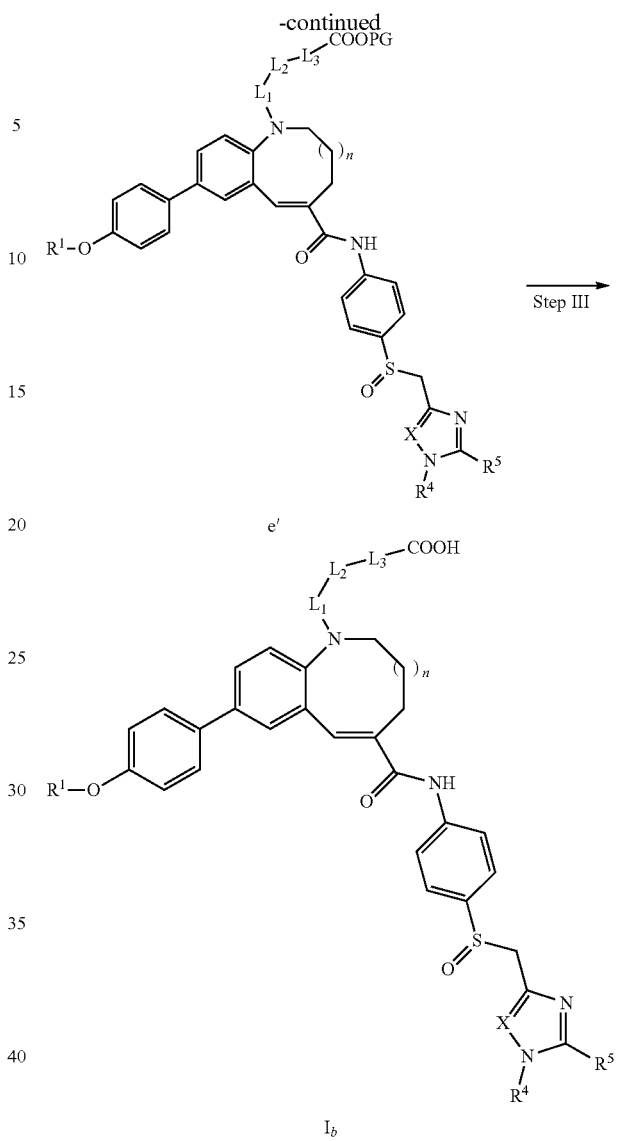

$I_b$ wherein $R^1$, $R^4$, $R^5$, n, $L_1$, $L_2$, $L_3$, PG and X are as defined above, L is a group bearing an aldehyde group at the end, and L may be converted to $L_1$ (preferably, $L_1$ is $C_{1-3}$ alkylene, and more preferably, $L_1$ is selected from methylene and ethylene), the process for the preparation of the compound of formula $I_b$ refers to the process for the preparation of the compound of formula I.

In some embodiments, the present application provides a process for the preparation of the compounds of general formula $II_a$ and/or general formula $II_a$:

Process I:

Process II:

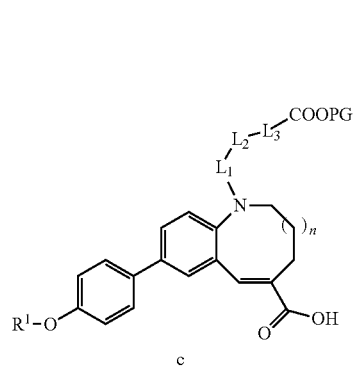
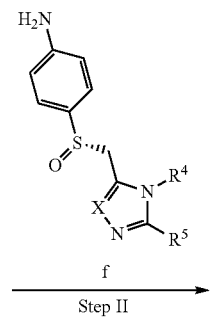
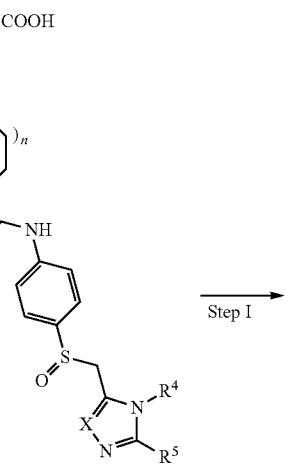
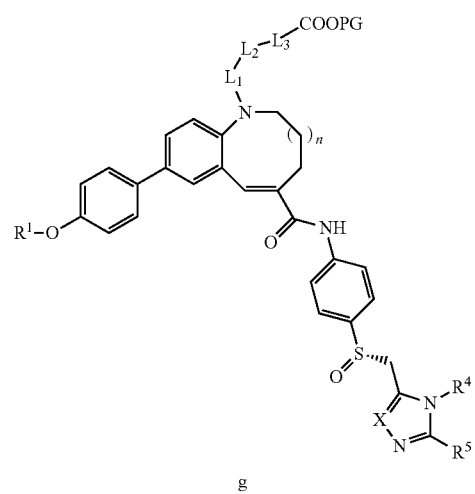

wherein $R^1$, $R^4$, $R^5$, n, $L_1$, $L_2$, $L_3$, PG and X are as defined above, L is a group bearing an aldehyde group at the end, and L may be converted to $L_1$ (preferably, $L_1$ is $C_{1-3}$ alkylene, and more preferably, $L_1$ is selected from methylene and ethylene).

The synthetic steps of the process refer to the steps for the synthesis of the compound of formula $I_a$.

wherein $R^1$, $R^4$, $R^5$, n, $L_1$, $L_2$, $L_3$ and X are as defined above.

In particular, Process II comprises the following steps:

Step I: Separating the Compound of Formula $I_a$ to Provide the Compounds of General Formula $II_a$ and General Formula $II_{a'}$.

The separation may be applied by using a commercially available chiral preparative column, preferably OD, OJ, AS, AD, IA, IB, IC, ID, etc. with an alcohol (ethanol, isopropanol or the like), a weak polar solvent (n-hexane, petroleum ether, $CO_2$ or the like), a cosolvent (dichloromethane or the like) and a base (ammonia water, diethylamine or the like) as the mobile phase to perform separations and purifications, and ingredients having ee value of >99% are collected.

Process III:

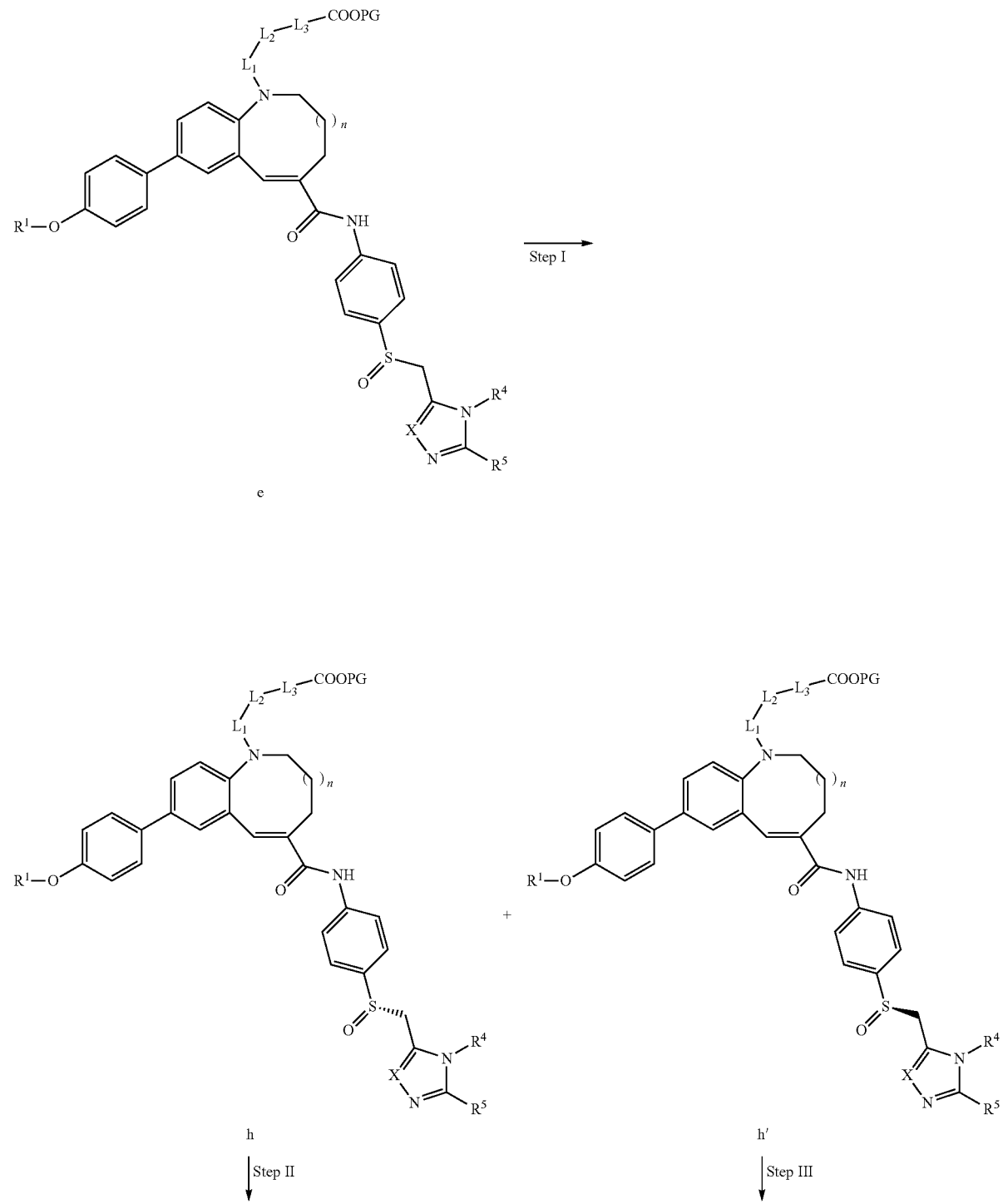

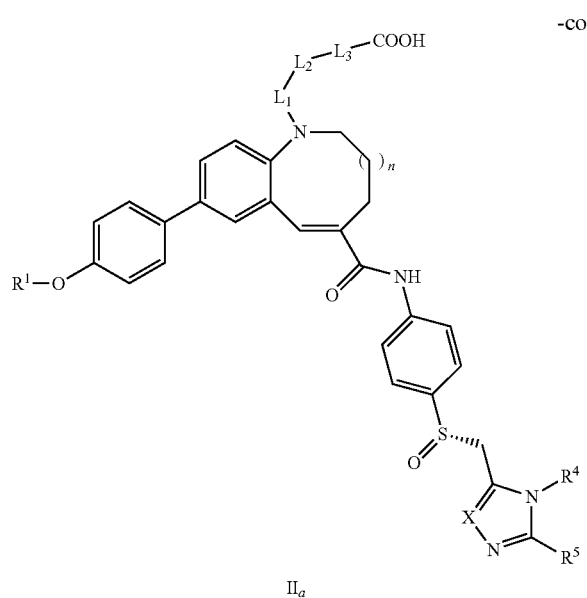

II$_a$

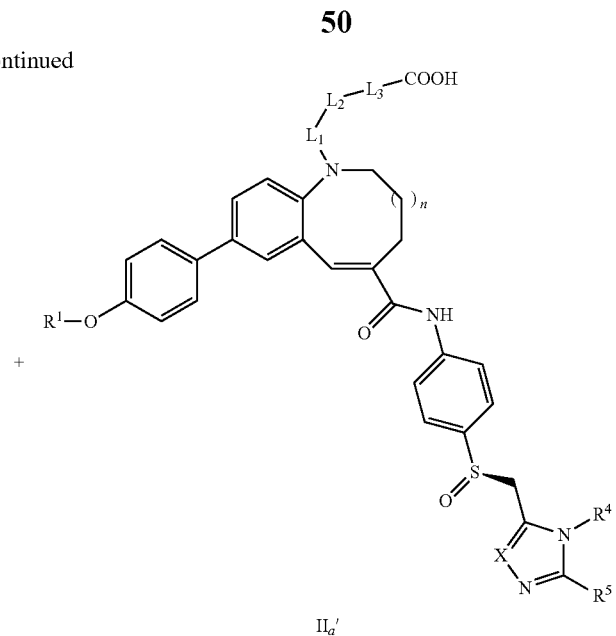

II$_a$' wherein R$^1$, R$^4$, R$^5$, n, L$_1$, L$_2$, L$_3$ and X are as defined above.

In particular, Process III comprises the following steps:

Step I: Separating Compound e to Provide Compound h and Compound h':

The method is applied by using a commercially available chiral preparative column, preferably OD, OJ, AS, AD, IA, IB, IC, ID, etc. with an alcohol (ethanol, isopropanol or the like), a weak polar solvent (n-hexane, petroleum ether, CO$_2$ or the like), a cosolvent (dichloromethane or the like) and a base (ammonia water, diethylamine or the like) as the mobile phase to perform separations and purifications, and ingredients having ee value of >99% are collected.

Step II: Removing the Protection Groups of Compound h and Compound h' to Respectively Provide Compounds of General Formula II$_a$ and General Formula II$_{a'}$:

The reaction is preferably carried out in suitable water and/or an organic solvent, and the organic solvent may be selected from a halogenated hydrocarbon (e.g. dichloromethane, chloroform, 1,2-dichloroethane or the like), a nitrile (e.g. acetonitrile or the like), an alcohol (e.g. methanol, ethanol), an ether (e.g. tetrahydrofuran, dioxane), N-methylpyrrolidone, dimethylformamide, dimethylacetamide, dimethylsulfoxide and any combination thereof, preferably water and ethanol. The reaction is preferably carried out under suitable acidic condition, and the acid is hydrochloric acid, sulfuric acid or trifluoroacetic acid. The reaction is preferably carried out under suitable basic condition, and the base is sodium hydroxide, potassium hydroxide, sodium carbonate, potassium carbonate or cesium carbonate, preferably the base is selected from sodium hydroxide. The reaction is preferably carried out at a suitable temperature, and the reaction temperature is preferably from −20 to 100° C., more preferably 0 to 60° C. The reaction is preferably carried out for a suitable time, for example 1 to 24 hours.

In some embodiments, the present application provides a process for the preparation of a compound of general formula II$_b$ and/or general formula comprising the following steps:

Process I:

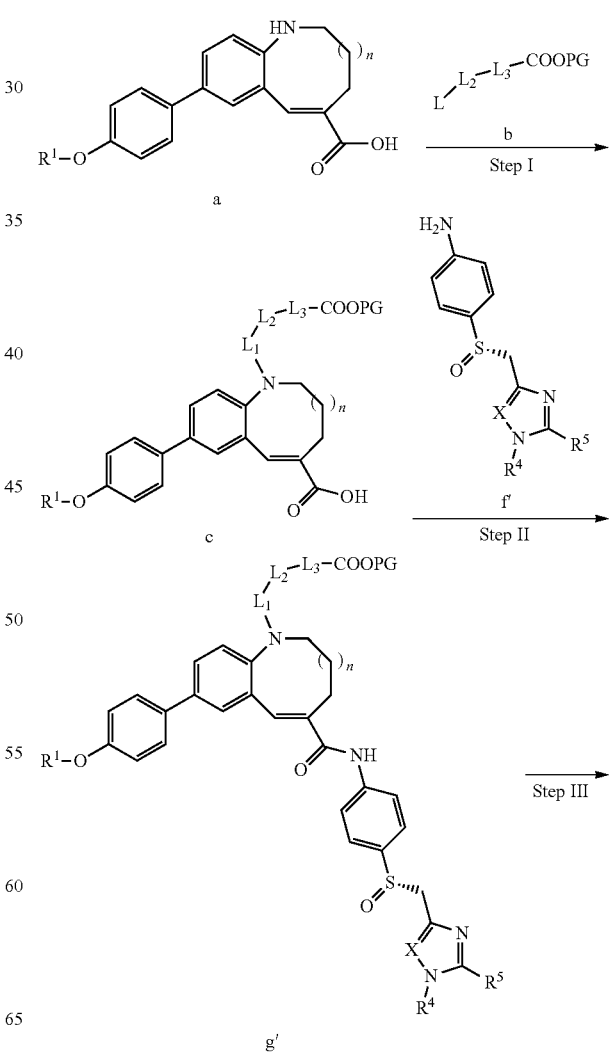

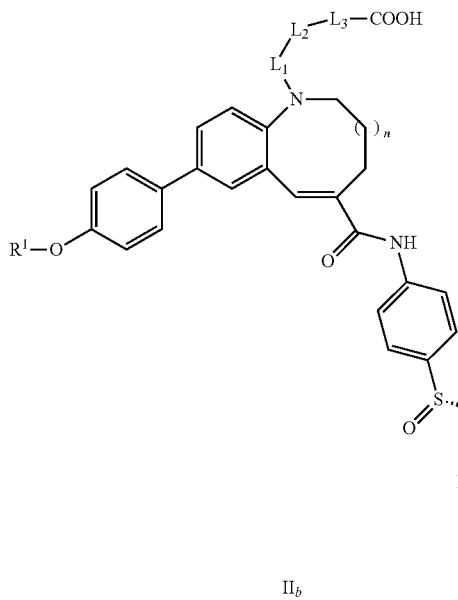

II$_b$ wherein $R^1$, $R^4$, $R^5$, n, $L_1$, $L_2$, $L_3$, PG and X are as defined above, L is a group bearing an aldehyde group at the end, and L may be converted to $L_1$ (preferably, $L_1$ is $C_{1-3}$ alkylene, and more preferably, $L_1$ is selected from methylene and ethylene).

The synthetic steps of the process refer to the steps for the synthesis of the compound of general formula I$_b$.

Process II:

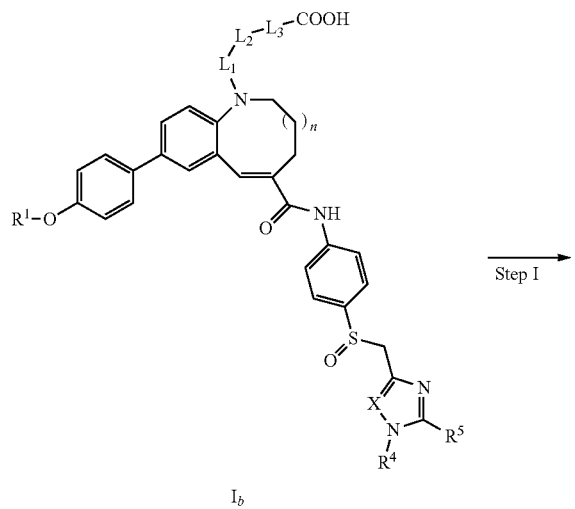

I$_b$ $\xrightarrow{\text{Step I}}$

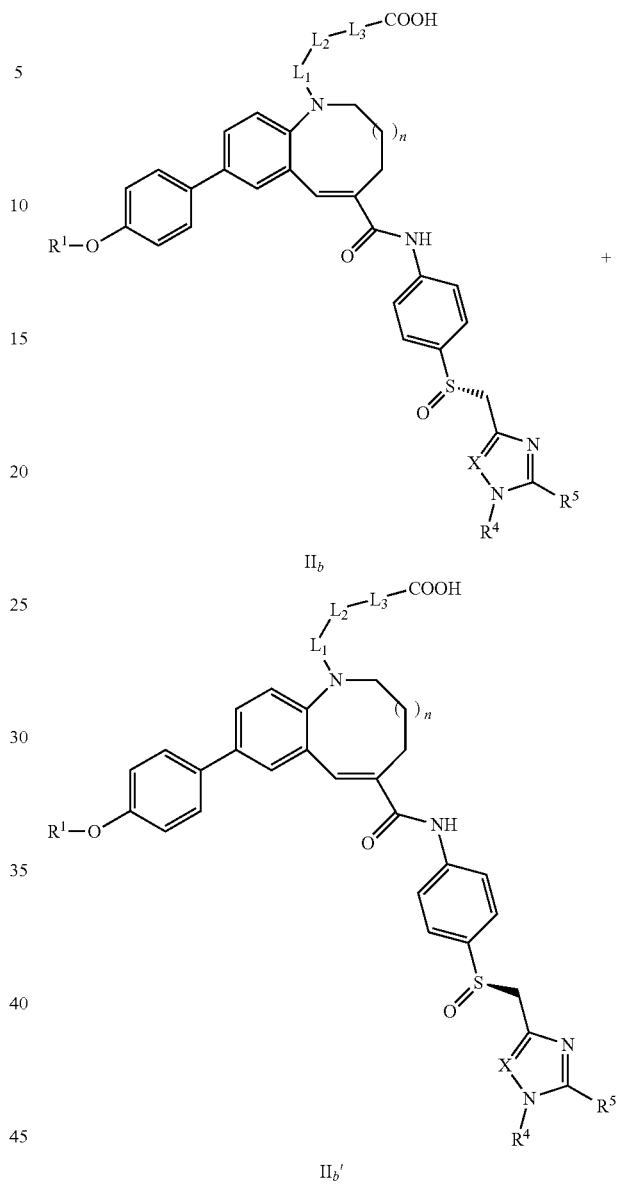

II$_b$

+

II$_b'$ wherein $R^1$, $R^4$, $R^5$, n, $L_1$, $L_2$, $L_3$ and X are as defined above.

In particular, Process II comprises the following steps:

Step I: Separating the Compound of Formula I$_b$ to Provide the Compounds of the Formula II$_b$ and II$_b'$.

The separation is applied by using a commercially available chiral preparative column, preferably OD, OJ, AS, AD, IA, IB, IC, ID, etc. with an alcohol (ethanol isopropanol or the like), a weak polar solvent (n-hexane, petroleum ether, $CO_2$ or the like), a cosolvent (dichloromethane or the like) and a base (ammonia water, diethylamine or the like) as the mobile phase to perform separations and purifications, and ingredients having ee value of >99% are collected.

In another aspect, the present application provides a pharmaceutical composition, comprising the compound of the first aspect or a pharmaceutically acceptable salt, ester, solvate (e.g., hydrate), stereoisomer, tautomer, prodrug thereof, or crystalline form, metabolite thereof, or a mixture of the aforementioned, and one or more pharmaceutically acceptable carriers.

In some preferred embodiments, the pharmaceutical composition is in a form of tablets, capsules, lozenges, hard candies, powder, sprays, creams, ointments, suppositories, gels, pastes, lotions, ointments, aqueous suspensions, injectable solutions, elixirs and syrups.

In some preferred embodiments, the pharmaceutical composition further comprises one or more other drugs that prevent or treat a CCR2- and/or CCR5-mediated disease or condition, especially nonalcoholic fatty liver disease (NAFLD) or the like.

In a further aspect, the present application provides a pharmaceutical formulation, comprising the compound of the first aspect or a pharmaceutically acceptable salt, ester, solvate (e.g., hydrate), stereoisomer, tautomer, prodrug thereof, or crystalline form, metabolite thereof, or a mixture of the aforementioned, or said composition, and one or more pharmaceutically acceptable carriers.

In a further aspect, the present application provides a kit product, comprising:
a) a first container, comprising, as a first therapeutic agent, at least one compound of the first aspect or a pharmaceutically acceptable salt, ester, solvate (e.g., hydrate), stereoisomer, tautomer, prodrug thereof, or crystalline form, metabolite thereof, or a mixture of the aforementioned, or, as a first pharmaceutical composition, the pharmaceutical composition;
b) an optional second container, comprising, as a second therapeutic agent, at least one other therapeutic agent, or as a second pharmaceutical composition, a pharmaceutical composition comprising said other therapeutic agent; and
c) an optional packaging specification.

In some preferred embodiments, the other therapeutic agent is selected from drugs, other than the compounds described in this disclosure, that are useful in the prevention or treatment of a CCR2- and/or CCR5-mediated disease or condition, especially nonalcoholic fatty liver diseases (NAFLD) or the like.

In another aspect, the present application provides use of the compound of the first aspect or a pharmaceutically acceptable salt, ester, solvate (e.g., hydrate), stereoisomer, tautomer, prodrug thereof, or crystalline form, metabolite thereof, or a mixture of the aforementioned, the pharmaceutical composition, the pharmaceutical formulation or the kit product, in the manufacture of a medicament for the prevention or treatment of a CCR2- and/or CCR5-mediated disease or condition, especially nonalcoholic fatty liver diseases (NAFLD) or the like.

In another aspect, the present application provides the compound of the first aspect or a pharmaceutically acceptable salt, ester, solvate (e.g., hydrate), stereoisomer, tautomer, prodrug thereof, or crystalline form, metabolite thereof, or a mixture of the aforementioned, the pharmaceutical composition, the pharmaceutical formulation or the kit product, for use in the prevention or treatment of a CCR2- and/or CCR5-mediated disease or condition, especially nonalcoholic fatty liver disease (NAFLD) or the like.

In another aspect, the present application provides a method for the prevention or treatment of a CCR2- and/or CCR5-mediated disease or condition, especially nonalcoholic fatty liver disease (NAFLD) or the like, comprising administering to an individual in need thereof a therapeutically effective amount of the compound or a pharmaceutically acceptable salt, ester, solvate (e.g., hydrate), stereoisomer, tautomer, prodrug thereof, or crystalline form, metabolite thereof, or a mixture of the aforementioned, the pharmaceutical composition, the pharmaceutical formulation or the kit product, and optionally further comprising administering to the individual in need thereof with another drug that are used for the prevention or treatment of a CCR2- and/or CCR5-mediated disease or condition, especially nonalcoholic fatty liver disease (NAFLD) or the like.

In the present application, a subject of the pharmaceutical composition is to promote the administration to an organism, or to facilitate the absorption of active ingredients thereby exerting biological activity. The carrier includes, but are not limited to, an ion exchanger, aluminum oxide, aluminum stearate, lecithin, a serum protein such as human serum albumin, a buffer substance such as a phosphate, glycerol, sorbic acid, potassium sorbate, a mixture of partial glycerides of saturated vegetable fatty acids, water, a salt or an electrolyte such as protamine sulfate, disodium hydrogen phosphate, potassium hydrogen phosphate, sodium chloride, a zinc salt, colloidal silica, magnesium trisilicate, polyvinylpyrrolidone, a cellulosic substance, polyethylene glycol, sodium carboxymethylcellulose, polyacrylates, beeswax, lanolin.

The present application provides that the compound according to the first aspect or a pharmaceutically acceptable salt, ester, solvate (e.g., hydrate), stereoisomer, tautomer, prodrug thereof, or crystalline form, metabolite thereof, or a mixture of the aforementioned, pharmaceutical compositions, pharmaceutical formulations or kits may be administered by the following routes: parenteral, topical, intravenous, oral, subcutaneous, intraarterial, intradermal, transdermal, rectal, intracranial, intraperitoneal, intranasal, and intramuscular routes or as an inhalant. Optionally, the pharmaceutical composition may be administered in combination with other reagents that have at least some effect in the treatment of various diseases.

The present application provides the compound according to the first aspect or a pharmaceutically acceptable salt, ester, solvate (e.g., hydrate), stereoisomer, tautomer, prodrug thereof, or crystalline form, metabolite thereof, or a mixture of the aforementioned or the pharmaceutical composition may be formulated into various suitable dosage forms depending on the administration route.

The pharmaceutical composition or the suitable dosage form described in the present application may contain from 0.01 mg to 1000 mg of the compound.

For oral administration, the compound or a pharmaceutically acceptable salt, ester, solvate (e.g., hydrate), stereoisomer, tautomer, prodrug thereof, or crystalline form, metabolite thereof, or a mixture of the aforementioned or pharmaceutical compositions may be formulated into any orally acceptable preparation forms, including, but not limited to, tablets, capsules, aqueous solutions or aqueous suspensions. Among them, carriers used in tablets generally include lactose and corn starch, additionally, lubricants such as magnesium stearate may also be added. Diluents used in capsules generally include lactose and dried corn starch. For aqueous suspensions, active ingredients are usually used by mixing with suitable emulsifiers and suspending agents. Optionally, sweeteners, flavoring agents or coloring agents may be further added into the above oral preparations.

For skin tropical administration, the compound or a pharmaceutically acceptable salt, ester, solvate (e.g., hydrate), stereoisomer, tautomer, prodrug thereof, or crystalline form, metabolite thereof, or a mixture of the aforementioned or the pharmaceutical composition may be formulated into suitable ointments, lotions or creams, wherein active ingredients are suspended or dissolved in one or more carriers. The carriers used in ointments include, but are not limited to, mineral oil, liquid petrolatum, white petrolatum, propylene glycol, polyethylene oxide, polypropylene oxide, emulsifying wax and water; carriers used in lotions or creams include, but are not limited to, mineral oil, sorbitan monostearate Tween 60, cetyl ester wax, hexadecene aromatic alcohol, 2-octyldodecanol, benzyl alcohol and water.

The compound or a pharmaceutically acceptable salt, ester, solvate (e.g., hydrate), stereoisomer, tautomer, prodrug thereof, or crystalline form, metabolite thereof, or a mixture of the aforementioned or the pharmaceutical composition may also be administered in the form of sterile injection preparations, including sterile injection water, oily suspensions or sterile injection solutions. Among them, useful carriers and solvents include water, a Ringer's solution and an isotonic sodium chloride solution. In addition, sterile non-volatile oils may also be used as a solvent or a suspending medium, such as mono-glycerides or di-glycerides.

In the embodiments of the present application, suitable in vitro or in vivo assays are performed to determine the efficacy of the pharmaceutical composition and if the administrations are suitable for the treatment of an individual suffering from the disease or states. Examples of these assays are described in following non-limiting examples in connection with specific diseases or medical treatments. Typically, an effective amount of the pharmaceutical composition sufficient to achieve preventive or therapeutic effects is about 0.001 mg/kg body weight/day to about 10,000 mg/kg body weight/day. Suitably, the dose is from about 0.01 mg/kg body weight/day to about 1000 mg/kg body weight/day. The dose may be in a range of about 0.01 to 1000 mg/kg body weight of a subject, more typically, 0.1 to 500 mg/kg body weight of a subject, every day, every two days or every three days. Exemplary therapeutic regimen includes once administration every two days or once administration every week or once administration every month. The preparations are typically administered many times, and the interval of a single dose may be one day, one week, one month or one year. Alternatively, the preparations may be administered in a form of sustained release preparation, and in this case, a low administration frequency is required. The dose and the frequency may vary according to the half-life of the preparations in the subject or the treatment is prophylactical or therapeutic. In prophylactical applications, a relatively low dose is administered in a low interval frequency. In therapeutic applications, sometimes, a relatively high dose have to be administrated in a relatively short interval until the progress of diseases is delayed or halted, preferably until an individual exhibits partial or full improvements in disease symptoms, and thereafter, a preventive regimen may be administrated to the patient.

Unless otherwise defined below, all the technical terms and scientific terms used herein are intended to have the same meaning as commonly understood by a person skilled in the art. The mentioned technologies herein are intended to refer those commonly understood in the art, including variations that are obvious for a person skilled in the art and equivalent substitutions. Even though the following terms are believed to be well understood by a person skilled in the art, they are still defined herein for better explanation of the invention.

As used herein, the terms "include", "comprise", "have", "contain", or "relate" and other variations thereof herein, are inclusive or open and do not exclude other not specified elements or method steps.

As used herein, the term "alkyl" is defined as a straight-chain or branched aliphatic hydrocarbon group. In some embodiments, the alkyl has 1 to 8, such as 1 to 4, carbon atoms. For example, as used herein, the term "$C_{1-6}$ alkyl" refers to the straight-chain or branched group having 1 to 6 carbon atoms (e.g., methyl, ethyl, n-propyl, isopropyl, n-butyl, isobutyl, sec-butyl, tert-butyl, n-pentyl, or n-hexyl), which is optionally substituted with one or more (such as 1 to 3) suitable substituents such as halogen (referred to as "haloalkyl", such as $-CF_3$, $-C_2F_5$, $-CHF_2$, $-CH_2F$, $-CH_2CF_3$, $-CH_2Cl$, $-CH_2CH_2CF_3$, etc.).

As used herein, the term "alkylene" is defined as a saturated divalent hydrocarbyl group derived from a straight-chain or branched saturated hydrocarbyl group by removing two hydrogen atoms, and the alkylene group contains 1-10 carbon atoms, 1-6 carbon atoms, 1-4 carbon atoms, or 1-3 carbon atoms, such as methylene ($-CH_2-$), ethylene ($-CH_2CH_2-$), isopropylene ($-CH(CH_3)CH_2-$) or the like, wherein the alkylene group may be independently unsubstituted or substituted with one or more substituents described in the invention.

As used herein, the term "cycloalkyl" refers to a saturated or unsaturated, non-aromatic, monocyclic or polycyclic (such as bicyclic) hydrocarbon ring (e.g., monocycles, such as cyclopropyl, cyclobutyl, cyclopentyl, cyclohexyl, cycloheptyl, cyclooctyl, cyclononyl, or bicycles, including spiro, fused or bridged systems (such as bicyclo[1.1.1]pentyl, bicyclo[2.2.1]heptyl or the like), which is optionally substituted with one or more (such as 1 to 3) suitable substituents. The cycloalkyl group has 3 to 15, for example, 3 to 10 carbon atoms, 3 to 7 carbon atoms, or 3 to 6 carbon atoms. For example, as used herein, the term "$C_{3-7}$ cycloalkyl" refers to a saturated or unsaturated, non-aromatic, monocyclic or polycyclic (such as bicyclic) hydrocarbon ring having 3 to 7 ring-forming carbon atoms (e.g., cyclopropyl, cyclobutyl, cyclopentyl, cyclohexyl, cycloheptyl), which is optionally substituted with one or more (such as 1 to 3) suitable substituents, for example methyl-substituted cyclopropyl.

As used herein, the term "$C_{3-10}$ cycloalkylene" is defined as a divalent $C_{3-10}$ alkyl residue, for example divalent methylene residue, such as cyclopropylene, cyclobutylene, cyclopentylene, cyclohexylene, cycloheptylene or cyclooctylene, such as cyclopropylene, cyclobutylene, cyclopentylene, cyclohexylene, and particularly cyclopentylene, cyclohexylene.

As used herein, the term "alkoxy" refers to a linear, branched or cyclic saturated monovalent hydrocarbon group having the formula of $-O$-alkyl, wherein the term "alkyl" is as defined above or it is a "cycloalkyl" as defined below, e.g. $C_{1-6}$ alkyl, $C_{1-3}$ alkyl or $C_{3-6}$ cycloalkyl, such as methoxy, ethoxy, n-propoxy, isopropoxy, cyclopropoxy, n-butoxy, isobutoxy, t-butoxy, sec-butoxy, cyclobutoxy, pentyloxy, isopentyloxy or n-hexyloxy, or their isomers.

As used herein, the term "heterocyclyl" refers to a saturated or unsaturated, monocyclic or bicyclic group which contains 2, 3, 4, 5, 6, 7, 8 or 9 carbon atoms in the ring and one or more (e.g., one, two, three or four) heteroatom-containing groups selected from $C(=O)$, O, S, $S(=O)$, $S(=O)_2$ and $NR^a$, wherein $R^a$ represents hydrogen atom, $C_{1-6}$ alkyl or halogenated $C_{1-6}$ alkyl; the heterocycloalkyl may be connected to the rest moiety of the molecule via any one of the carbon atoms or the nitrogen atom (if any). For example, $C_{3-6}$ heterocyclyl, $C_{5-6}$ heterocyclyl or $C_{3-7}$ heterocyclyl are the heterocyclyl having 3-6, 5-6 or 3-7 carbon atoms. 3- to 10-membered heterocyclyl is the group having 3 to 10 carbon atoms and heteroatoms in the ring, and 4- to 7-membered heterocyclyl is the group having 4 to 7 carbon atoms and heteroatoms in the ring, for example, but it is not limited to, oxiranyl, aziridinyl, azetidinyl, oxyethanyl, tetrahydrofuranyl, dioxolinyl, pyrrolidinyl, pyrrolidinonyl, imidazolidinyl, pyrazolinyl, pyrrolinyl, tetrahydropyranyl, piperidinyl, morpholinyl, dithianyl, thiomorpholinyl, piperazinyl or trithianyl.

As used herein, the term "heteroarylene" refers to divalent heteroaryl group, e.g., having 5-12, 5-10, or 5-8 carbon atoms.

As used herein, the term "aryl" refers to a full-carbon monocyclic or fused polycyclic aromatic group having a conjugated π-electron system. For example, as used herein, the term "$C_{6-10}$ aryl" is intended to refer to an aromatic group containing 6 to 10 carbon atoms, such as phenyl or naphthyl. The aryl is optionally substituted with one or more (such as 1 to 3) suitable substituents.

As used herein, the term "arylene" refers to an aryl group having two unsaturated valences, and having, e.g., 6-10 or 6-8 carbon atoms, for example, phenylene.

As used herein, the term "heteroaryl" refers to a monocyclic, bicyclic or tricyclic aromatic ring system having 5, 6, 8, 9, 10, 11, 12, 13 or 14 ring atoms, for example 5-10 ring atoms, and in particular 1 or 2 or 3 or 4 or 5 or 6 or 9 or 10 carbon atoms, and comprising at least one heteroatom which may be identical or different (said heteroatom, for example, is oxygen, nitrogen or sulfur), additionally, in each occurrence, the group may be benzo-fused. In particular, the heteroaryl group is selected from thienyl, furyl, pyrrolyl, oxazolyl, thiazolyl, imidazolyl, pyrazolyl, isoxazolyl, isothiazolyl, oxadiazolyl, triazolyl, thiadiazolyl and their benzo derivatives; or pyridyl, pyridazinyl, pyrimidinyl, pyrazinyl, triazinyl and their benzo derivatives.

As used herein, the term "halo" or "halogen" group is defined to include F, Cl, Br or I.

As used herein, the term "alkenyl" refers to an aliphatic hydrocarbon group containing at least one carbon-carbon double bond and one hydrogen atom replaced by a bond. The alkenyl can be a straight-chain or branched, and it contains about 2 to about 15 carbon atoms. For example, the "$C_{2-6}$ alkenyl" herein contains about 2 to about 6 carbon atoms. Non-limiting examples of the alkenyl include ethenyl, propenyl, n-butenyl, 3-methyl-but-2-enyl, n-pentenyl, octenyl and decenyl. The alkenyl may be unsubstituted or substituted with one or more substituents that may be identical or different, each substituent is independently selected from halogen, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_{2-6}$ alkenyl" refers to an alkenyl group of 2 to 6 carbon atoms.

As used herein, the term "alkenylene" refers to a straight-chain or branched divalent hydrocarbon group for connecting the rest moiety of the molecule, which only consists of carbon and hydrogen atoms and contains at least one double bond and two to six carbon atoms, such as ethenylene, propenylene, n-butenylene or the like. The alkenylene chain is connected to the rest moiety of the molecule via a double or single bond and connected to a group via a double or single bond. The connection site of the alkenylene chain to the rest moiety of the molecular and the group may pass through one carbon atom or any two carbon atoms in the chain. Unless otherwise specified in the description, the alkenylene chain may be optionally substituted with one or more substituents independently selected from halo, cyano, nitro, aryl, cycloalkyl, heterocyclyl, heteroaryl, oxo, trimethylsilyl, —OR$^8$, —OC(=O)R$^8$, —N(R$^8$)$_2$, —C(=O)R$^8$, —C(=O)OR$^8$, —C(=O)N(R$^8$)$_2$, —N(R$^8$)C(=O)OR$^8$, —N(R$^8$)C(=O)R$^8$, —N(R$^8$)S(=O)$_t$R$^8$ (where t is 1 or 2), —S(=O)$_t$OR$^8$ (where t is 1 or 2), —S(=O)$_p$R$^8$ (where p is 0, 1 or 2), and —S(=O)$_t$N(R$^8$)$_2$ (where t is 1 or 2), wherein each R$^8$ is independently hydrogen, alkyl, haloalkyl, cycloalkyl, cycloalkylalky, aryl, arylalkyl, heterocyclyl, heterocyclylalkyl, heteroaryl, or heteroarylalkyl, and wherein each of the above substituents, as defined herein, may be optionally substituted.

As used herein, the term "alkynyl" refers to a hydrocarbon group having one or more C≡C triple bonds. The alkynyl has, but is not limited to, 2-18 carbon atoms, for example 2-10 carbon atoms, and for example 2-6 carbon atoms. The "lower alkynyl" herein refers to an alkynyl having less carbon atoms, for example, 2-8 carbon atoms, for example 2-6 carbon atoms, and for example 2-4 carbon atoms. Examples of the alkynyl herein include, but are not limited to, ethynyl, 2-propynyl, 2-butynyl, and 1,3-butynyl. When the alkynyl as defined herein involves a numerical range, for example "$C_2$-$C_6$ alkynyl" or "$C_{2-6}$ alkynyl", it refers to an alkynyl containing 2 carbon atoms, 3 carbon atoms, 4 carbon atoms, 5 carbon atoms, or 6 carbon atoms, and the alkynyl herein also encompasses instances, numerical ranges of which are not specified.

As used herein, the term "alkynylene" refers to the alkynyl as defined above in which one hydrogen atom has been replaced by a bond. Non-limiting examples of the alkynylene include —CH$_2$C≡C—, —CH$_2$C≡CCH$_2$— and —CH(CH$_3$)C≡C—, and for example, the alkynylene has 2 to 6 carbon atoms. The alkynylene is branched or straight. The term "$C_{2-6}$ alkynylene" refers to an alkynylene group having 2 to 6 carbon atoms, and the term "$C_{2-3}$ alkynylene" refers to an alkynylene group having 2 to 3 carbon atoms.

As used herein, the term "amino" refers to a nitrogen-containing moiety having two further substituents, wherein a chlorine or carbon atom is connected to the nitrogen. For example, representative amino groups include —NH$_2$, —NHCH$_3$, —N(CH$_3$)$_2$, —NHC$_{1-3}$ alkyl, —N(C$_{1-3}$ alkyl)$_2$ or the like. Unless otherwise specified, a compound of the invention containing an amino moiety may include a derivative thereof in which the amino moiety is protected. Suitable protecting groups of the amino moiety include acetyl, t-butyloxycarbonyl, benzyloxycarbonyl or the like.

As used herein, the term "carboxylic acid group," also known as "carboxyl" refers to a functional group having the chemical formula of —COOH. In the sense of the present invention, the term "carboxyl" further includes the related anion —COO— (carboxylate ion). Depending on environmental conditions, for example pH value of the environment, the functional group may be present in the form of —COOH or —COO—.

As used herein, the term "halogenated $C_{1-6}$ alkyl" refers to a group obtained from the $C_{1-6}$ alkyl as described above by substituting one or more (e.g., 1, 2, 3 or 4) hydrogen atoms with halogen (e.g., fluorine, chlorine, bromine, or iodine), for example, halogenated $C_{1-3}$ alkyl, halomethyl, haloethyl, halogenated $C_3$ alkyl, halogenated $C_4$ alkyl, fluoro $C_{1-3}$ alkyl, fluoromethyl, fluoroethyl, fluoro $C_3$ alkyl, fluoro $C_4$ alkyl, chloro $C_{1-3}$ alkyl, chloromethyl, chloroethyl, chloro $C_3$ alkyl, and chloro $C_4$ alkyl. Specific examples include, but are not limited to, fluoromethyl, difluoromethyl, trifluoromethyl, trifluoroethyl, chloroethyl or the like.

The term "substituted" refers to that one or more (e.g., one, two, three, or four) hydrogen atoms on an indicated atom are selectively replaced by indicated groups, provided that the normal valence of the indicated atom in current situations is not exceeded and the substitution can result in a stable compound. A combination of substituents and/or variables is permissible only when such a combination can result in a stable compound.

The term "optionally substituted" refers to an optional substitution with a specified group, radical or moiety.

In the case that the bond of a substituent is shown as passing through a bond connecting two atoms in a ring, such a substituent can be bonded to any ring-forming atom in the substitutable ring.

The compound of the invention may also comprise one or more (e.g., one, two, three, or four) isotopic replacements. For example, in said compound, H may be in any isotopic forms, including $^1H$, $^2H$ (D or deuterium), and $^3H$ (T or tritium); C may be in any isotopic forms, including $^{12}C$, $^{13}C$, and $^{14}C$; O may be in any isotopic forms, including $^{16}O$ and $^{18}O$.

The term "stereoisomer" refers to an isomer formed as a result of at least one asymmetric center. In a compound having one or more (e.g., one, two, three, or four) asymmetric centers, a racemate, a racemic mixture, a single enantiomer, a diastereomeric mixture and a single diastereomer may be formed. A specified individual molecule may also exist in the form of a geometric isomer (cis/trans). Similarly, the compound of the invention may be present as a mixture of two or more different structural forms in a rapid equilibrium (commonly referred to as tautomers). Representative examples of tautomers include ketone-enol tautomers, phenol-ketone tautomers, nitroso-oxime tautomers, imine-enamine tautomers or the like. It shall be understood that the scope of the present application encompasses all such isomers or mixtures in any ratios (e.g., 60%, 65%, 70%, 75%, 80%, 85%, 90%, 95%, 96%, 97%, 98%, 99%).

The present application encompasses all possible crystalline forms or polymorphs of the compound, and it may be a single polymorph polymorph or a mixture of more than one polymorphs in any ratios.

The compound or a pharmaceutically acceptable salt thereof may also form a solvate, such as an alcoholate or the like.

The compound may also be in the form of a prodrug or a form which would release the active ingredient after metabolism in vivo, may release the active ingredient. Selecting and preparing a suitable prodrug derivative is well-known techniques for a person skilled in the art.

The compound may also be in a chemically protected form. A protecting group can protect an active group (e.g. an amino group) of the compound, and the protecting group may be metabolized in vivo thus to release corresponding active ingredient. Selecting and preparing suitable chemically protected forms are well-known techniques for a person skilled in the art.

The term "pharmaceutically acceptable" as used in the present application refers to that a substance or composition has to be chemically and/or toxicologically compatible with other components that form a preparation and/or mammals to be treated with.

The term "pharmaceutically acceptable salt" as used in the present application includes a conventional salt formed with a pharmaceutically acceptable inorganic or organic acid, or inorganic or organic base. Illustrative examples of suitable salts include, but are not limited to, organic salts derived from amino acids such as glycine and arginine, ammonia, primary, secondary and tertiary amines, and cyclic amines such as piperidine, morpholine, and piperazine, and inorganic salts derived from sodium, calcium, potassium, magnesium, manganese, iron, copper, zinc, aluminum, and lithium.

It also should be understood that some compounds of the present application may be present in a free form or, when appropriate, in the form of a pharmaceutically acceptable derivative thereof. The pharmaceutically acceptable derivative includes, but is not limited to, a pharmaceutically acceptable salt, a solvate, a metabolite, or a prodrug, and all of which can directly or indirectly provide the compound, or a metabolite or residue thereof when being administered to a patient in need thereof.

The pharmaceutically acceptable salt of the compound includes an acid addition salt and a base addition salt. Suitable acid addition salts are formed from acids capable of forming non-toxic salts.

Suitable base addition salts are formed from bases capable of forming non-toxic salts. Acceptable inorganic bases include aluminum hydroxide and calcium hydroxide. Acceptable organic bases include tromethamine, N-methylglucamine or the like.

For reviews of suitable salts, please refer to Stahl and Wermuth, Handbook of Pharmaceutical Salts: Properties, Selection, and Use (Wiley-VCH, 2002). Methods for preparing pharmaceutically acceptable salts of the compounds are known for a person skilled in the art.

The compound may be present in a form of a hydrate or a solvate, wherein the compound of the invention comprises, as a structural element of the crystal lattice of the compound, a polar solvent, in particular, such as water, methanol or ethanol. The amount of the polar solvent, particularly water, may be present in a stoichiometric or non-stoichiometric ratio.

Also included within the scope of the present invention is a metabolite of the compound of the invention, i.e., a compound formed in vivo upon drug administration.

The term "pharmaceutical composition" as used in the present application includes a product comprising a therapeutically effective amount of the compound, as well as any product formed, directly or indirectly, from a combination comprising the compound.

The term "effective amount" as used in the present application refers to an amount sufficient to achieve a desired therapeutic effect, e.g., an amount capable of achieving alleviation of symptoms associated with diseases to be treated.

The term "treatment" as used in the present application aims to alleviate or eliminate a state or condition of the disease in interest. If one or more indications and symptoms of a subject are decreased or improved observably and/or detectably after the subject receives a therapeutic amount of a compound, an optical isomer or a pharmaceutically acceptable salt thereof, or a pharmaceutical composition thereof according to the method as described herein, the subject is successfully "treated". It should be also understood that the treatment of a disease state or condition not only includes complete treatment, but also includes the situation where the complete treatment is not achieved, but some related biological or medical results are achieved.

"Treatment" refers to any administration of the compound, thus to achieve:

(1) preventing the occurrence of a disease in an animal that may be predisposed to the disease but has not yet experienced or exhibited pathology or symptomology of the disease;

(2) inhibiting a disease (i.e., arresting further development of pathology and/or symptomatology) in an animal that is experiencing or exhibiting the pathology or symptomatology of the disease; or (3) improving a disease (i.e., reversing pathology and/or symptomatology) in an animal that is experiencing or exhibiting the pathology or symptomatology of the disease.

Technical Effects

Through deep researches, a nitrogen-containing benzoheterocycle compound containing a carboxylic acid group is obtained. Via the introduction of the carboxylic acid group, the compound can achieve at least one of the following technical effects:

(1) extremely remarkable liver targeting properties;
(2) excellent pharmacokinetic properties;
(3) potent inhibitory effect against CCR2/CCR5; and
(4) remarkable treating effect for a CCR2- and/or CCR5-mediated relevant disease, especially nonalcoholic fatty liver disease (NAFLD) or the like.

Specific Modes for Carryingout the Invention

Embodiments of the present invention will be described in detail below with reference to examples. However, it will be understood by a person skilled in the art that the following examples are only used for illustration of the invention, but should be deemed as limitation to the scope of the invention. The examples, not indicated with specific conditions, should be performed according to conventional conditions or conditions recommended by manufacturers. The reagents or instruments, not indicated with manufacturers, each are conventional commercially available products.

In conventional synthesis and examples, and synthesis examples of intermediates, the meanings of abbreviations are shown as follows:

| Abbreviations | Meaning | Abbreviations | Meaning |
|---|---|---|---|
| OD | Polysaccharide derivative normal phase coating type chiral chromatographic column, with a silica gel surface coated with cellulose-tri(3,5-dimethylphenyl carbamate) | EEDQ | 2-Ethoxy-1-ethoxycarbonyl-1,2-dihydroquinoline |
| OJ | Polysaccharide derivative normal phase coating type chiral chromatographic column, with a silica gel surface coated with cellulose-tri(4-methyl benzoate) | DEPC | Diethyl cyanophosphonate |
| AS | Polysaccharide derivative normal phase coating type chiral chromatographic column, with a silica gel surface coated with amylose-tri(S)-α-methylphenyl carbamate | DCC | Dicyclohexylcarbodiimide |
| AD | Polysaccharide derivative normal phase coating type chiral chromatographic column, with a silica gel surface coated with amylose-tri(3,5-dimethylphenyl carbamate) | DIC | N,N'-Diisopropylcarbodiimide |
| IA | Solvent-resistant chiral column, with a silica gel surface covalently bonded to amylose-tris(3,5-dimethylphenyl carbamate) | EDC | 1-(3-Dimethylaminopropyl)-3-ethylcarbodiimide |
| IB (IB) | Solvent-resistant chiral column, with a silica gel surface covalently bonded to cellulose-tri(3,5-dimethyl phenyl carbamate) | BOP | Benzotriazole-1-tris(trimethylamino)-trifluorophosphate |
| IC | Solvent-resistant chiral column, with a silica gel surface covalently bonded to cellulose-tri(3,5-dichlorophenyl carbamate) | PyAOP | (3H-1,2,3-triazolo[4,5-B]pyridine-3-oxy)tri-1-pyrrolidyl hexafluorophosphate |

| Abbreviations | Meaning | Abbreviations | Meaning |
| --- | --- | --- | --- |
| ID | Solvent-resistant chiral column, with a silica gel surface covalently bonded to mylose-tri (3-chlorophenyl carbamate) | PyBOP | 1H-benzotriazol-1-yloxytripyrrolidinyl hexafluorophosphate |
| ee | Enantiomeric excess percentage | DIPEA | N,N-Diisopropylethylamine |
| HATU | O-(7-azabenzotriazol-1-yl)-N,N,N',N'-tetramethyluronium hexafluorophosphate | NMM | N-Methylmorpholine |
| HBTU | Benzotriazole-N,N,N',N'-tetramethyluronium hexafluorophosphate | DMAP | p-Dimethylaminopyridine |

Examples and Assays are exemplified below to further illustrate the invention in detail, but not intend to limit the invention. In addition, variations may be made without departing from the scope of the present invention.

The structures of the compounds as described in the following examples were confirmed by a nuclear magnetic resonance ($^1$H NMR) or a mass spectrometry (MS).

The measuring instrument of the nuclear magnetic resonance ($^1$H NMR) was a Bruker 400 MHz nuclear magnetic resonance meter; the measuring solvents were deuterated methanol (CD$_3$OD), deuterated chloroform (CDCl$_3$) and hexadeuterated dimethyl sulfoxide (DMSO-d$_6$); the internal standard substance was tetramethylsilane (TMS).

The abbreviations in the nuclear magnetic resonance (NMR) spectra used in the examples are shown below:
s: singlet, d: doublet, t: triplet, q: quartet, dd: doublet double, qd: quartet doublet, ddd: double double double, ddt: double double triplet, dddd: double double double doublet, m: multiplet, br: broad, J: coupling constant, Hz: hertz, DMSO-d$_6$: deuterated dimethyl sulfoxide.

All δ values are expressed in ppm.

The measuring instrument of the mass spectrometry (MS) was an Agilent (ESI) mass spectrometer, with the model Agilent 6120B.

EXAMPLES

Example 1: Synthesis of (S,E)-3-(8-(4-(2-butoxyethoxy)phenyl)-5-((4-(((1-propyl-1H-imidazol-5-yl)methyl)sulfinyl)phenyl)carbamoyl)-3,4-dihydrobenzo[b]azacyclooctatetraen-1(2H)-yl)-2,2-dimethylpropanoic acid (Compound 1)

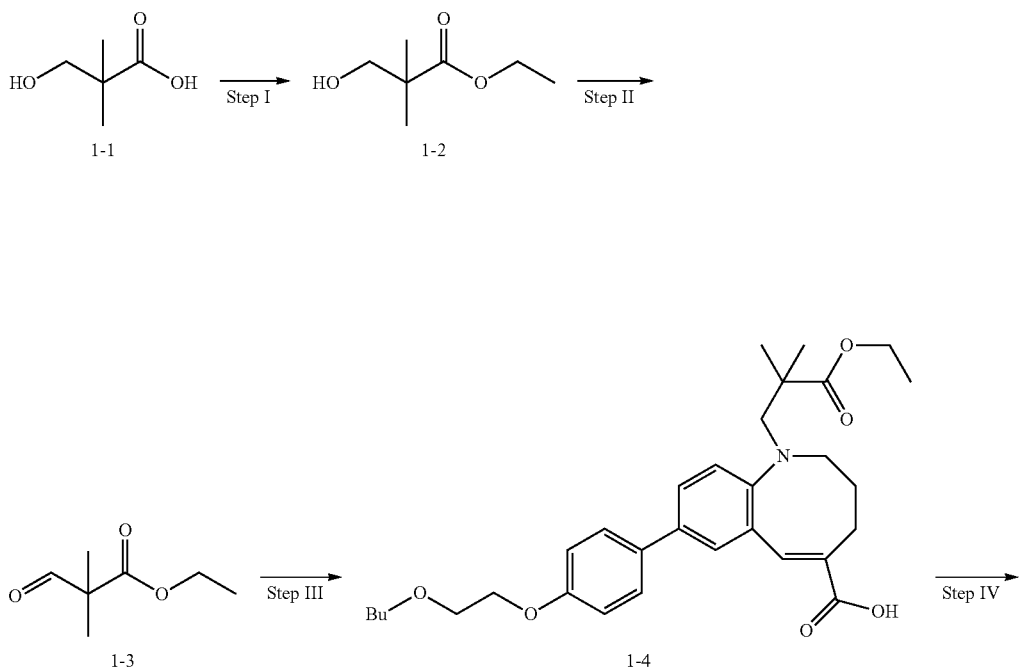

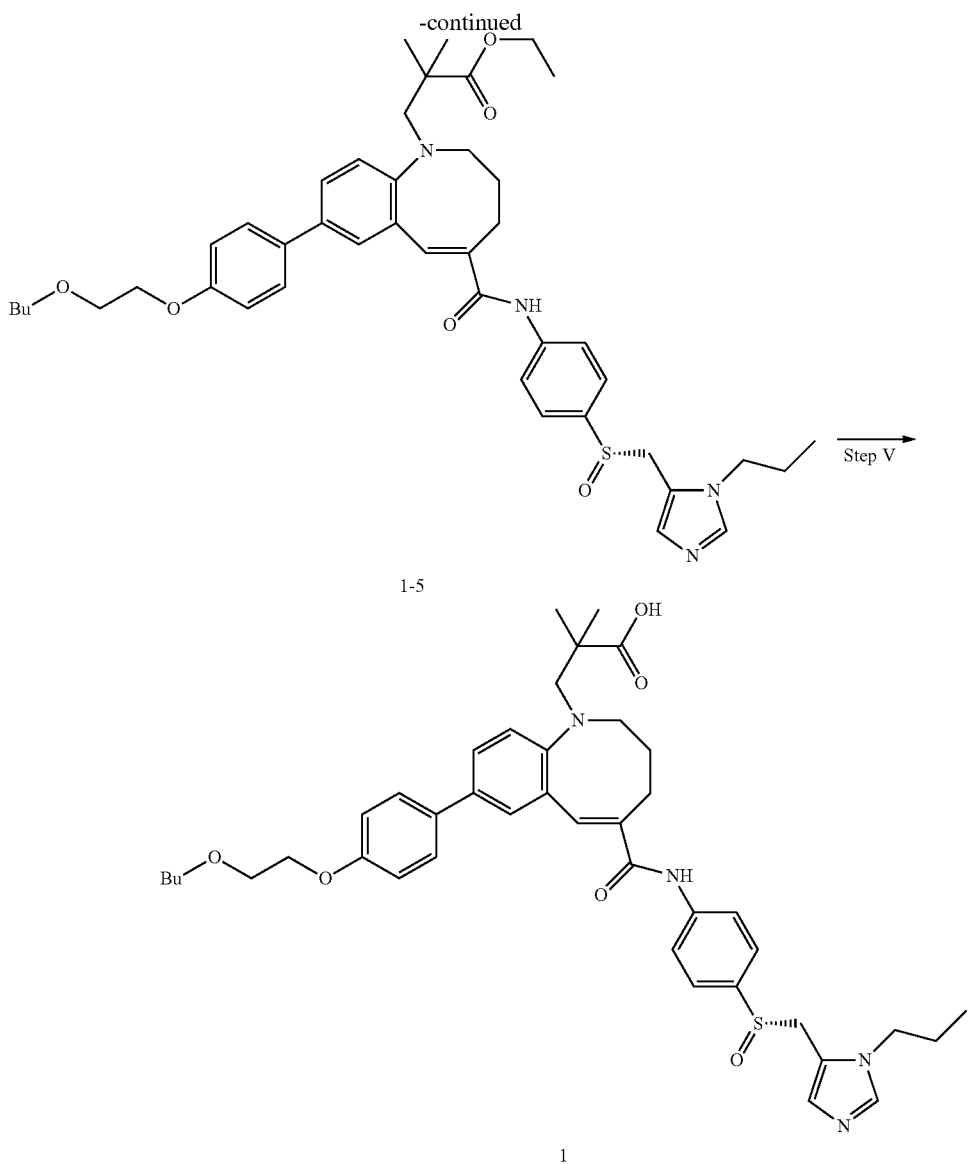

Step I: Synthesis of ethyl 3-hydroxy-2,2-dimethylpropionate

At room temperature, compound 1-1 (1.0 g, 8.5 mmol), cesium carbonate (3.3 g, 10.2 mmol), and N,N-dimethylformamide (15 mL) were charged into a three-necked flask, and next, iodoethane (2.6 g, 17.0 mmol) was added thereto under stirring at room temperature. The system was replaced with nitrogen gas three times and heated to 55° C., and reacted for 16 hours at the temperature. After being cooled to room temperature, the system was poured into ice water (80 mL) and extracted with ethyl acetate (30 mL×3). The organic phase was washed with saturated brine (30 mL×3) and dried over anhydrous sodium sulfate, and the drying agent was removed by filtration. The solvents were removed by evaporation at reduced pressure, and purification with a column chromatography (THF:PE=1:10) was performed to give 1.0 g of the title compound. ESI-MS (m/z): 147.1 [M+H]$^+$.

Step II: Synthesis of ethyl 2,2-dimethyl-3-oxopropionate

Oxalyl chloride (522 mg, 4.1 mmol) was dissolved in dichloromethane (5 mL), and the system was cooled to −78° C. Dimethyl sulfoxide (640 mg, 8.2 mmol) was dropwise added thereto. And after the addition, the system was reacted for 30 min at the temperature. Then, a dichloromethane (5 mL) solution of compound 1-2 (500 mg, 3.4 mmol) was dropwise added. And after the addition, the system was reacted for 2 h at −78° C. Further, triethylamine (1.03 g, 10.2 mmol) was added dropwise. And after the addition, the system was reacted for 1 h at −78° C. and then a further 30 min at room temperature. The reaction was quenched by adding water (30 mL) and extracted with dichloromethane (20 mL×2). The organic phase was washed with saturated brine (30 mL×2) and dried over anhydrous sodium sulfate, and the drying agent was removed by filtration. Solvents were removed by evaporation under reduced pressure, and purification with a column chromatography (THF:PE=1:15)

was performed to give 200 mg of the title compound. ESI-MS (M/z) 145.1 [M+H]⁺.

Step III: Synthesis of (E)-8-(4-(2-butoxyethoxy) phenyl)-1-(3-ethoxy-2,2-dimethyl-3-oxopropyl)-1,2, 3,4-tetrahydrobenzo[b]azacyclooctatetraene-5-formic acid At room temperature, (E)-8-(4-(2-butoxyethoxy)phenyl)-1,2,3,4-tetrahydrobenzo[b]azacyclooctatetraene-5-formic acid (80 mg, 0.2 mmol) and compound 1-3 (432 mg, 3.0 mmol) were dissolved in dioxane (4.5 mL), then trifluoroacetic acid (1.5 mL) was added thereto at room temperature, and after 5 min stirring, sodium cyanoborohydride (252 mg, 4.0 mmol) was further added. After the addition, the mixture was reacted at 60° C. for 2.5 h under microwave. The system was added with water (30 mL) and extracted with ethyl acetate (30 mL×2). The organic phase was washed with saturated brine (30 mL×2) and dried over anhydrous sodium sulfate, and the drying agent was removed by filtration. Solvents were removed by evaporation under reduced pressure, and preparative liquid phase purification was performed to give 150 mg of the title compound. ESI-MS (M/z) 524.3 [M+H]⁺.

Step IV: Synthesis of ethyl (5, E)-3-(8-(4-(2-butoxyethoxy)phenyl)-5-((4-(((1-propyl-1H-imidazol-5-yl)methyl)sulfinyl)phenyl)carbamoyl)-3,4-dihydrobenzo[b]azacyclooctatetraen-1(2H)-yl)-2,2-dimethylpropionate Compound 1-4 (60 mg, 0.11 mmol) was dissolved in dichloromethane (2 mL) and added with thionyl chloride (0.5 mL) at room temperature, and the mixture was reacted for 1 h. The system was drained, and then dissolved by adding dichloromethane (2 mL), the resulting mixture was dropwise added to a dichloromethane (2 mL) solution of (S)-4-(((1-propyl-1H-imidazol-5-yl)methyl)sulfinyl) aniline (46 mg, 0.16 mmol) and 4-dimethylaminopyridine (84 mg, 0.66 mmol). After the addition, the mixture was reacted at room temperature for 3 h. The reaction was quenched by adding water (10 mL) and extracted with dichloromethane (20 mL×2). The organic phase was washed with saturated brine (20 mL×2) and dried over anhydrous sodium sulfate, and the drying agent was removed by filtration. Solvents were removed by evaporation under reduced pressure, and purification was performed on preparative high performance liquid chromatography to give 15 mg of the title compound. ESI-MS (M/z) 769.4 [M+H]⁺.

Step V: Synthesis of (S,E)-3-(8-(4-(2-butoxyethoxy) phenyl)-5-((4-(((1-propyl-1H-imidazol-5-yl)methyl) sulfinyl)phenyl)carbamoyl)-3,4-dihydrobenzo[b] azacyclooctatraen-1(2H)-yl)-2,2-dimethylpropanoic acid At room temperature, compound 1-5 (15 mg, 0.02 mmol) was dissolved in anhydrous ethanol (0.5 mL) and water (1 mL), and sodium hydroxide (8 mg, 0.2 mmol) was added thereto under stirring at room temperature. The mixture was warmed to 45° C. and reacted for 20 h at the temperature. The reaction was detected by LC-MS to show the completion of the reaction. After cooling to room temperature, the system was added with 1N hydrochloric acid aqueous solution to adjust the pH to 5-6 and then extracted with ethyl acetate (20 mL×2). The organic phase was washed with saturated brine (20 mL×1) and dried over anhydrous sodium sulfate, and the drying agent was removed by filtration. The solvents were evaporated under reduced pressure, and purification was performed on preparative high performance liquid chromatography to give 5 mg of the title compound 1.

The structure of compound 1 was characterized as follows:

¹H NMR (400 MHz, DMSO-d₆) δ 10.07 (s, 1H), 7.89 (d, J=8.5 Hz, 2H), 7.63 (s, 1H), 7.55 (d, J=8.6 Hz, 2H), 7.51 (d, J=2.4 Hz, 1H), 7.47 (d, J=9.2 Hz, 4H), 7.12 (d, J=8.8 Hz, 1H), 7.00 (d, J=8.5 Hz, 2H), 6.48 (s, 1H), 4.35 (d, J=14.3 Hz, 1H), 4.17 (d, J=14.3 Hz, 1H), 4.11 (dd, J=5.8, 3.6 Hz, 2H), 3.80 (td, J=7.1, 2.2 Hz, 2H), 3.74-3.68 (M, 2H), 3.49-3.42 (M, 6H), 2.38 (d, J=6.2 Hz, 2H), 1.65 (q, J=7.3 Hz, 2H), 1.55-1.45 (M, 4H), 1.39-1.27 (M, 2H), 1.17 (s, 6H), 0.88 (t, J=7.3 Hz, 3H), 0.81 (t, J=7.4 Hz, 3H). ESI-MS (M/z): 741.4 [M+H]⁺.

Example 2: Synthesis of (E)-3-(8-(4-(2-butoxyethoxy)phenyl)-5-((4-(((4-methyl-1-propyl-1H-imidazol-5-yl)methyl)sulfinyl)phenyl)carbamoyl)-3,4-dihydrobenzo[b]azacyclooctatetraen-1(2H)-yl)-2,2-dimethylpropanoic acid (Compound 2)

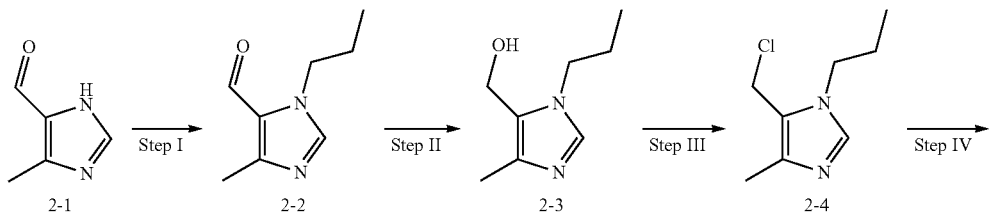

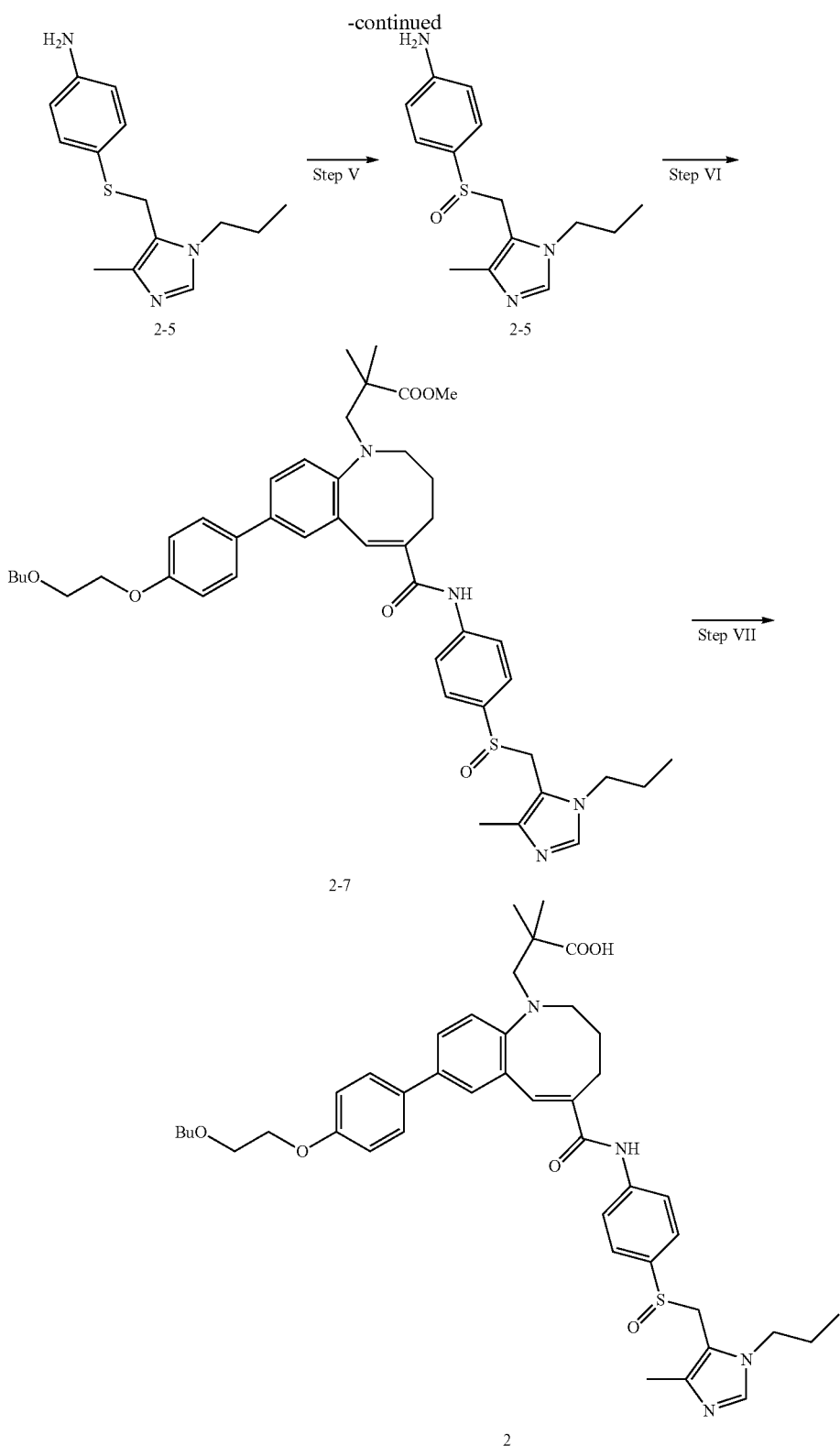

Step I: Synthesis of 4-methyl-1-propyl-1H-imidazol-5-yl-formaldhyde

At room temperature, compound 2-1 (500 mg, 4.5 mmol), potassium carbonate (941 mg, 6.8 mmol) and N,N-dimethylformamide (10 mL) were added into a three-necked flask, and iodopropane (1.5 g, 9.1 mmol) was added thereto. Under the protection of nitrogen gas, the mixture was warmed to 50° C. and reacted for 16 h at the temperature. The system was cooled to room temperature, poured into ice water (100 mL) and extracted with ethyl acetate (40 mL×3). The organic phase was washed with saturated saline (30 mL×3), dried over anhydrous sodium sulfate, and concentrated, and purified by column chromatography to give 260 mg of the title compound. ESI-MS (M/z) 153.1 [M+H]$^+$.

Step II: Synthesis of (4-methyl-1-propyl-1H-imidazol-5-yl) methanol

Compound 2-2 (210 mg, 1.4 mmol) was dissolved in anhydrous methanol (5 mL) and cooled to 0° C., and sodium borohydride (66 mg, 1.7 mmol) was added thereto in batches. The mixture was reacted at the temperature for 30 min. The system was added with water (10 mL) to quench the reaction and concentrated, and ethyl acetate (30 mL×2) was added thereto for extraction. The organic phase was washed with saturated brine (10 mL×2), dried over anhydrous sodium sulfate, and concentrated to give 155 mg of the title compound. ESI-MS (M/z): 155.1 [M+H]$^+$.

Step III: Synthesis of 5-(chloromethyl)-4-methyl-1-propyl-1H-imidazole

Compound 2-3 (155 mg, 1.0 mmol) was dissolved in acetonitrile (3 mL), and thionyl chloride (1 mL) was added thereto at room temperature. Then, the mixture was warmed to 70° C. and reacted for 2 h. The system was cooled to room temperature, concentrated, added with ethyl acetate (5 mL), and stirred at room temperature for 30 minutes. Suction filtration was performed to give 175 mg of the hydrochloride of the title compound. $^1$H NMR (400 MHz, DMSO-d$_6$) δ 14.93 (s, 1H), 9.14 (s, 1H), 5.06 (s, 2H), 4.15 (t, J=7.4 Hz, 2H), 2.34 (s, 3H), 1.86 (H, J=7.4 Hz, 2H), 0.91 (t, J=7.4 Hz, 3H).

Step IV: Synthesis of 4-(((4-methyl-1-propyl-1H-imidazol-5-yl)methyl)thio) aniline At room temperature, 4-aminothiophenol (240 mg, 1.9 mmol), triethylamine (576 mg, 5.7 mmol) and tetrahydrofuran (10 mL) were added to a three-necked flask and cooled to 0° C., and a tetrahydrofuran (5 mL: 0.5 mL) aqueous solution of compound 2-4 (400 mg, 1.9 mmol) was added dropwise thereto. After the addition, the mixture was warmed to room temperature and reacted for 2 hours. The system was poured into water (50 mL) and extracted with ethyl acetate (40 mL×3). The organic phase was washed with saturated brine (30 mL×3), dried over anhydrous sodium sulfate, and concentrated. Purification was performed on a preparative high performance liquid chromatography to give 160 mg of the title compound. ESI-MS (M/z) 262.1[M+H]$^+$.

Step V: Synthesis of 4-(((4-methyl-1-propyl-1H-imidazol-5-yl)methyl)sulfinyl) aniline Compound 2-5 (160 mg, 0.61 mmol) was dissolved in dichloromethane (5 mL) and cooled to 0° C., and m-chloroperoxybenzoic acid (105 mg, 0.61 mmol) was added thereto in batches. After the addition, the mixture was reacted for 30 min at the temperature. The system was added with saturated anhydrous sodium sulfite solution (10 mL) to quench the reaction, and extracted by adding dichloromethane (20 mL×3). The organic phase was washed with saturated brine (20 mL×2), dried over anhydrous sodium sulfate, and concentrated. Purification was performed on preparative high performance liquid chromatography to give 180 mg of the title compound. ESI-MS (M/z) 278.1 [M+H]$^+$.

Step VI: Synthesis of methyl (E)-3-(8-(4-(2-butoxyethoxy)phenyl)-5-((4-(((4-methyl-1-propyl-1H-imidazol-5-yl)methyl)sulfinyl)phenyl)carbamoyl)-3,4-dihydrobenzo[b]azacyclooctatetraen-1(2H)-yl)-2,2-dimethylpropionate The synthesis was performed by applying a method similar to Step IV in Example 1, except that (S)-4-(((1-propyl-1H-imidazol-5-yl)methyl)sulfinyl)aniline was replaced with compound 2-6, and purification was performed on column chromatography to give 230 mg of the title compound. ESI-MS (M/z) 769.4 [M+H]$^+$ Step VII: Synthesis of (E)-3-(8-(4-(2-butoxyethoxy)phenyl)-5-((4-(((4-methyl-1-propyl-1H-imidazol-5-yl)methyl)sulfinyl)phenyl)carbamoyl)-3,4-dihydrobenzo[b]azacyclooctatetraen-1(2H)-yl)-2,2-dimethylpropanoic acid The synthesis was performed by applying a method similar to Step V in Example 1, except that compound 1-5 was replaced with compound 2-7, and purification was performed on preparative high performance liquid chromatography to give 60 mg of the title compound 2.

The structure of compound 2 was characterized as follows:

$^1$H NMR (400 MHz, DMSO-d$_6$) δ 12.45 (s, 1H), 10.08 (s, 1H), 7.87 (d, J=8.5 Hz, 2H), 7.53 (t, J=9.2 Hz, 4H), 7.50-7.44 (m, 2H), 7.39 (d, J=8.5 Hz, 2H), 7.12 (d, J=8.9 Hz, 1H), 7.00 (d, J=8.6 Hz, 2H), 4.26 (d, J=14.3 Hz, 1H), 4.16 (d, J=14.3 Hz, 1H), 4.13-4.07 (m, 2H), 3.79 (ddd, J=18.6, 13.9, 6.8 Hz, 2H), 3.73-3.66 (m, 2H), 3.52-3.40 (m, 4H) 3.29 (s, 2H), 2.38 (s, 2H), 1.70-1.63 (M, 2H), 1.61 (s, 3H), 1.50 (dt, J=13.8, 6.2 Hz, 4H), 1.36-1.29 (M, 2H), 1.17 (s, 6H), 0.88 (t, J=7.3 Hz, 3H), 0.82 (t, J=7.1 Hz, 3H). ESI-MS (M/z): 755.3 [M+H]$^+$.

Example 3

Compound 2 (260 mg) obtained in Example 2 was separated on chiral column for one of its enantiomers by applying SFC method, and the corresponding fraction was collected. The solvent was removed by rotary evaporation to give the pure optical isomer. The preparation conditions are as follows: chiral column: CHIRALPAK ID; chiral column model: 0.46 cm I.D.×15 cm L; sampling quantity: 0.5 uL; mobile phase:CO$_2$/(EtOH:DCM:NH$_4$OH=60:40:0.1)=55/45 (V/V); flow rate: 2.0 ml/min; wavelength: UV 254 nm; 100 mg of the isomer A of compound 2 was obtained with a retention time of 4.773 min.

The structure of the isomer A was characterized as follows:

$^1$H NMR (400 MHz, DMSO-d$_6$) δ 12.45 (s, 1H), 10.09 (s, 1H), 7.87 (d, J=8.7 Hz, 2H), 7.58-7.50 (m, 4H), 7.49 (s, 1H), 7.48-7.44 (m, 1H), 7.39 (d, J=8.7 Hz, 2H), 7.12 (d, J=8.8 Hz, 1H), 7.02-6.97 (m, 2H), 4.26 (d, J=14.4 Hz, 1H), 4.16 (d, J=14.4 Hz, 1H), 4.13-4.08 (m, 2H), 3.84-3.75 (m, 2H), 3.70 (dd, J=5.6, 3.7 Hz, 2H), 3.50-3.42 (m, 4H), 3.29 (s, 2H), 2.38 (s, 2H), 1.70-1.63 (M, 2H), 1.61 (s, 3H), 1.54-1.45 (M, 4H), 1.36-1.30 (M, 2H), 1.17 (s, 6H), 0.88 (t, J=7.4 Hz, 3H), 0.82 (t, J=7.3 Hz, 3H). ESI-MS (M/z): 755.3 [M+H]$^+$.

specific optical rotation: $[α]_{280\ nm}^{20°\ C.}$=+58.0 (c=0.044, MeOH).

Example 4

Compound 2 (260 mg) obtained in Example 2 was separated on chiral column for the other one of its enantiomers by applying SFC method, and the corresponding fraction was collected. The solvent was removed by rotary evaporation to give the pure optical isomer. The preparation conditions are as follows: chiral column: CHIRALPAK ID; chiral column model: 0.46 cm I.D.×15 cm L; sampling quantity: 0.5 μL; mobile phase:$CO_2$/(EtOH:DCM: $NH_4OH$=60:40:0.1)=55/45 (V/V); flow rate: 2.0 ml/min; wavelength: UV 254 nm; 103 mg of the isomer B of compound 2 was obtained with a retention time of 7.107 min.

The structure of the isomer B was characterized as follows:

$^1$H NMR (400 MHz, DMSO-$d_6$) δ 12.35 (brs, 1H), 10.16 (s, 1H), 7.88 (d, J=8.7 Hz, 2H), 7.56 (s, 1H), 7.53 (s, 2H), 7.50 (d, J=1.9 Hz, 1H), 7.48-7.44 (m, 2H), 7.39 (d, J=8.7 Hz, 2H), 7.12 (d, J=8.8 Hz, 1H), 6.99 (d, J=8.8 Hz, 2H), 4.26 (d, J=14.3 Hz, 1H), 4.16 (d, J=14.4 Hz, 1H), 4.13-4.08 (m, 2H), 3.86-3.73 (m, 2H), 3.73-3.68 (m, 2H), 3.46 (t, J=6.5 Hz, 4H), 3.30 (s, 2H), 2.38 (s, 2H), 1.66 (q, J=7.4 Hz, 2H), 1.61 (s, 3H), 1.55-1.44 (M, 4H), 1.36-1.30 (M, 2H), 1.16 (s, 6H), 0.88 (t, J=7.4 Hz, 3H), 0.82 (t, J=7.3 Hz, 3H). ESI-MS (M/z): 755.3 [M+H]$^+$.

specific optical rotation: $[α]_{280\ nm}^{20°\ C.}$=-49.0 (c=0.046, MeOH).

Example 5 (E)-3-(8-(4-(2-butoxyethoxy)phenyl)-5-((4-(((5-methyl-1-propyl-1H-imidazol-4-yl)methyl)sulfinyl)phenyl)carbamoyl)-3,4-dihydrobenzo[b]azacyclooctatetraen-1(2H)-yl)-2,2-dimethylpropanoic acid (Compound 5)

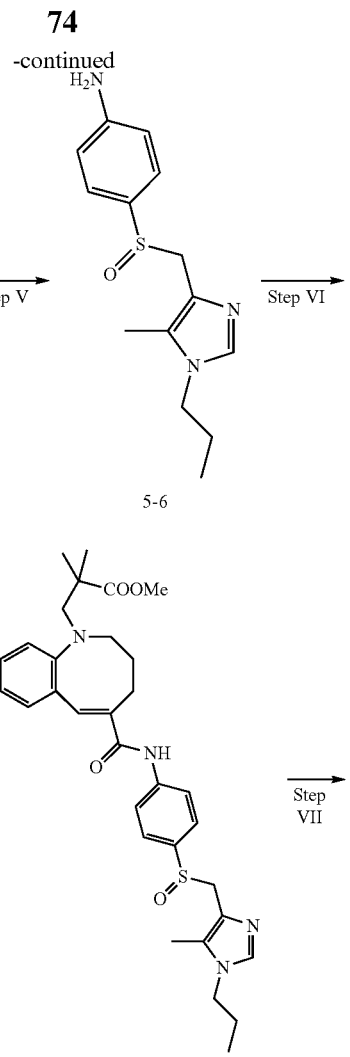

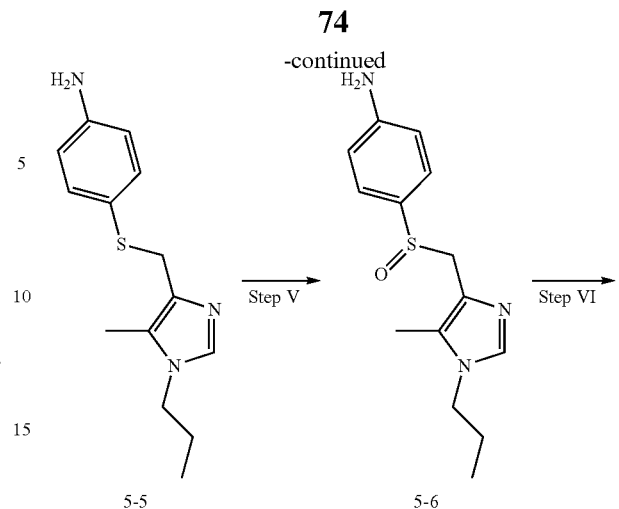

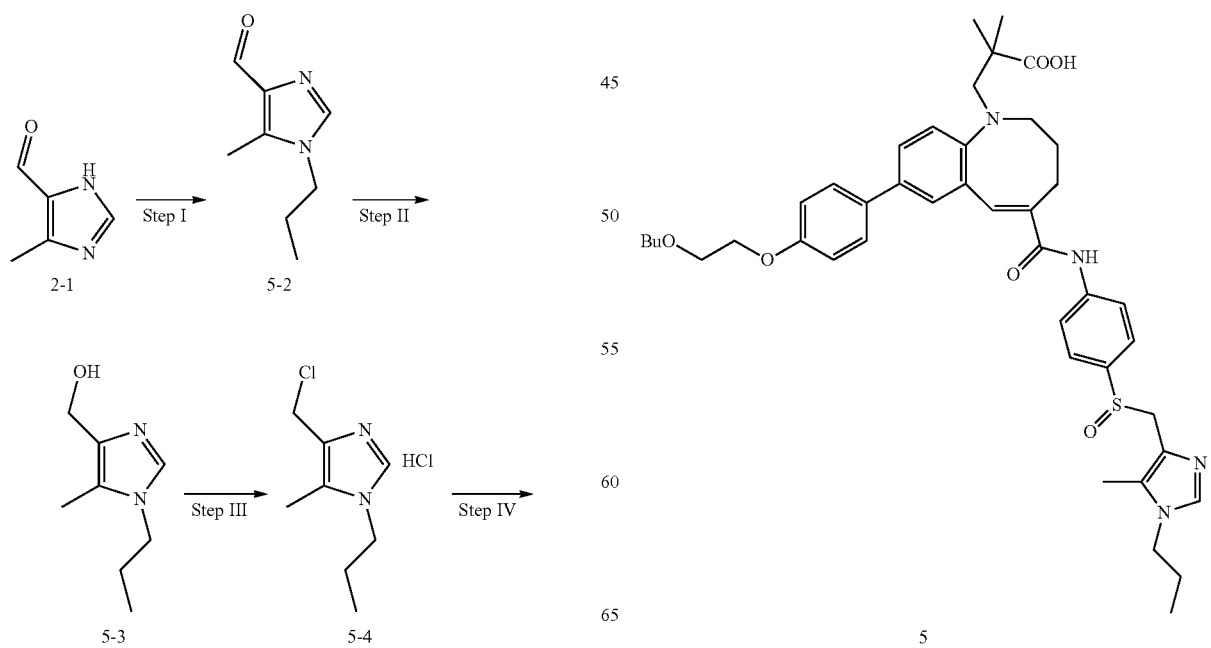

Step I: Synthesis of 5-methyl-1-propyl-1H-imidazol-4-yl-formaldehyde

At room temperature, compound 2-1 (500 mg, 4.5 mmol), potassium carbonate (941 mg, 6.8 mmol) and N,N-dimethylformamide (10 mL) were added into a three-necked flask, and iodopropane (1.5 g, 9.1 mmol) was added thereto. Under the protection of nitrogen gas, the mixture was warmed to 50° C. and reacted at the temperature for 16 h, and then cooled to room temperature. The system was poured into ice water (100 mL) and extracted with ethyl acetate (40 mL×3). The organic phase was washed with saturated saline (30 mL×3), dried over anhydrous sodium sulfate, and concentrated. Purification was performed on column chromatography to give 230 mg of the title compound. ESI-MS (M/z) 153.1 [M+H]+.

Step II: Synthesis of (5-methyl-1-propyl-1H-imidazol-4-yl) methanol

Compound 5-2 (210 mg, 1.4 mmol) was dissolved in anhydrous methanol (5 mL) and cooled to 0° C., and sodium borohydride (66 mg, 1.7 mmol) was added thereto in batches. The mixture was reacted at the temperature for 30 min. The system was added with water (10 mL) to quench the reaction and concentrated, and ethyl acetate (30 mL×2) was added thereto for extraction. The organic phase was washed with saturated brine (10 mL×2), dried over anhydrous sodium sulfate, and concentrated to give 155 mg of the title compound. ESI-MS (M/z): 155.1 [M+H]+.

Step III: Synthesis of 4-(chloromethyl)-5-methyl-1-propyl-1H-imidazole hydrochloride Compound 5-3 (155 mg, 1.0 mmol) was dissolved in acetonitrile (3 mL), and added with thionyl chloride (1 mL) at room temperature, and then warmed to 70° C. and reacted for 2 h. The reaction mixture was cooled to room temperature, concentrated, added with ethyl acetate (5 mL), and stirred at room temperature for 30 minutes, and then suction filtration was performed to give 175 mg of the title compound. ESI-MS (M/z) 173.1 [M+H]+.

Step IV: Synthesis of 4-(((5-methyl-1-propyl-1H-imidazol-4-yl)methyl)thio) aniline At room temperature, 4-aminothiophenol (240 mg, 1.9 mmol), triethylamine (576 mg, 5.7 mmol) and tetrahydrofuran (10 mL) were added to a three-necked flask and cooled to 0° C., and a tetrahydrofuran aqueous solution (5 mL: 0.5 mL) of compound 5-4 (400 mg, 1.9 mmol) was added dropwise thereto. After the addition, the mixture was warmed to room temperature and reacted for 2 hours. The system was poured into water (50 mL) and extracted with ethyl acetate (40 mL×3). The organic phase was washed with saturated brine (30 mL×3), dried over anhydrous sodium sulfate, and concentrated, purification was performed on preparative high performance liquid chromatography to give 160 mg of the title compound. ESI-MS (M/z) 262.1 [M+H]+.

Step V: Synthesis of 4-(((5-methyl-1-propyl-1H-imidazol-4-yl)methyl)sulfinyl) aniline Compound 5-5 (160 mg, 0.61 mmol) was dissolved in dichloromethane (5 mL) and cooled to 0° C., m-chloroperoxybenzoic acid (105 mg, 0.61 mmol) was added thereto in batches. After the addition, the mixture was reacted for 30 min at the temperature. The system was added with saturated anhydrous sodium sulfite solution (10 mL) to quench the reaction, and extracted by adding dichloromethane (20 mL×3). The organic phase was washed with saturated brine (20 mL×2), dried over anhydrous sodium sulfate, and concentrated. Purification was performed on preparative high performance liquid chromatography to give 180 mg of the title compound. ESI-MS (M/z) 278.1 [M+H]+.

Step VI: Synthesis of methyl (E)-3-(8-(4-(2-butoxyethoxy)phenyl)-5-((4-(((5-methyl-1-propyl-1H-imidazol-4-yl)methyl)sulfinyl)phenyl)carbamoyl)-3,4-dihydrobenzo[b]azacyclooctatetraen-1(2H)-yl)-2,2-dimethylpropionate Compound 5-6 (330 mg, 0.65 mmol) was dissolved in dichloromethane (10 mL), and (S)-4-{[(4-methyl-1-propyl-1H-imidazol-5-yl)methyl]sulfinyl} aniline (180 mg, 0.65 mmol) was added to the reaction system. 1-ethyl-(3-dimethylaminopropyl)carbodiimide hydrochloride (376 mg, 1.95 mmol), and 4-dimethylaminopyridine (237 mg, 1.95 mmol) were added and reacted at room temperature overnight. The reaction mixture was added with water (20 mL) and extracted with dichloromethane (50 mL×3). The organic phases were combined, dried over anhydrous sodium sulfate, concentrated, and purified by column chromatography to give 230 mg of the title compound. ES I-MS (M/z) 770.3 [M+H]+.

Step VII: Synthesis of (E)-3-(8-(4-(2-butoxyethoxy)phenyl)-5-((4-(((5-methyl-1-propyl-1H-imidazol-4-yl)methyl)sulfinyl)phenyl)carbamoyl)-3,4-dihydrobenzo[b]azacyclooctatetraen-1(2H)-yl)-2,2-dimethylpropanoic acid Compound 5-7 (230 mg, 0.30 mmoL) was dissolved in tetrahydrofuran/methanol (10 mL/10 mL), and the lithium hydroxide solution (5 mL, 1M) was added thereto. The system was warmed to 70° C. and reacted for 2 h. After the reaction was cooled to room temperature, it was adjusted with 1M hydrochloric acid to pH=7, and water (50 mL) was added thereto, and extracted with ethyl acetate (30 mL×3). The organic phase was washed with saturated brine (30 mL×2), dried over anhydrous sodium sulfate, concentrated, and purified by preparative high performance liquid chromatography to give 60 mg of the title compound 5.

The structure of compound 5 was characterized as follows:

$^1$H NMR (400 MHz, Chloroform-d) δ 9.31 (s, 1H), 7.91 (s, 2H), 7.54 (dd, J=14.8, 3.9 Hz, 4H), 7.41 (dd, J=13.6, 6.1 Hz, 4H), 7.02 (s, 2H), 6.93 (s, 1H), 4.26 (d, J=15.2 Hz, 1H), 4.20 (s, 2H), 4.10 (d, J=10.4 Hz, 1H), 3.89 (s, 2H), 3.85 (s, 2H), 3.59 (s, 2H), 3.42 (s, 2H), 3.14 (s, 2H), 2.68 (s, 2H), 2.21 (s, 3H), 1.82 (s, 2H), 1.10 (s, 6H), 1.02-0.97 (M, 6H). ESI-MS (M/z): 755.4 [M+H]+.

Example 6 Synthesis of (E)-3-(8-(4-(2-methoxy-ethoxy)phenyl)-5-((4-(((1-(2-methoxyethyl)-1H-imidazol-5-yl)methyl)sulfinyl)phenyl)carbamoyl)-3,4-dihydrobenzo[b]azacyclooctatetraen-1(2H)-yl)-2,2-dimethylpropanoic acid (Compound 6)
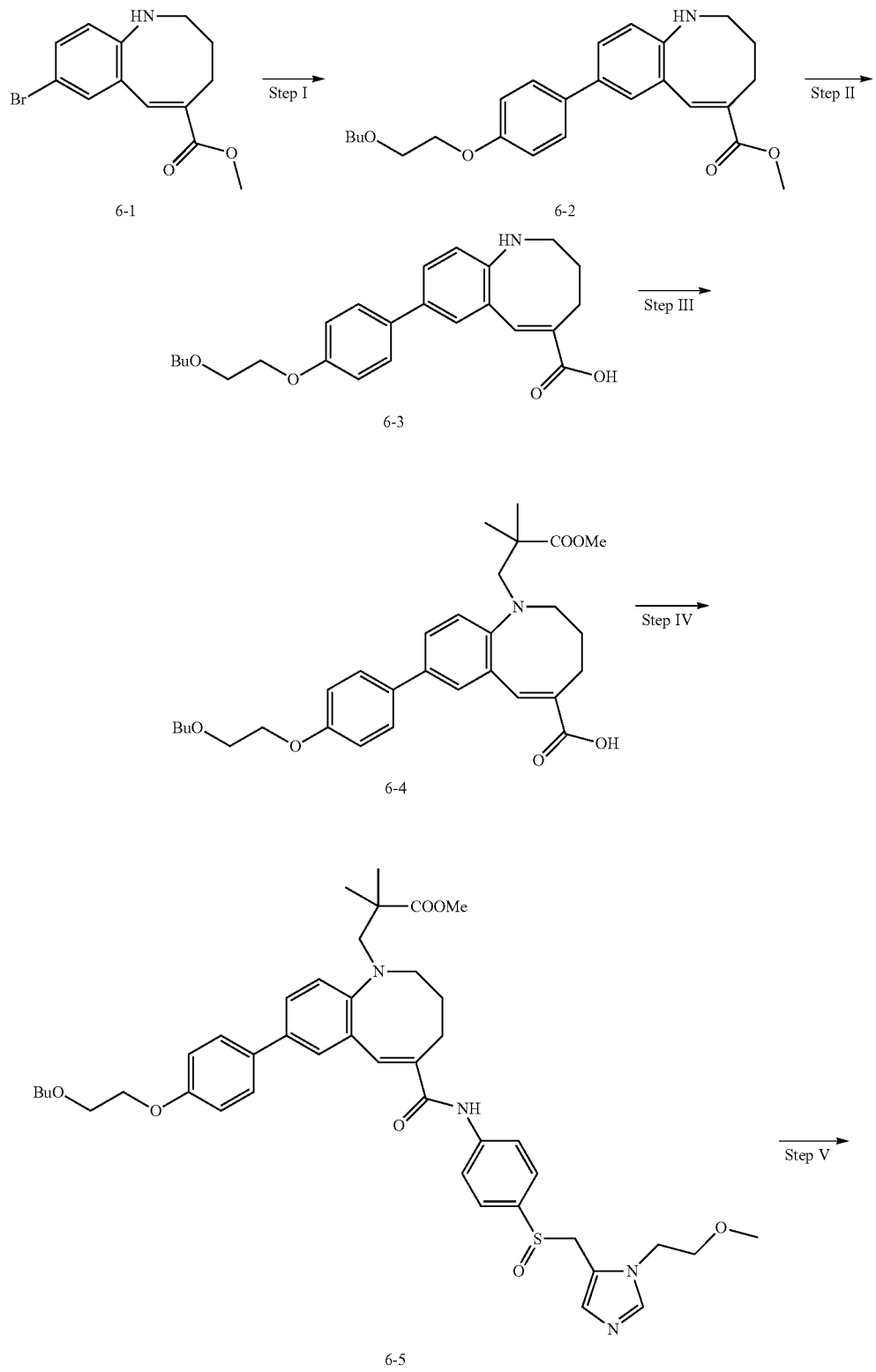

-continued

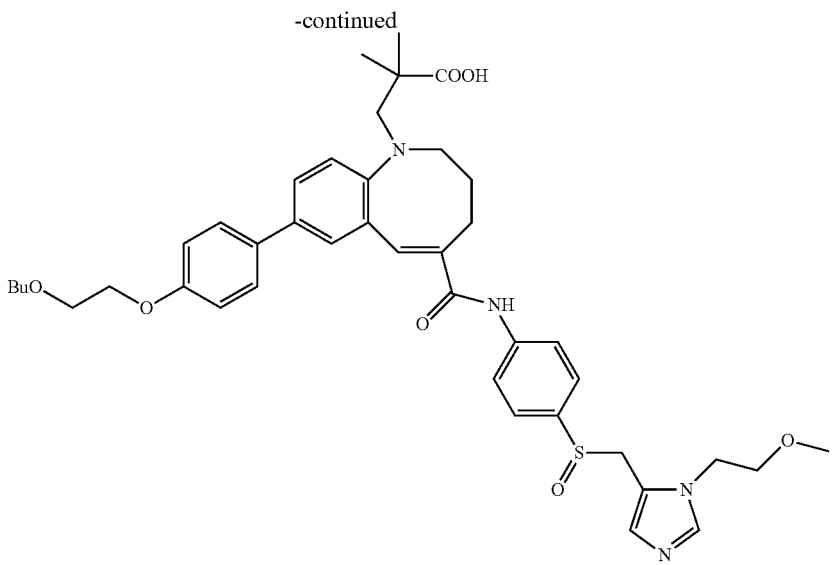

6

Step I: Synthesis of methyl (E)-8-(4-(2-methoxyethoxy)phenyl)-1,2,3,4-tetrahydrobenzo[b]azacyclooctatetraene-5-formate Compound 6-1 (816 mg, 2.55 mmoL), 4-(2-methoxyethoxy) phenylboronic acid (500 mg, 2.55 mmoL), palladium acetate (20 mg, 0.085 mmoL), potassium phosphate (540 mg, 2.53 mmoL), tri-tert-butylphosphonium tetrafluoroborate (98 mg, 0.35 mmoL), and toluene/water 10:1 (5 mL) were added into a microwave tube and reacted under the protection of nitrogen gas at the microwave condition of 100° C. for 3 h. After being cooled to room temperature, the system was poured into water (50 mL) and extracted with ethyl acetate (30 m×3), and the organic phase was washed with saturated brine (30 mL×3), dried over anhydrous sodium sulfate, concentrated, and purified by column chromatography to give 530 mg of the title compound. ESI-MS (M/z) 410.2 [M+H]$^+$.

Step II: Synthesis of (E)-8-(4-(2-methoxyethoxy)phenyl)-1,2,3,4-tetrahydrobenzo[b]azacyclooctatetraene-5-formic acid Compound 6-2 (530 mg, 1.45 mmoL) was dissolved in tetrahydrofuran/methanol (10 mL/10 mL), and sodium hydroxide solution (5 mL, 1M) was added. The system was heated to 70° C. and reacted for 2 h. After the reaction was cooled to room temperature, it was adjusted with 1M hydrochloric acid to pH=7. The system was added with water (50 mL), and extracted with ethyl acetate (30 mL×3). The organic phase was washed with saturated brine (30 mL×2), dried over anhydrous sodium sulfate, concentrated, and purified by column chromatography to give 388 mg of the title compound. ESI-MS (M/z) 396.2 [M+H]$^+$.

Step III: Synthesis of (E)-8-(4-(2-methoxyethoxy)phenyl)-1-(3-methoxy-2,2-dimethyl-3-oxopropyl)-1,2,3,4-tetrahydrobenzo[b]azacyclooctatetraene-5-formic acid Oxalyl chloride (3.818 g, 30 mmol) was dissolved in dichloromethane and cooled to −78° C., and then under the protection of nitrogen gas, dimethyl sulfoxide (3.12 g, 40 mmol) was added dropwise thereto. The mixture was reacted at the temperature for 30 min. The above reaction liquid was added with dichloromethane solution of methyl 2,2-dimethyl-3-hydroxypropionate (1.32 g, 10 mmol), and reacted at the temperature for 2 h. Triethylamine (10 g, 100 mmol) was added thereto and the mixture was reacted for 1 hour at the temperature. The mixture was warmed to −20° C., and trifluoroacetic acid was added dropwise to allow the reaction system to be acidic (pH=1.0). Compound 6-3 (388 mg, 1.1 mmol) and sodium triacetoxyborohydride (2.2 g, 10 mmol) were added to the reaction system, and the resulting mixture was reacted at the temperature for 1 hour. The reaction solution was added with distilled water (100 mL), and extracted with dichloromethane (30 mL×3). The organic phases were combined and washed with saturated sodium bicarbonate (100 mL×1), saturated brine (100 mL×1), and water (100 mL×1) successively, dried over anhydrous sodium sulfate, and purified by column chromatography to give 300 mg of the title compound. ES I-MS (M/z) 510.3 [M+H]$^+$.

Step IV: Synthesis of methyl (E)-3-(8-(4-(2-methoxyethoxy)phenyl)-5-((4-(((1-(2-methoxyethyl)-1H-imidazol-5-yl)methyl)sulfinyl)phenyl)carbamoyl)-3,4-dihydrobenzo[b]azacyclooctatetraen-1(2H)-yl)-2,2-dimethylpropionate Compound 6-4 (300 mg, 0.65 mmol) was dissolved in dichloromethane (10 mL), and (S)-4-{[(1-(2-methoxyethyl)-1H-imidazol-5-yl)methyl]sulfinyl} aniline (180 mg, 0.65 mmol) was added to the reaction system, followed by an addition of 1-ethyl-(3-dimethylaminopropyl)carbodiimide hydrochloride (376 mg, 1.95 mmol) and 4-dimethylaminopyridine (237 mg, 1.95 mmol), then reacted at room temperature overnight. The reaction mixture was added with water (20 mL) and extracted with dichloromethane (50 mL×3). The organic phases were combined, dried over anhydrous sodium sulfate, concentrated, and purified by column chromatography to give 155 mg of the title compound. ESI-MS (M/z) 771.3 [M+H]$^+$.

Step V: Synthesis of (E)-3-(8-(4-(2-methoxyethoxy)phenyl)-5-((4-(((1-(2-methoxyethyl)-1H-imidazol-5-yl)methyl)sulfinyl)phenyl)carbamoyl)-3,4-dihydrobenzo[b]azacyclooctatetraen-1(2H)-yl)-2,2-dimethylpropanoic acid Compound 6-5 (155 mg, 0.20 mmoL) was dissolved in tetrahydrofuran/methanol (10 mL/10 mL), and sodium hydroxide solution (5 mL, 1M) was added thereto. The system was heated to 70° C. and reacted for 2 h. After the reaction was cooled to room temperature, the system was adjusted with 1M hydrochloric acid to pH=7. The system was added with water (50 mL) and extracted with ethyl acetate (30 mL×3). The organic phase was washed with saturated brine (30 mL×2), dried over anhydrous sodium sulfate, concentrated, and purified by preparative high performance liquid chromatography to give 8 mg of the title compound 6.

The structure of compound 6 was characterized as follows:
$^1$H NMR (400 MHz, Chloroform-d) δ 9.37 (s, 1H), 8.29 (s, 1H), 7.96 (d, J=8.3 Hz, 2H), 7.57 (dd, J=8.4, 2.2 Hz, 1H), 7.52 (d, J=8.2 Hz, 2H), 7.41 (s, 1H), 7.37 (d, J=8.5 Hz, 1H), 7.28 (d, J=8.3 Hz, 2H), 7.03 (d, J=8.3 Hz, 2H), 6.88 (s, 1H), 6.58 (s, 1H), 4.37 (d, J=14.6 Hz, 1H), 4.32-4.25 (m, 1H), 4.20 (t, J=4.9 Hz, 2H), 4.11 (d, J=15.7 Hz, 1H), 3.95 (d, J=14.7 Hz, 1H), 3.85 (t, J=5.0 Hz, 2H), 3.64 (d, J=8.4 Hz, 2H), 3.59 (d, J=6.7 Hz, 2H), 3.44 (d, J=15.9 Hz, 2H), 3.34 (s, 3H), 3.15 (s, 2H), 2.68 (d, J=7.6 Hz, 2H), 1.65 (t, J=7.5 Hz, 4H), 1.46-1.42 (m, 2H), 1.13 (s, 3H), 1.09 (s, 3H), 0.98 (d, J=7.4 Hz, 3H), ESI-MS (m/z): 757.4 [M+H]$^+$.

Pharmacological Activity Assay

The following examples further illustrate the invention, but are not meant to limit the scope of the invention.

Experimental Example 1: Inhibition Test on Activity of CCR2/CCR5 in Cells

Test Principles
HEK293 cells that stably express CCR2 and CCR5 receptor proteins were first labeled with calcium ion sensitive fluorescent probe and then stimulated with corresponding ligands (MCP1 and RANTES). After the stimulation, the receptors were activated to trigger the release of the calcium ions from endoplasmic reticulum to cytoplasm. And once the calcium ions were captured by the fluorescent probe, the fluorescent signal could be triggered. The inhibition of compounds on CCR2 and CCR5 can be evaluated by detecting the intensity of the fluorescent signal.

Materials Used for Experiments:
HEK293 cells: WuXi Apptec Co., Ltd;
384-well plates (384 well Poly-D-Lysine protein coating plate), Greiner #781946;
Monocyte chemotactic protein 1 (MCP 1): CCR2 Agonist, PeproTech-300-04;
Regulating and activating normal T-cell expression secretion factor (RANTES): CCR5 Agonist, PeproTech-300-06.
To each well of the 384-well plates, 2×10$^4$ HEK293 cells were added and cultured overnight. After being labelled by fluorescent probe, MCP1 and RANTES in different concentrations were added, and the fluorescent signal was read. The fluorescence signal was plotted in relation to the ligand concentration, and according to the four-parameter model, IC$_{50}$ values were calculated as the ligand concentrations of the CCR2 and CCR5 for the subsequent detection of the compounds.

By referring to the above results, cells were incubated with the test compound in different concentrations (5000 nM, 1250 nM, 313 nM, 78 nM, 20 nM, 4.8828 nM, 1.2207 nM, 0.3052 nM, 0.0763 nM, and 0.0191 nM), and after MCP1 and RANTES were added thereto, the fluorescent signal was read. The inhibition activity of each concentration group was calculated, wherein the solvent group (not containing the compound) was as the negative control, and the Buffer group (not containing any ligand) was as the blank control:

Relative inhibition activity percentage=1−(fluorescent signal of each concentration group−fluorescent signal of the blank group)/(fluorescent signal of the solvent group−fluorescent signal of the blank group)*100%.

The inhibition activity percentage of each concentration group was plotted in relation to the concentration of the compound, and the curve was fitted according to the four-parameter model, IC$_{50}$ values were calculated:

$$y=\min+(\max-\min)/(1+(x/IC_{50})^\wedge(-\text{Hillslope}))$$

wherein y is the relative inhibition activity percentage; max, min are the maximum and minimum values of the fitted curve, respectively; x is the concentration of the compound, and Hillslope is the slope of the curve.

Test Results
According to the above method, the inhibition activity of the compound against CCR2/CCR5 was determined, and the results are shown in Table 1:

TABLE 1

Inhibition results of the compound against the CCR2/CCR5 in cells

| Compound No. | IC$_{50}$ (nM) | |
| --- | --- | --- |
| | CCR2 | CCR5 |
| Compound 1 | 0.74 | 0.33 |
| Compound 2 | 6.38 | 3.18 |
| Compound 3 | 0.81 | 1.48 |
| Compound 4 | 6.12 | 2.82 |

As can be seen from Table 1, the compounds of the present application (e.g. compounds 1, 2, 3 and 4) have a extremely potent inhibitory effect against CCR2/CCR5.

Experimental Example 2: Inhibition Tests Against CYP 1A2, CYP 2D6, CYP 3A4M, CYP 3A4T and hERG 1. Inhibition Tests Against CYP 1A2, CYP 2D6, CYP 3A4M, and CYP 3A4T
CYP 1A2:
Probe substrate: Phenacetin, National Institute of Control of Pharmaceutical & Biological Products, 100095.
Positive control: alpha-naphthoflavane, ACras, A0331533.
CYP 2D6:
Probe substrate: Dextromethorpha, Beijing Jinbao, 100201.
Positive control: Quinidine, Damas-bata, P1176507.
CYP 3A4M:
Probe substrate: Midazolam, National Institute of Control of Pharmaceutical & Biological Products, 171265.

Positive control: Ketoconazole, purchased from Dingdang Chemical, DTYC 0516-17.

CYP 3A4T:

Probe substrate: Testosterone, European Pharmacopoeia (EP) Reference Standard, Sigma-Aldrich, T0100000.

Positive control: Ketoconazole, Dingdang Chemical, DTYC 0516-17.

A probe substrate (50 μl), PBS (49 μl) and a test compound in different concentrations (0.05 μM, 0.15 μM, 0.5 μM, 1.5 μM, 5 μM, 15 μM, 50 μM) or a positive control (1 μl) were mixed with human liver microsomes (HLM, 50 μl) to give 150 μl of a mixed liquid, which was subjected to pre-incubation (37° C.) for 5 min, then added with NADPH (50 μl) and incubated for 30 min. The reaction was quenched by adding 200 μl of glacial acetonitrile. An appropriate volume of an internal standard substance was added, and after vortex treatment and centrifugation, the supernatant was obtained.

The detection was performed by using LC-MS/MS. The mass spectrometer was API 5500, the liquid chromatograph was Waters ACQUITY UPLC I-CLASS system. The chromatographic column was Hypersil GOLD $C_{18}$, 1.9 μm particle size, 50×2.1 mm; mobile phase A: water+0.1% formic acid, mobile phase B: acetonitrile; flow rate: 0.4 ml/min, column temperature: 40° C. The ion source as used was ESI source positive ion mode, and the scanning mode was Multiple Reaction Monitoring (MRM).

By using solvent group (DMSO) as negative control, the concentrations of the main metabolite converted from the probe substrate in the case of different concentrations of the test compound were measured, to determine the half inhibition concentration of the compound ($IC_{50}$). The half inhibition concentration ($IC_{50}$) results of the compound were shown in Tables 2-3.

2. hERG Inhibition Test:

Different concentrations (1 μM and 10 μM) of the test compound and 30 μM positive control Quinidine were formulated. HEK293 cells over-expressing hERG potassium ion channels were cultured in 5% $CO_2$ incubator at 37° C. When the density of the cells reaches 80% of the Petri dish, the cells was washed with phosphate buffer solution (PBS), followed by digestion with Trypsin/EDTA for 2-3 minutes. The digestion was terminated by adding cell culture medium, then the solution was transferred and centrifuged to remove the supernatant, and added with cell culture medium (DMEM, 15% fetal bovine serum and 1% 100×Penicillin-Streptomycin). After uniformly mixing, the cells were dripped onto a circular slide and cultured in a Petri dish to obtain the test cells.

Channel current was recorded by applying electrophysiological manual patch clamp in a whole-cell recording mode: extracellular fluid was perfused until the current was stable, after the peak value of the tail current (control current value) was recorded, the extracellular fluid containing different concentrations of the test compound was perfused, continuously recording was conducted until the inhibition effect of the medicine on the hERG current reach stable, and the peak value of the tail current (current value after drug administration) was recorded.

The results of this experiment were shown in Table 4.

TABLE 2

Inhibition results of the compounds against CYP

| Compound | CYP 1A2 (μM) | CYP 2D6 (μM) |
|---|---|---|
| Compound 1 | >10 | >10 |
| Compound 2 | >10 | >10 |
| Compound 3 | >10 | >10 |
| Compound 4 | >10 | >10 |

TABLE 3

Inhibition results of the compounds against CYPP

| Compound | CYP 3A4M (μM) | CYP 3A4T (μM) |
|---|---|---|
| Cenicriviroc | 3.43 | 12.7 |
| Compound 2 | 27.8 | 62.2 |
| Compound 3 | 13.3 | 32.3 |
| Compound 4 | 15.3 | 48.3 |

TABLE 4

Inhibition results of the compounds against hERG

| Compound | hERG (μM) |
|---|---|
| Compound 2 | >10 |
| Compound 3 | >10 |
| Compound 4 | >10 |

As can be seen from Tables 2-4, compounds of the present application have weak induction effect on CYP enzyme, no inhibition effect on hERG channel, and no obvious cardiotoxicity. The compounds of the present application (such as compound 1, compound 2, compound 3 and compound 4) have better properties in the aspects of CYP and hERG and have better safety.

Experimental Example 3: Rat Pharmacokinetic (PK) Studies

The test compound was administered intragastrically (p.o.) to male SD rats at a dose of 5 mg/kg. The solvent system was 0.5% MC during the p.o. administration. After p.o. administration, blood was collected for PK studies at 5 min, 15 min, 30 min, 1 h, 2 h, 4 h, 6 h, 8 h, and 24 h. After p.o. administration, liver tissues were collected at 15 min, 1 h, 4 h, 8 h and 24 h, and the liver tissue sample, after being subjected to protein precipitation treatment, was analyzed by a LC-MS/MS. The mass spectrometer was API 5500, and the liquid chromatograph was Waters ACQUITY I CLASS system: chromatographic column: Agela ASB C18 column (2.1 mm×50 mm, 1.9 μm); mobile phase A: water+0.1% formic acid, mobile phase B: acetonitrile; flow rate: 0.4 mL/min, column temperature: 40° C. The ion source as used was ESI source positive ion mode, and the scanning mode was Multiple Reaction Monitoring (MRM). The test results were shown in Table 5.

TABLE 5

Rat pharmacokinetic data of the compound

| Compound No. | Administration Route | Object | Dose (mg/kg) | $AUC_{last}$ | $C_{max}$ | $T_{1/2}$ (h) | F % |
|---|---|---|---|---|---|---|---|
| Compound 3 | p.o. | Blood plasma | 5.00 | 165 ± 36 (h * ng/ml) | 49.7 ± 10.6 (ng/ml) | 1.93 ± 0.37 | 20.9 ± 4.5 |
| | | Liver | 5.00 | 386938 ± 30242 (h * ng/g) | 26600 ± 200 (ng/g) | 7.20 ± 0.50 | / |
| Cenicriviroc | p.o. | Blood plasma | 5.00 | 6326 ± 3440 (h * ng/ml) | 746 ± 428 (ng/ml) | 4.33 ± 0.87 | 10.8 ± 3.5 |
| | | Liver | 5.00 | 6033 ± 2193 (h * ng/g) | 688 ± 229 (ng/g) | 3.93 ± 1.88 | / |

"/" indicates absence

As can be seen from Table 5, the exposure of the compound of the present application (for example compound 3) in the liver of the rats was about 2345 folds higher than that in the plasma; the drug concentration in the liver was about 530 folds higher than that in the plasma; the $T_{1/2}$ in the liver was 7.20±0.50 h. The compound of the present application had very low exposure quantity ($AUC_{last}$) and drug concentration ($C_{max}$) in the plasma, whereas had very high exposure quantity and drug concentration in the liver, and thus it has very remarkable liver targeting property and good pharmacokinetic properties.

The other compounds in the present application also had similar $AUC_{last}$, $C_{max}$ and $T_{1/2}$ to the above compound, and they had similar pharmacokinetic properties in rats to those as above described.

In summary, the compound of the present application shows good activities in the aspect of in vitro drug efficacy, and have excellent pharmacokinetic properties and remarkable liver targeting property, and thus they can be applied in the manufacture of drugs for treatment of CCR2- and CCR5-mediated diseases, especially nonalcoholic fatty liver diseases (NAFLD) or the like.

In addition to those embodiments as described herein, according to the preceding depictions, many modifications to the invention are obvious for a person skilled in the art. Such modifications are also intended to fall within the scope of the claimed as attached. Each reference documents (including all patents, patent applications, journals, books, and any other publications) cited in the present application are incorporated as the reference in its entirety.

-continued
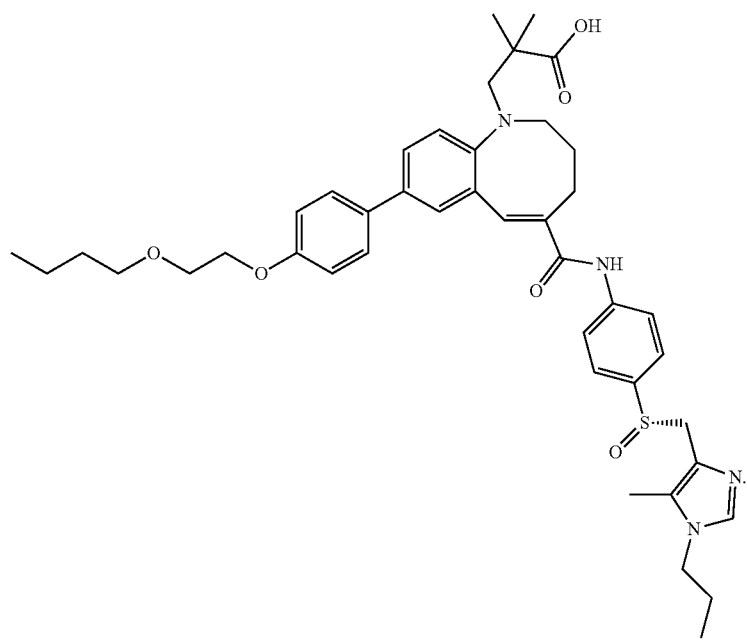

The invention claimed is:

1. A compound of general formula I or a pharmaceutically acceptable salt, ester, solvate, stereoisomer, tautomer, or crystalline form, or a mixture of the aforementioned:

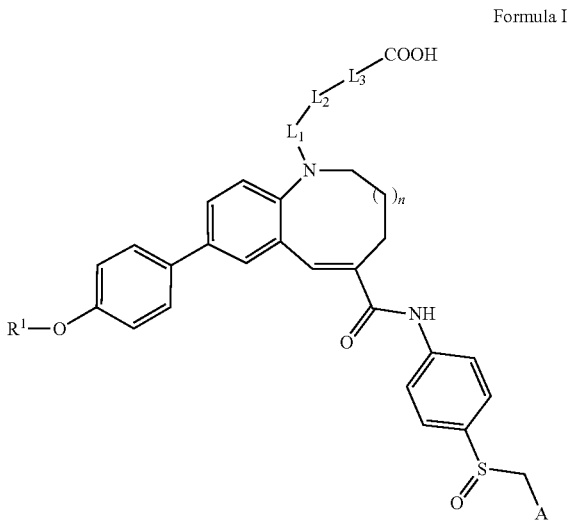

Formula I wherein $R^1$ is selected from $C_{1-4}$ alkyl, said $C_{1-4}$ alkyl is optionally substituted with $R^2$; $R^2$ is selected from $C_{1-4}$ alkoxy;

$L_1$ is selected from $C_{1-3}$ alkylene and $C_{3-5}$ cycloalkylene;

$L_2$ is absent or selected from —NH—, —N($CH_3$)—, —C($CH_3$)$_2$—, —CH=CH—, —($C_{1-3}$ alkyleneoxy)$_{y1}$-($C_{1-3}$ alkyleneoxy)$_{y2}$-, $C_{3-6}$ cycloalkylene, $C_{6-8}$ arylene, $C_{5-8}$ heteroarylene, and 3- to 6-membered heterocyclylene, wherein $y_1$ and $y_2$ are each independently selected from 0, 1, or 2;

$L_3$ absent or selected from $C_{1-6}$ alkylene and $C_{2-6}$ alkenylene;

A is

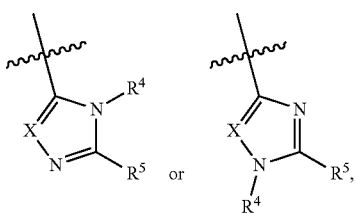

wherein $R^4$ is selected from hydrogen, deuterium, or $C_{1-6}$ alkyl and $C_{3-6}$ cycloalkyl that are optionally substituted with $R^6$, $R^6$ is selected from deuterium, hydroxyl, —CN, $C_{1-4}$ alkoxy and $C_{3-6}$ cycloalkoxy;

each $R^5$ is selected from hydrogen, deuterium, halogen, —CN, $C_{1-6}$ alkyl, halogenated $C_{1-6}$ alkyl, $C_{1-6}$ alkylene-CN, $C_{1-6}$ alkylene-OH, $C_{1-6}$ alkylene-$C_{1-6}$ alkoxy, $C_{3-6}$ cycloalkyl, $C_{3-6}$ heterocycloalkyl, $C_{6-10}$ aryl and $C_{5-12}$ heteroaryl;

X is selected from N and C—$R^5$, each $R^5$ is identical or different;

n is selected from 0, 1 or 2.

2. The compound according to claim 1 or a pharmaceutically acceptable salt, ester, solvate, stereoisomer, tautomer, or crystalline form, or a mixture of the aforementioned, wherein, $R^1$ is

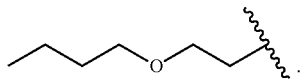 [SMILES: *CCOCCCC]

3. The compound according to claim 1 or a pharmaceutically acceptable salt, ester, stereoisomer, tautomer, or crystalline form, or a mixture of the aforementioned, wherein, $L_1$ is selected from —$CH_2$— or —$CH_2$—$CH_2$—.

4. The compound according to claim 1 or a pharmaceutically acceptable salt, ester, solvate, stereoisomer, tautomer, or crystalline form, or a mixture of the aforementioned, wherein, $L_2$ is absent or selected from —NH—, —N($CH_3$)— and —C($CH_3$)$_2$—.

5. The compound according to claim 1 or a pharmaceutically acceptable salt, ester, solvate, stereoisomer, tautomer, or crystalline form, or a mixture of the aforementioned, wherein, $L_3$ is absent or selected from —C($CH_3$)$_2$—, —$CH_2$—, and —CH═CH—.

6. The compound according to claim 1 or a pharmaceutically acceptable salt, ester, solvate, stereoisomer, tautomer, or crystalline form, or a mixture of the aforementioned, $R^4$ is $C_{1-6}$ alkyl optionally substituted with $R^6$, $R^5$ is independently selected from hydrogen, methyl, trifluoromethyl and cyclopropyl;

$R^6$ is selected from deuterium, hydroxyl, —CN, and $C_{1-4}$ alkoxy.

7. The compound according to claim 6 or a pharmaceutically acceptable salt, ester, solvate, stereoisomer, tautomer, or crystalline form, or a mixture of the aforementioned, wherein X is selected from N and C—$R^5$, $R^5$ is selected from hydrogen, methyl, trifluoromethyl, and cyclopropyl.

8. The compound according to claim 1 or a pharmaceutically acceptable salt, ester, solvate, stereoisomer, tautomer, or crystalline form, or a mixture of the aforementioned, wherein A is selected from

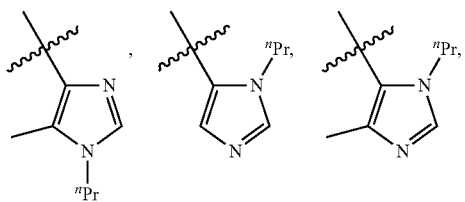

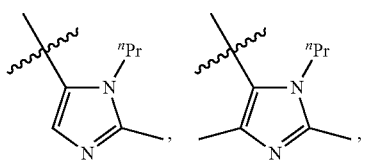

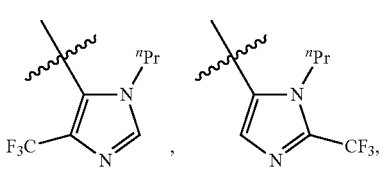

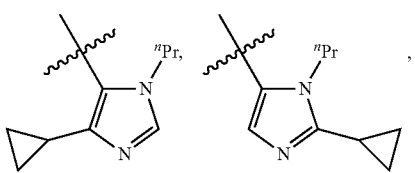

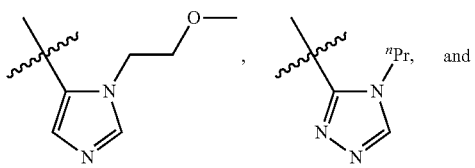

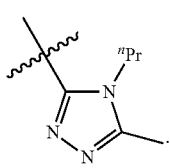

9. The compound according to claim 1 or a pharmaceutically acceptable salt, ester, solvate, stereoisomer, tautomer, or crystalline form, or a mixture of the aforementioned, wherein $L_1$ is selected from methylene and ethylene;

$L_2$ is absent or selected from —NH—, —N($CH_3$)— and —C($CH_3$)$_2$—;

$L_3$ is absent or —$CH_2$.

10. The compound according to claim 1 or a pharmaceutically acceptable salt, ester, solvate, stereoisomer, tautomer, or crystalline form, or a mixture of the aforementioned, wherein the compound has a structure shown by formula $II_a$ or formula $II_{a'}$:

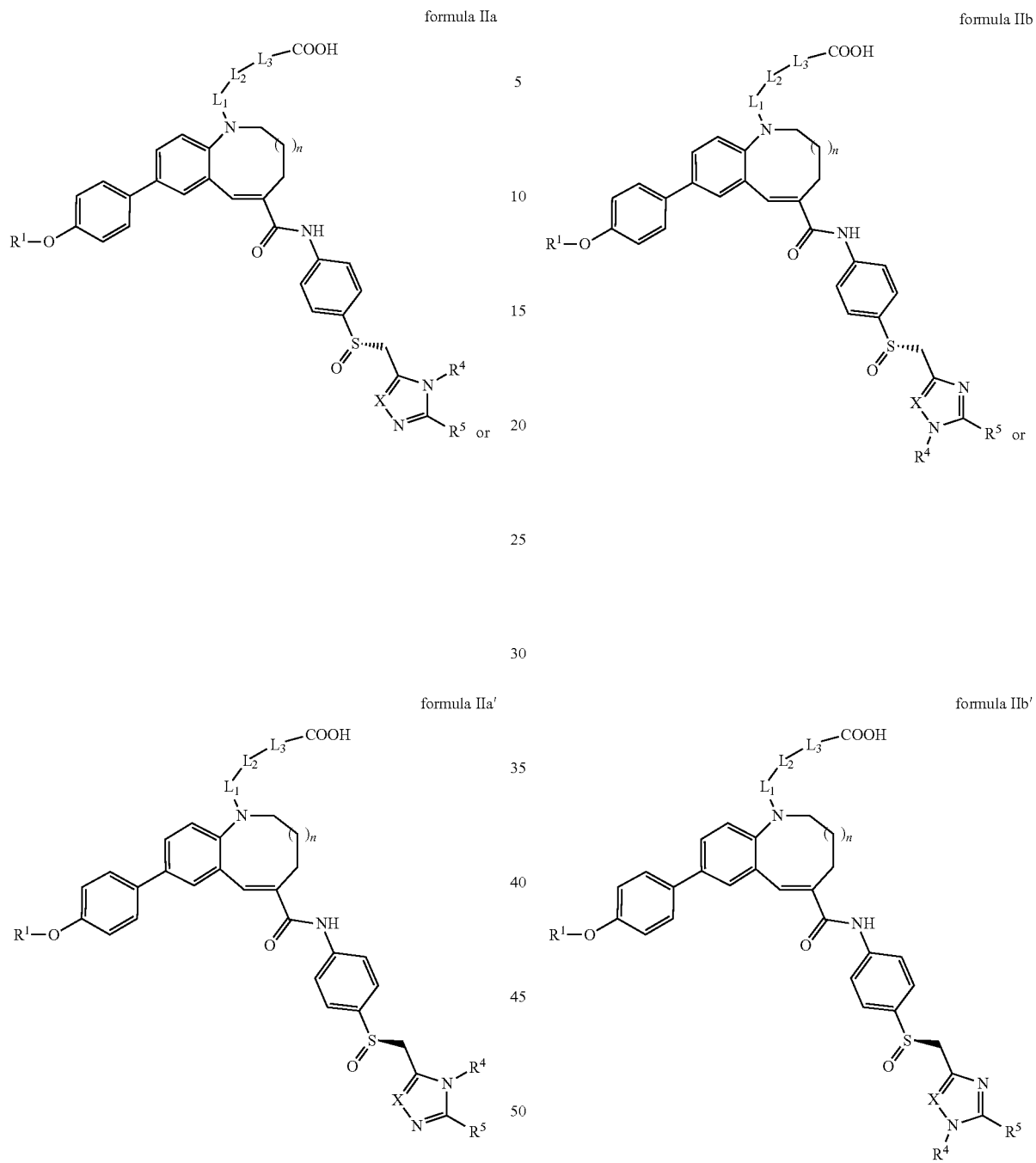

wherein $R^1$, $R^4$, $R^5$, X, $L_1$, $L_2$, $L_3$ and n are as defined in claim 1.

11. The compound according to claim 1 or a pharmaceutically acceptable salt, ester, solvate, stereoisomer, tautomer, or crystalline form, or a mixture of the aforementioned, wherein the compound has a structure as shown by formula II$_b$ or formula II$_b$′:

wherein $R^1$, $R^4$, $R^5$, X, $L_1$, $L_2$, $L_3$ or n are as defined in claim 1.

12. The compound according to claim 10 or a pharmaceutically acceptable salt, ester, solvate, stereoisomer, tautomer, or crystalline form, or a mixture of the aforementioned, wherein n is selected from 1 or 2.

13. The compound according to claim 1 or a pharmaceutically acceptable salt, ester, solvate, stereoisomer, tautomer, or crystalline form, or a mixture of the aforementioned, wherein the compound is selected from:

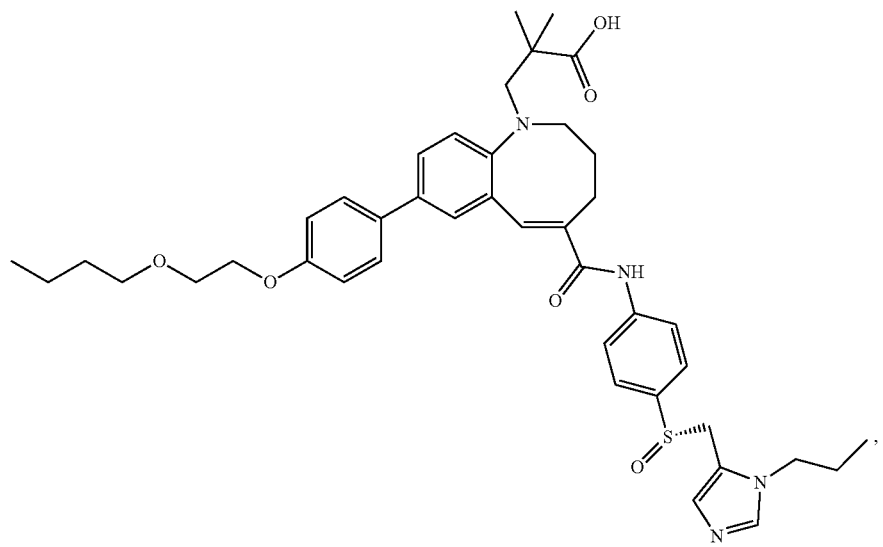
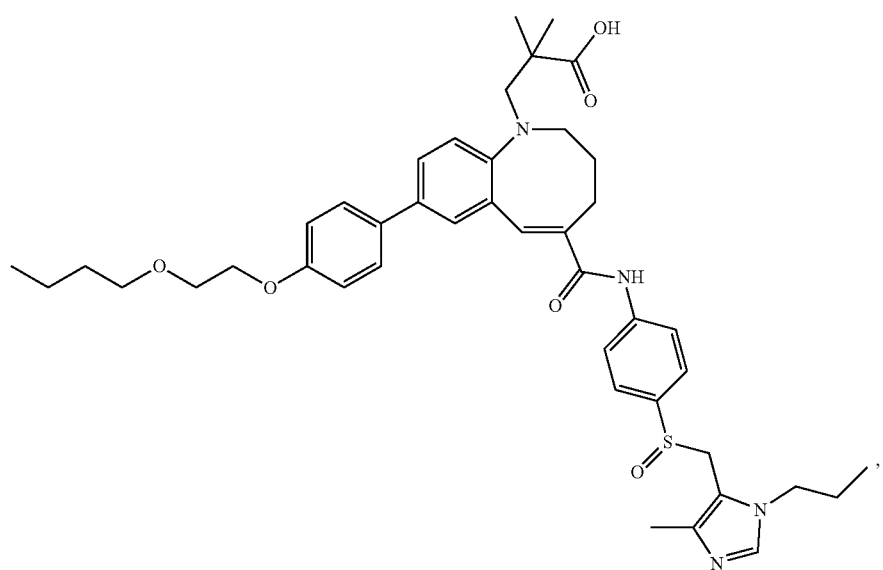
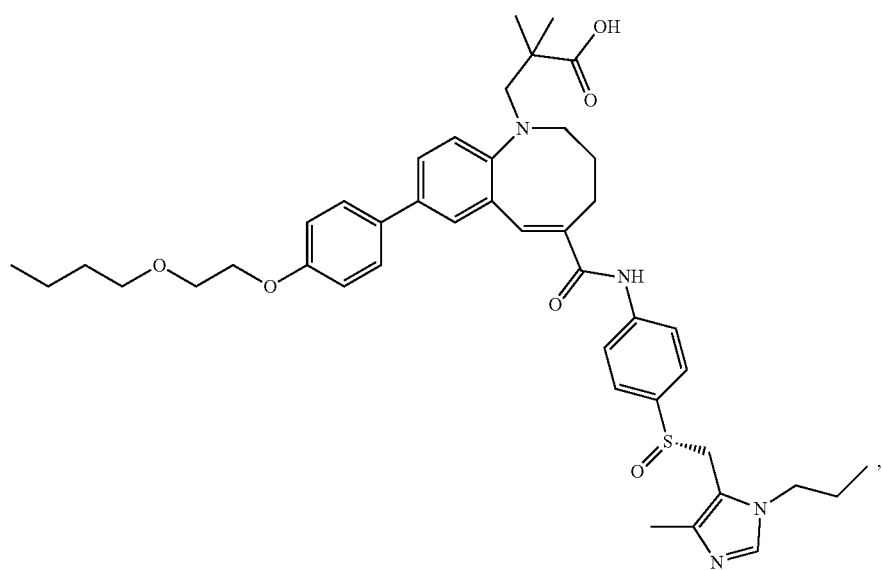

-continued
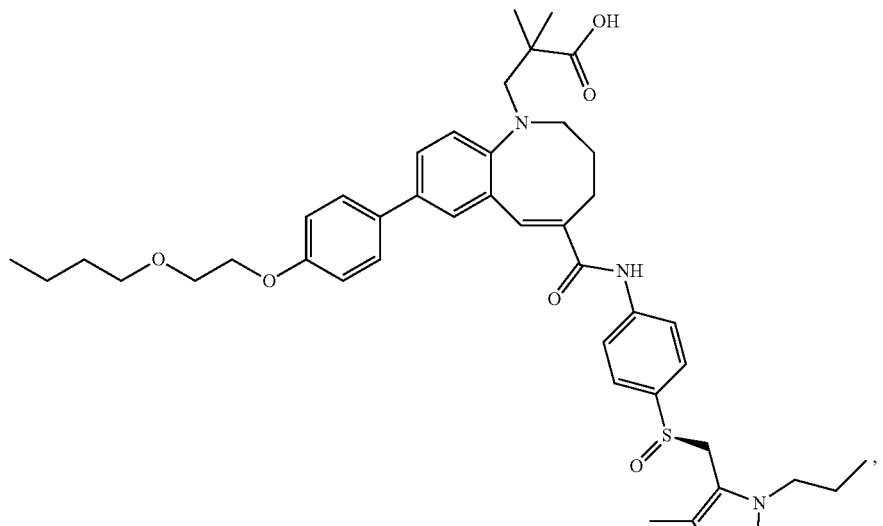
4
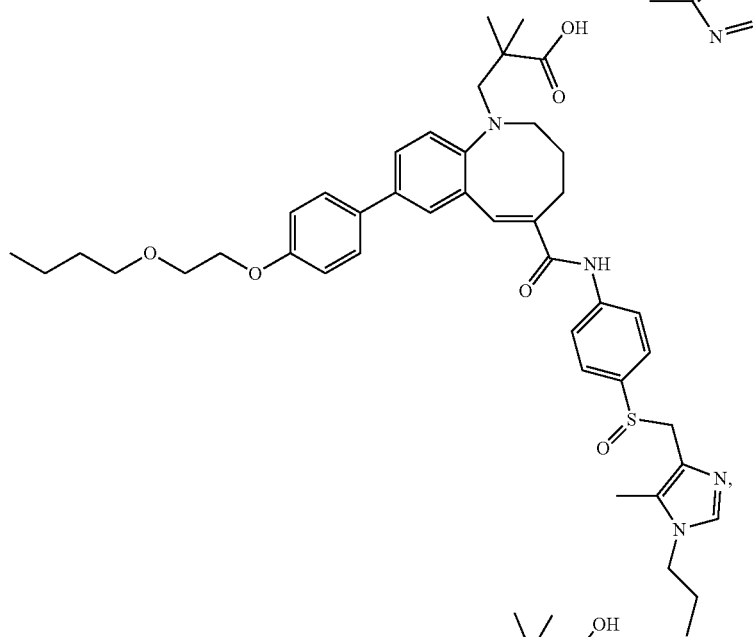
5
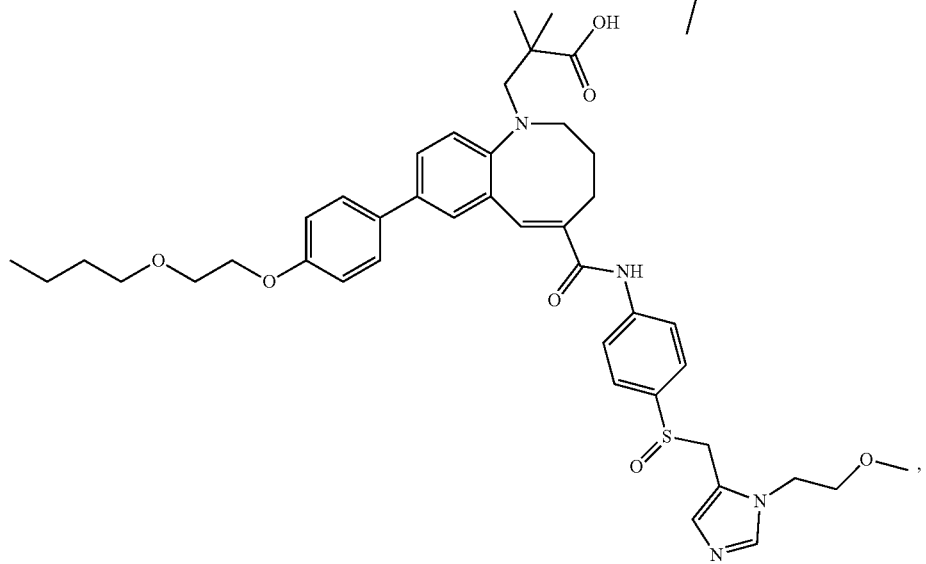
6

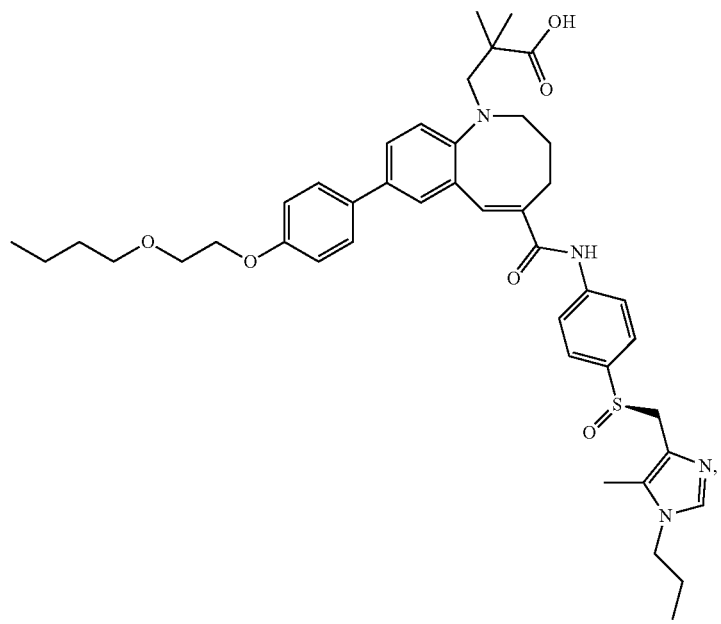
7
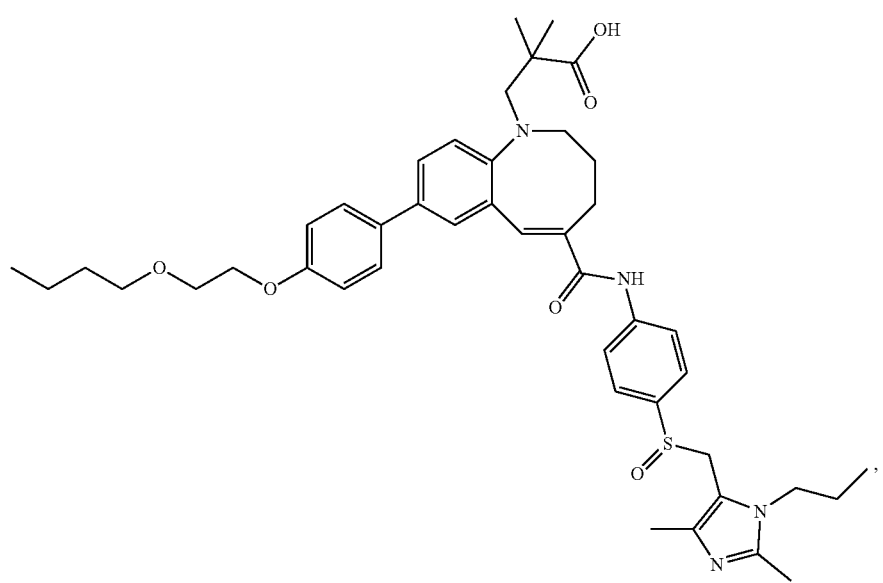
8

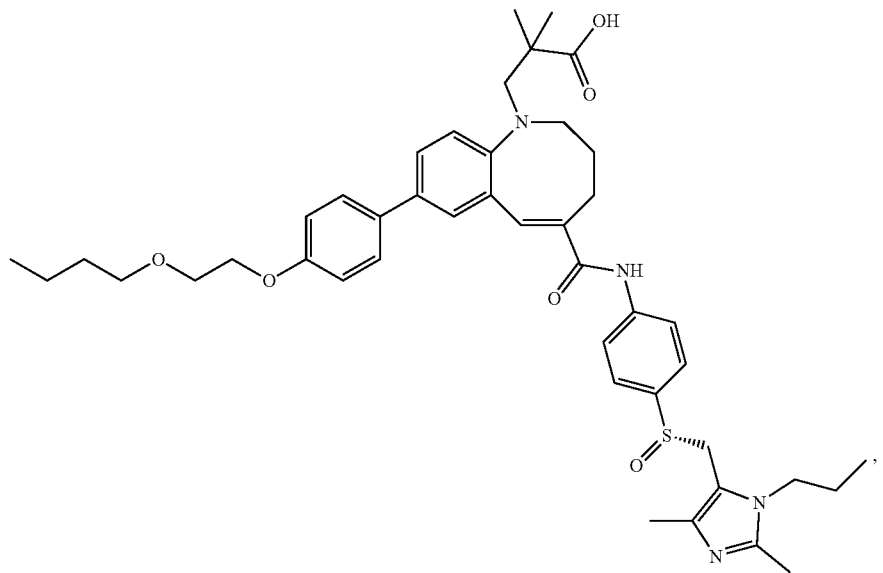
9
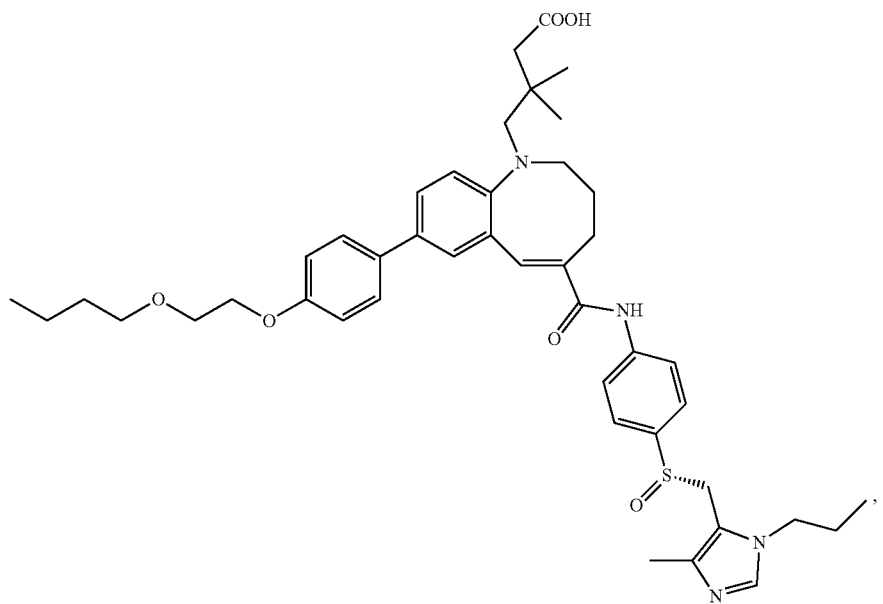
10

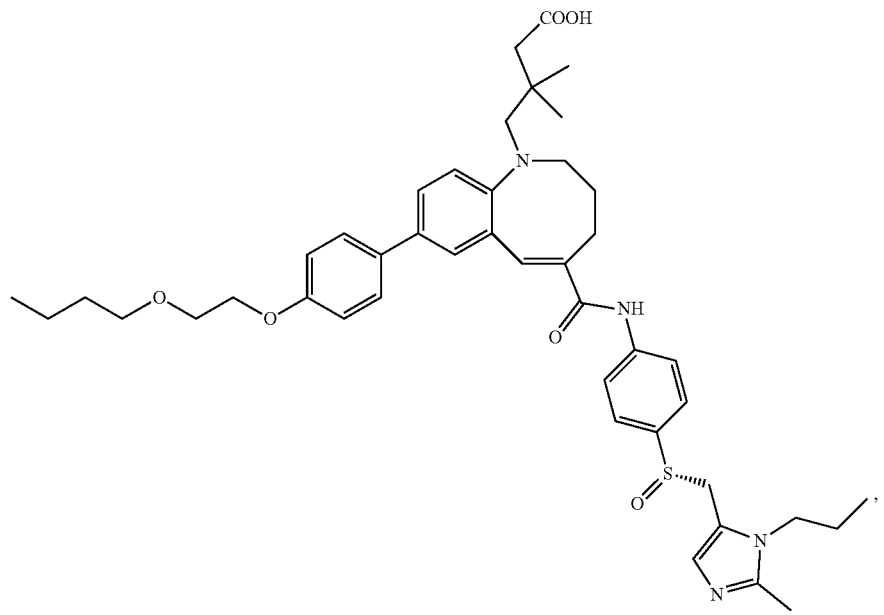
11
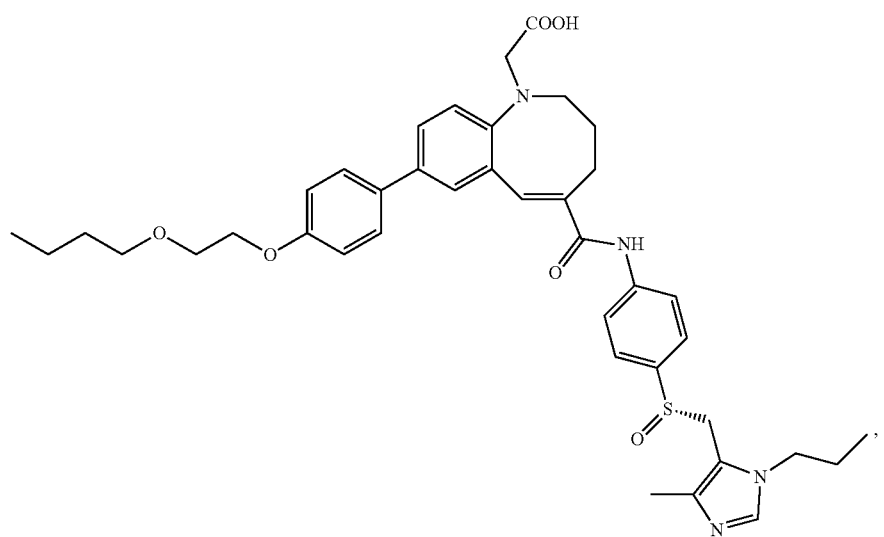
12

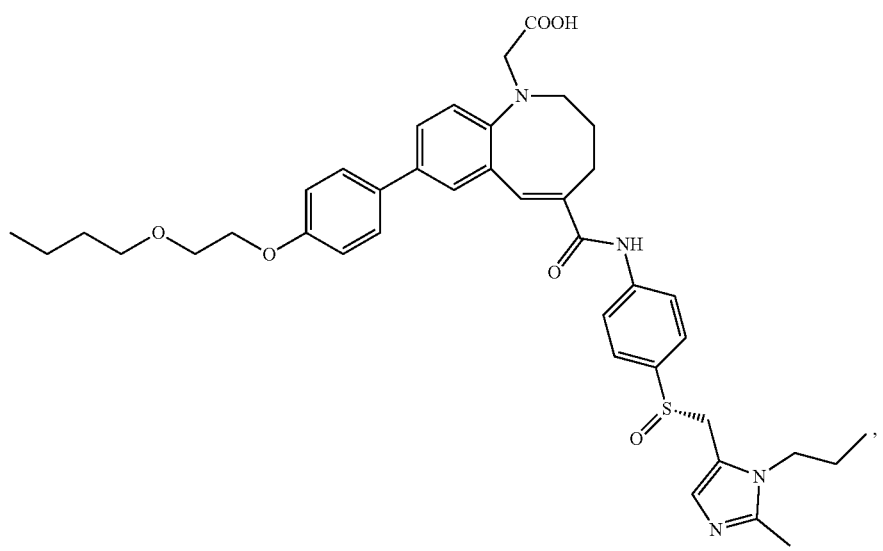
13
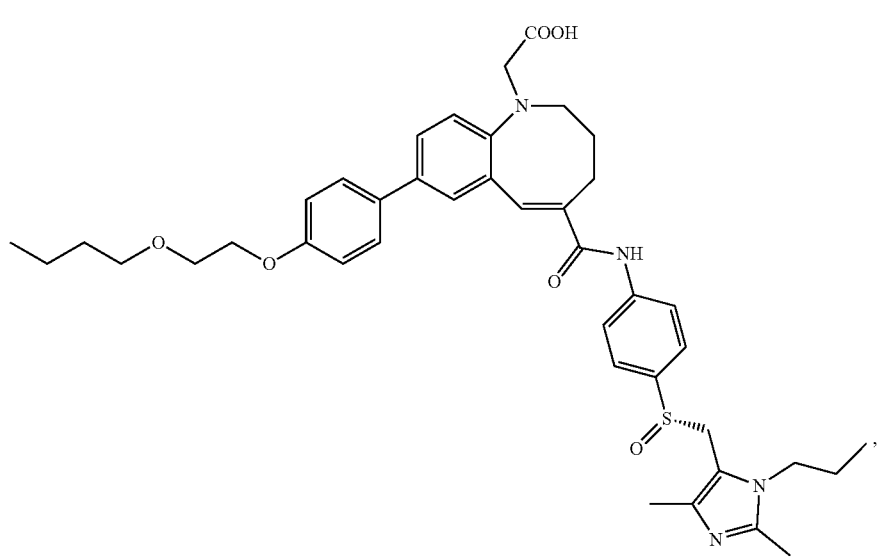
14
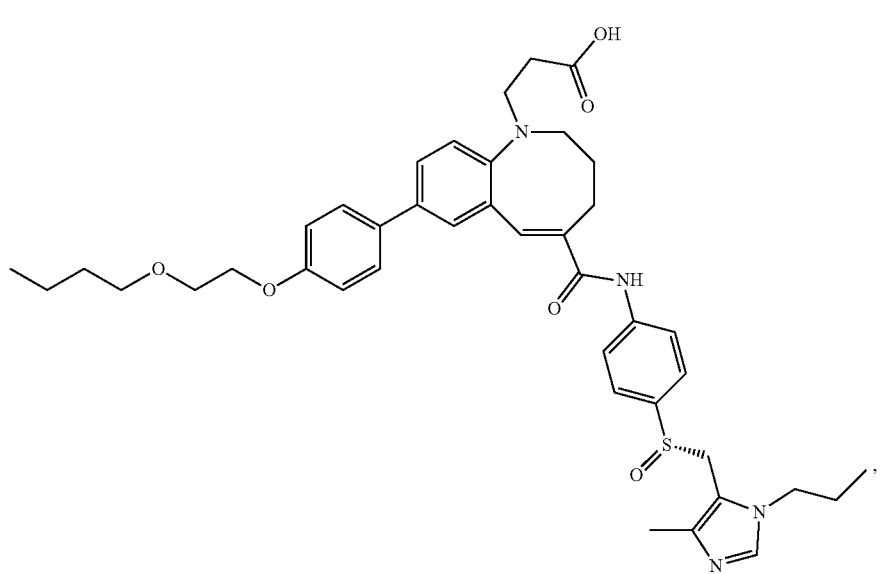
15

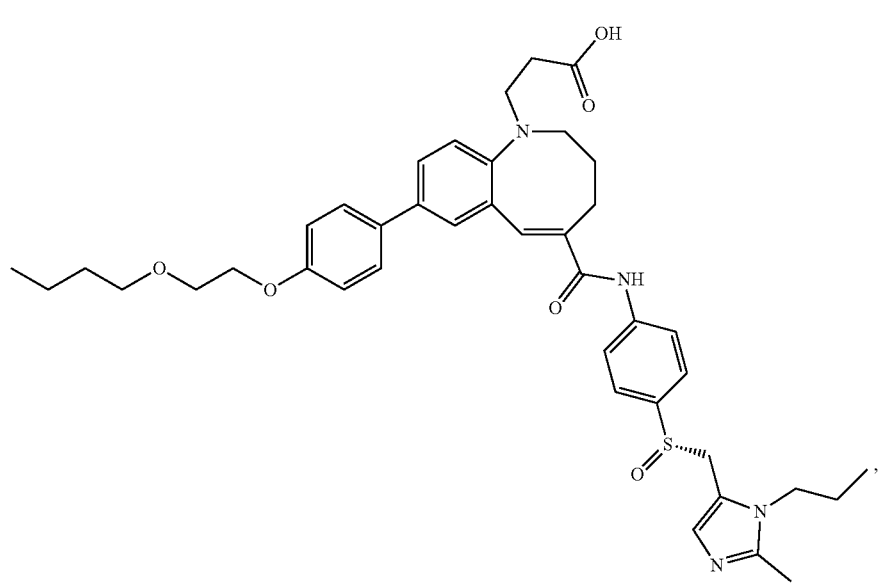
16
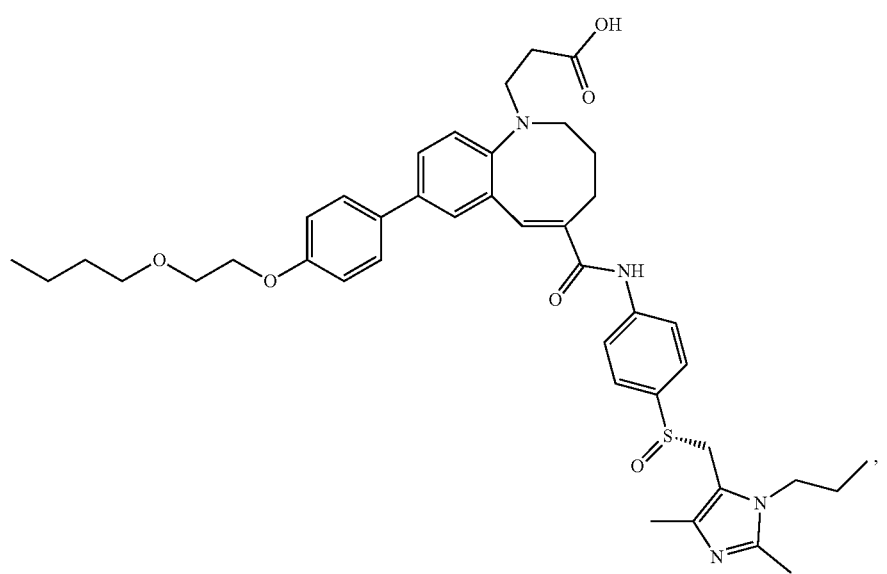
17

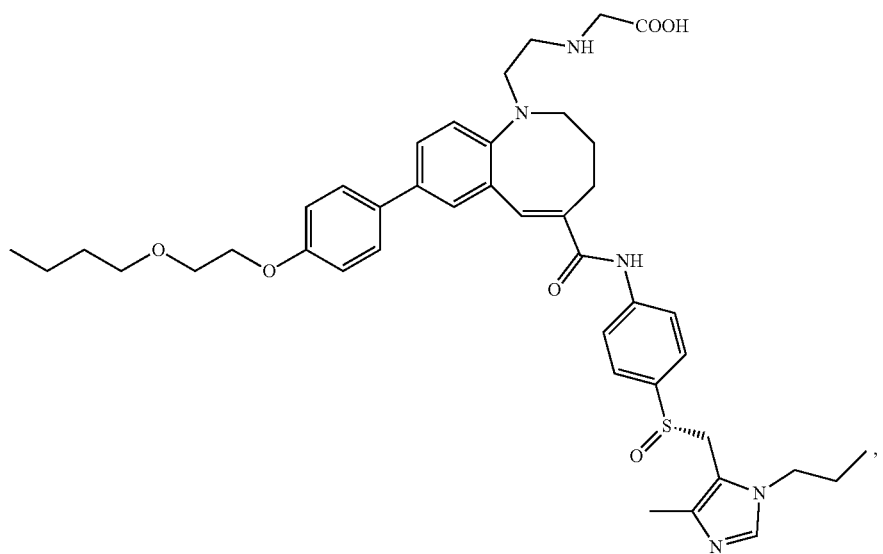
18
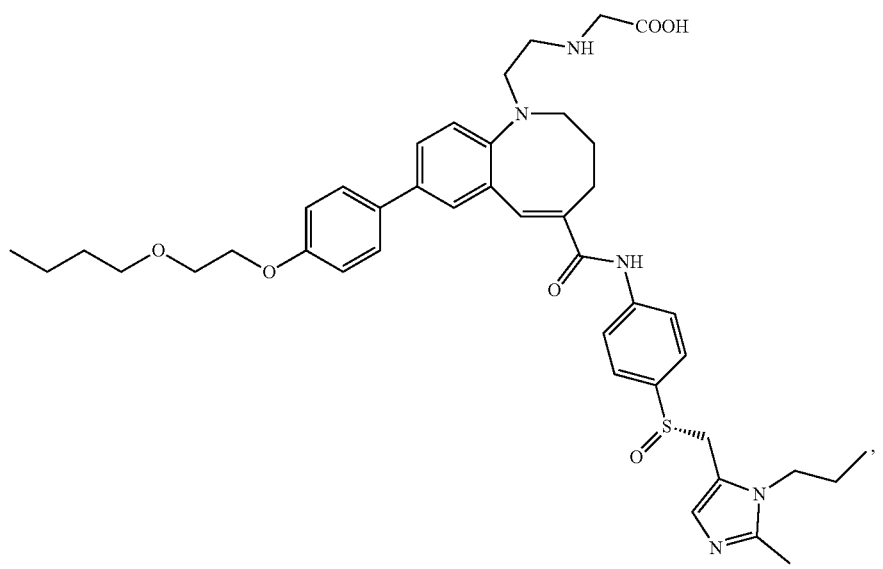
19
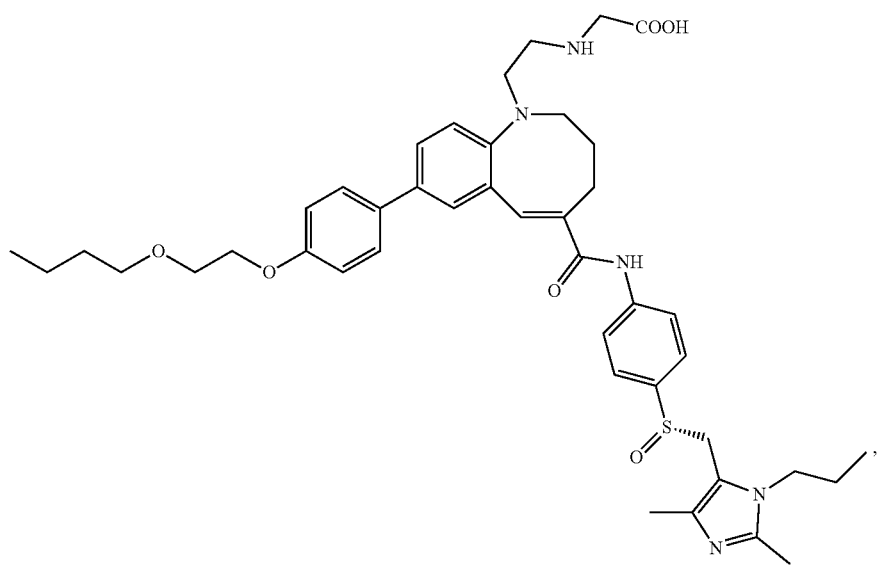
20

-continued
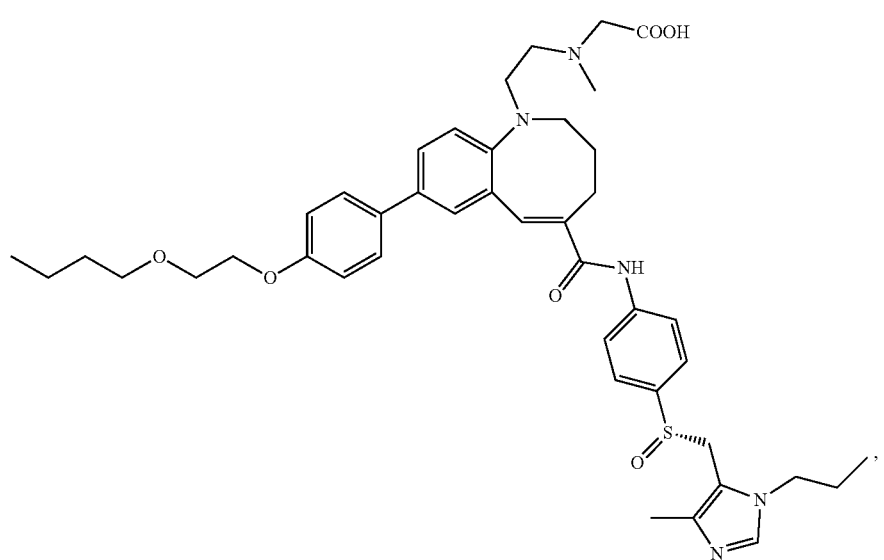
21
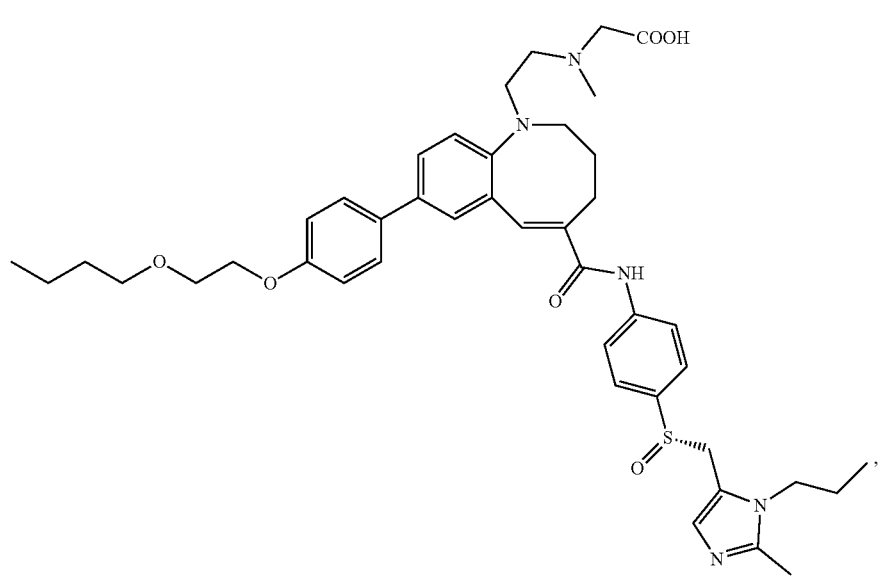
22
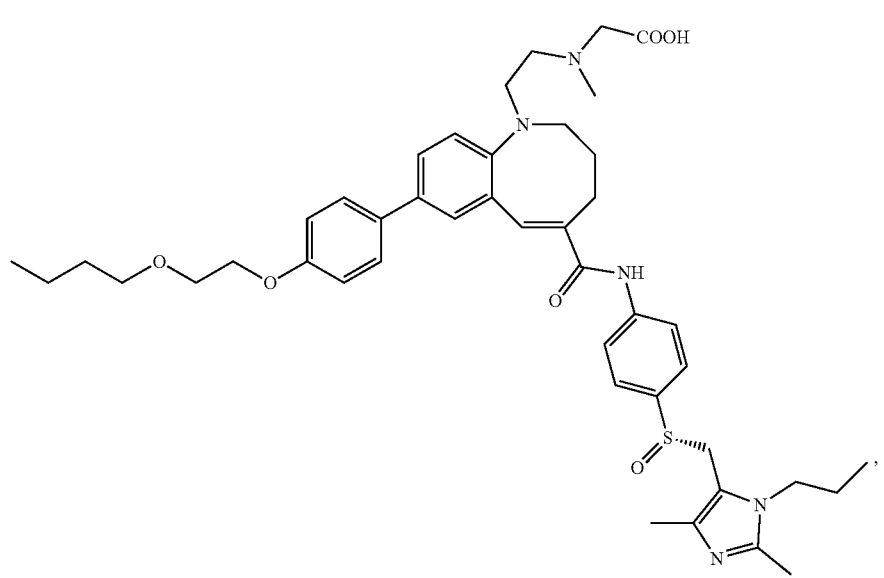
23

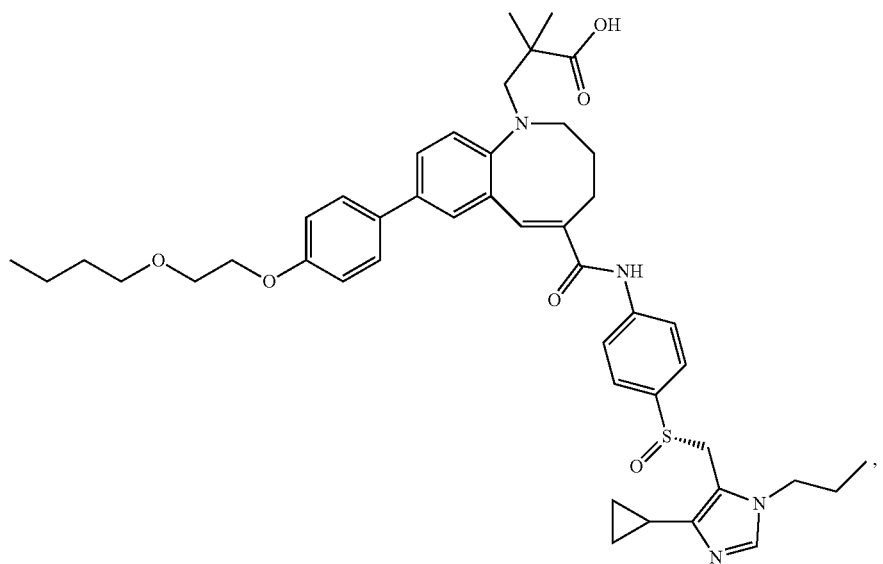
24
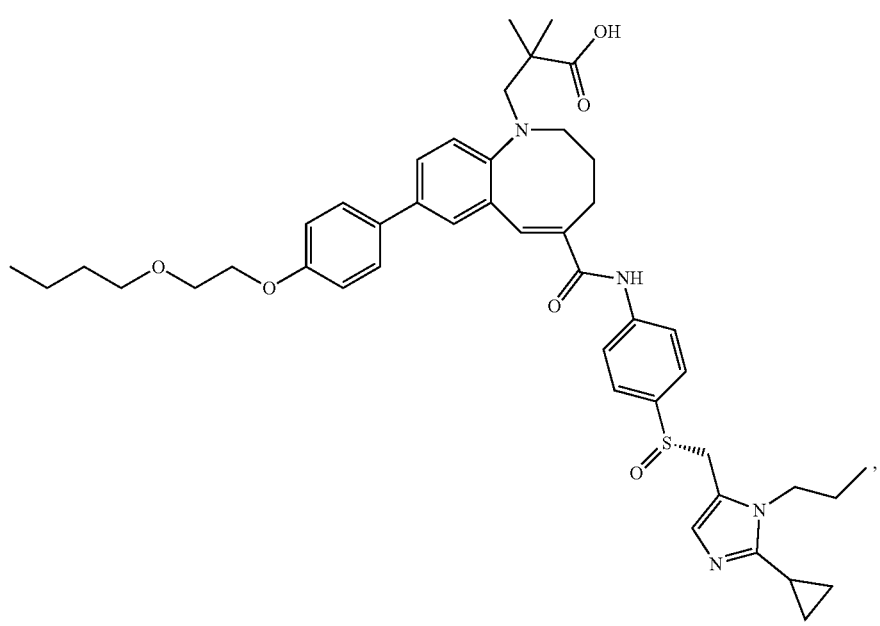
25

26
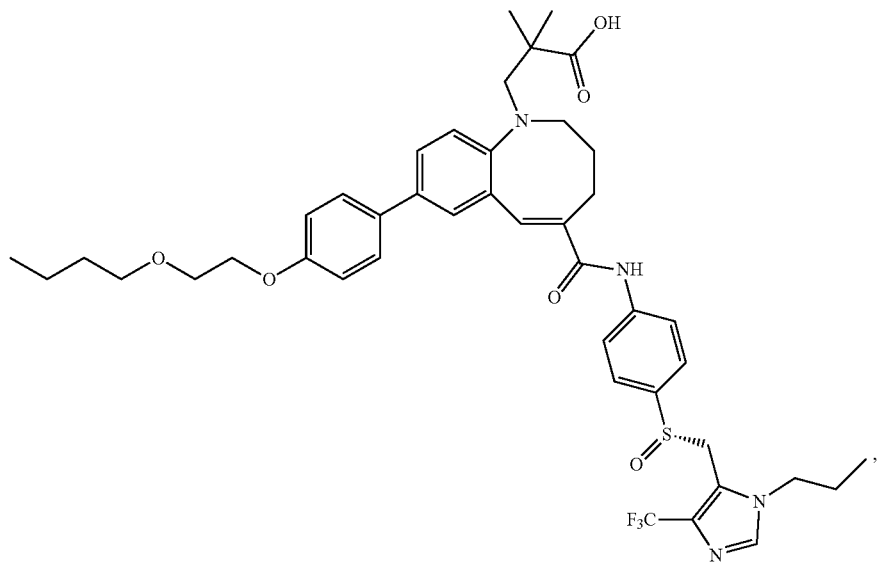
27
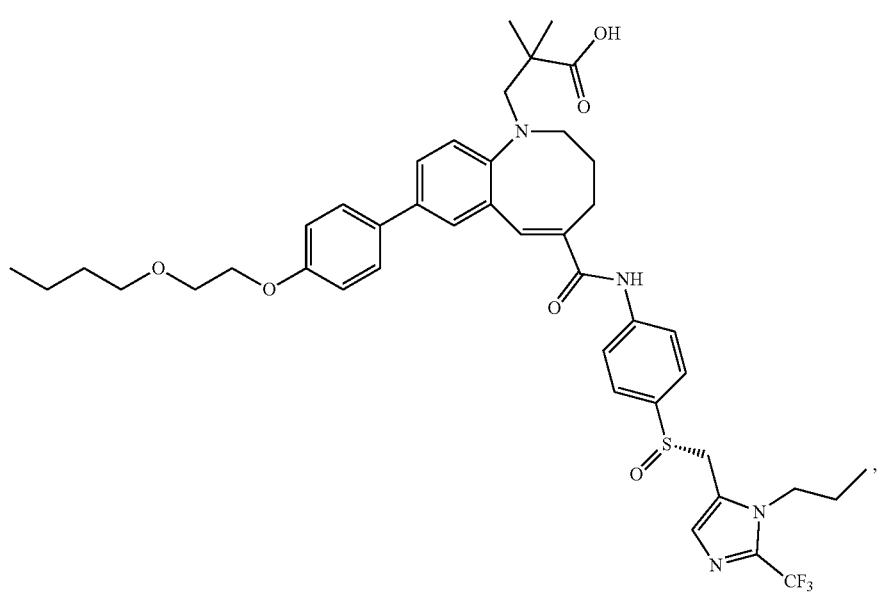

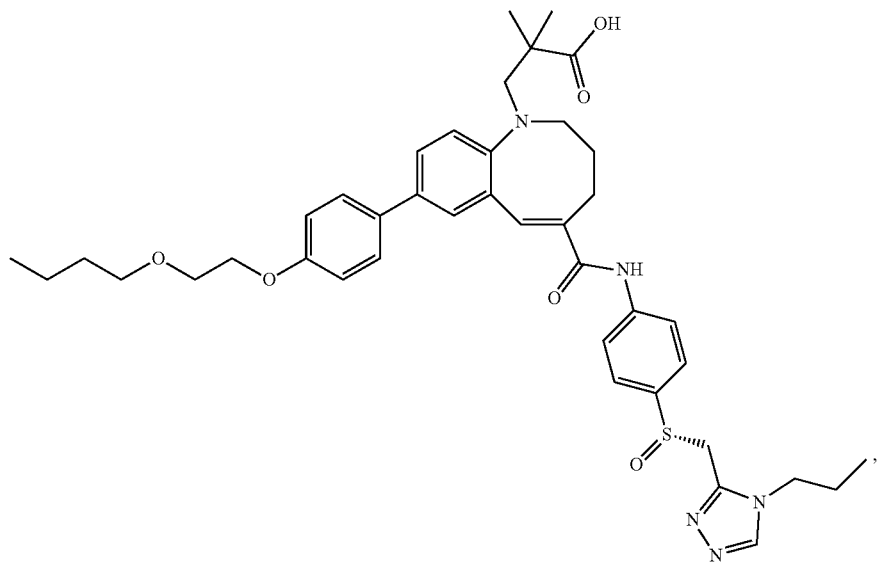
28
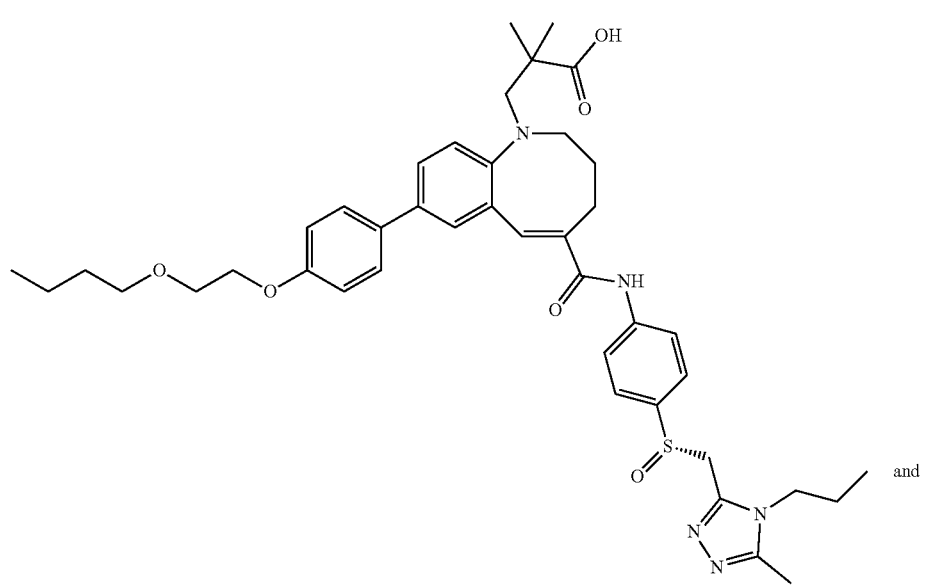
29